(12) United States Patent
Osbourn et al.

(10) Patent No.: US 7,378,278 B2
(45) Date of Patent: May 27, 2008

(54) ENZYMES INVOLVED IN TRITERPENE SYNTHESIS

(75) Inventors: Anne Osbourn, Norwich (GB);
Xiaoquan Qi, Norfolk (GB)

(73) Assignee: Plant Bioscience Limited, Norwich (GB)

( * ) Notice: Subject to any disclaimer, the term of this patent is extended or adjusted under 35 U.S.C. 154(b) by 0 days.

(21) Appl. No.: 11/248,986

(22) Filed: Oct. 12, 2005

(65) Prior Publication Data

US 2006/0112448 A1 May 25, 2006

Related U.S. Application Data

(60) Provisional application No. 60/619,203, filed on Oct. 15, 2004.

(51) Int. Cl.
*C12N 15/82* (2006.01)
*C12N 5/04* (2006.01)

(52) U.S. Cl. .................. 435/468; 536/23.6; 435/320.1; 435/419

(58) Field of Classification Search ..................... None
See application file for complete search history.

(56) References Cited

U.S. PATENT DOCUMENTS

2003/0217384 A1 11/2003 Harvell et al.

FOREIGN PATENT DOCUMENTS

WO    WO/01/46391 A2    6/2001

OTHER PUBLICATIONS

Guo et al. 2004, Proc. Natl. Acad. Sci. USA 101: 9205-9210.*
Hill et al 1998, Biochem. Biophys. Res. Comm. 244:573-577.*
Lazar et al. 1988, Mol. Cell. Biol. 8:1247-1252.*
Falcon-Perez JM et al. 1999, J Biol Chem. 274:23584-90.*
Lepesheva et al. 2003 Biochemistry 42:9091-9101.*
Anne E. Osbourn, Saponins In Cereals, Phytochemistry 64:1-4, 2003.
K. R. Price et al., The Chemistry and Biological Significance of Saponins in Foods and Feedingstuffs, CRC Crit. Rev. Food Sci. Nutr., vol. 26:27-133, 1987.
P. J. Rayapati et al., A Linkage Map of Diploid Avena Based on RFLP Loci and a Locus Conferring Resistance to Nine Isolates of Puccinia Coronata Var. 'Avenae', Theor. Appl. Genet., vol. 89:831-837, 1994.
S. L. Kelly et al., An Old Activity in the Cytochrome P450 Superfamily (CYP51) and a New Story of Drugs and Resistance, Biochemical Society Transactions, vol. 29(2):122-128, 2001.
Miranda R. Trojanowska et al., Investigation of Avenacin-Deficient Mutants of Avena Strigosa, Phytochemistry, vol. 56:121-129, 2001.
X. Qi et al., A Gene Cluster for Secondary Metabolism in Oat: Implications for the Evolution of Metabolic Diversity in Plants, PNAS, vol. 101(21):8233-8238, 2004.
Galina I. Lepesheva et al., Conservation in the CYP51 Family, Role of the B'Helix/BC Loop and Helices F and G in Enzymatic Function, Biochemistry, vol. 42:9091-9101, 2003.
David R. Nelson, Cytochrome P450 and the Individuality of Species, Archives of Biochemistry and Biophysics, vol. 369(1):1-10, 1999.
K. Haralampidis et al., A New Class of Oxidosqualene Cyclases Directs Synthesis of Antimicrobial Phytoprotectants in Monocots, PNAS, vol. 98(23):13431-13436, 2001.
K. Papadopoulou et al., Comprised Disease Resistance in Saponin-Deficient Plants, PNAS, vol. 96(22):12923-12928, 1999.

* cited by examiner

*Primary Examiner*—Ashwin Mehta
*Assistant Examiner*—Li Zheng

(57) ABSTRACT

This invention relates to isolated polynucleotides encoding a CYP51H. The invention also relates to the construction of recombinant DNA constructs comprising all or a portion of the isolated polynucleotide of the invention, in sense or antisense orientation, operably linked to at least one regulatory sequence.

18 Claims, 1 Drawing Sheet

ENZYMES INVOLVED IN TRITERPENE SYNTHESIS

Figure 1:
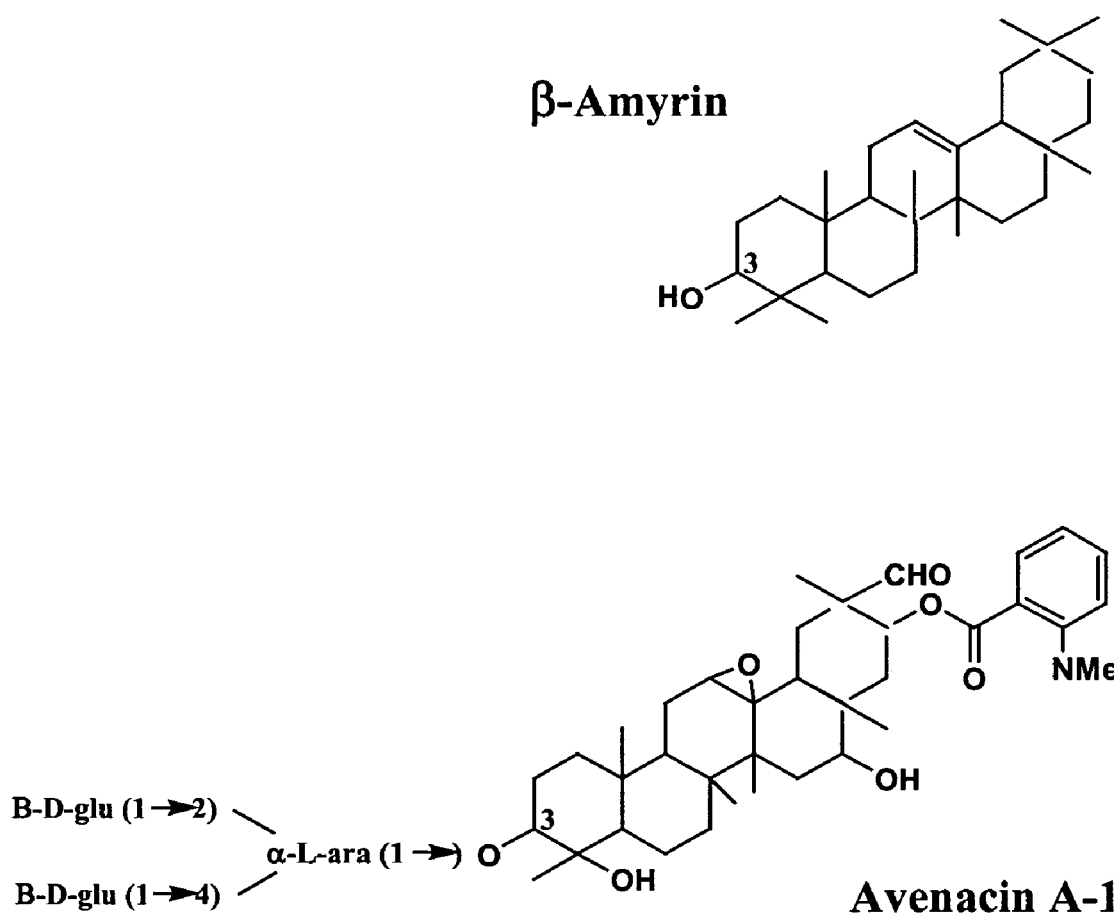

This application claims the benefit of U.S. Provisional Application No. 60/619,203, filed Oct. 15, 2004. The entire content of this application is herein incorporated by reference.

FIELD OF THE INVENTION

This invention is in the field of plant molecular biology. More specifically, this invention pertains to polynucleotides encoding enzymes involved in the modification of β-amyrin during the biosynthesis of β-amyrin-derived triterpenes in plants and seeds. This invention also includes transgenic plants where the altered expression levels of the polynucleotides of the present invention results in altered levels or structures of β-amyrin-derived triterpenes, including saponins.

BACKGROUND OF THE INVENTION

The terpenoids, also called isoprenoids, constitute the largest family of natural products with over 22,000 individual compounds of this class having been described. The triterpenes or terpenoids (hemiterpenes, monoterpenes, sesquiterpenes, diterpenes, triterpenes, tetraterpenes, polyprenols, and the like) play diverse functional roles in plants as hormones, photosynthetic pigments, electron carriers, mediators of polysaccharide assembly, and structural components of membranes. The majority of plant terpenoids are found in resins, latex, waxes, and oils.

Triterpenoids are of relevance to a variety of plant characteristics, including palatability to animals, and resistance to pathogens and predators. Triterpenes are mostly stored in plant roots as their glycosides, saponins (see Price K. R. et al, 1987, *CRC Crit. Rev. Food Sci. Nutr.* 26:27-133). Thus, for example, mutants of the diploid oat species, *Avena strigosa*, which lack the major oat root saponin, avenacin A-1 (so called saponin-deficient or "sad" mutants) have been shown to have compromised disease resistance (Papadopoulou K. et al., 1999, *Proc. Natl. Acad. Sci. U.S.A.* 96:12923-12928). These mutants have increased susceptibility to a number of different root-infecting fungi, including *Gaeumannomyces graminis* var. *tritici*, which is normally non-pathogenic to oats. Genetic analysis suggests that increased disease susceptibility and reduced avenacin content are causally related. Furthermore, a sad mutant which produces reduced avenacin levels (around 15% of that of the wild type) gives only limited disease symptoms when inoculated with *G. graminis* var. *tritici* in comparison to other mutants which lack avenacins completely, providing a further link between avenacin content and disease resistance.

Triterpenoid saponins are synthesized via the isoprenoid pathway by cyclization of 2,3-oxidosqualene to give pentacyclic triterpenoids, primarily oleanane (β-amyrin) or dammarane skeletons. The triterpenoid backbone then undergoes various modifications (oxidation, substitution, and glycosylation), mediated by cytochrome P450-dependent monooxygenases, glycosyltransferases, and other enzymes. In general very little is known about the enzymes and biochemical pathways involved in saponin biosynthesis. The genetic machinery required for the elaboration of this important family of plant secondary metabolites is as yet largely uncharacterized, despite the considerable commercial interest in this important group of natural products. This is likely to be due in part to the complexity of the molecules and the lack of pathway intermediates for biochemical studies. However, the first dedicated step in saponin biosynthesis is now understood to be carried out by the oxidosqualene cyclase β-amyrin synthase, which has recently been cloned and characterized (Haralampidis K. et al., 2001, *Proc. Natl. Acad. Sci. U.S.A.* 98:13431-13436).

Many of the primary modifications to β-amyrin indicated in FIG. 1, which compares the structures of β-amyrin and avenacin A-1, are likely to be mediated by cytochrome P450 monooxygenases. These include oxidation at C16, C21, C30, or C23, and epoxidation at C12, C13. Besides their involvement in saponin biosynthesis, cytochrome P450 monooxygenases are involved in the biosynthesis of a multitude of other compounds, as described in (Nelson D. R., 1999, *Arch. Biochem. Biophys.* 369:1-10). While some single cytochrome P450 monooxygenase enzymes can metabolize multiple substrates, many of these enzymes are highly substrate specific. For example, in maize four P450s (BX2-5) sharing 45-60% amino acid identity belonging to the CYP71C family carry out successive hydroxylation events in the conversion of indole to the cyclic hydroxamic acid 2,4-dihydroxy-1,4-benzoxazin-3-one (DIBOA), each enzyme catalyzing predominantly only one reaction in the pathway. Available P450 structures show that the overall P450 structural fold is preserved during evolution from bacteria through plants and mammals. At the same time there are variable regions that appear to be associated with recognition and binding of structurally diverse substrates and redox partners.

The CYP51 (sterol 14α-demethylase) family is an essential enzyme in sterol biosynthesis and is the only P450 family that serves the same function in different biological kingdoms (Lepesheva G. I. et al., 2003, *Biochemistry* 42:9091-9101; Kelly S. L. et al., 2001, *Biochem. Soc. Trans.* 29:122-128). CYP51 enzymes catalyze the oxidative removal of the 14α-methyl group from lanosterol and 24-methylene-24,25-dihydrolanosterol in yeast and fungi, from obtusifoliol in plants and from 24,25-dihydrolanosterol in mammals. The products of action of sterol 14α-demethylases are $\Delta^{14,15}$-desaturated intermediates in ergosterol (fungi), phytosterol (plants) and cholesterol (animals) biosynthesis. The reaction includes three steps of successive conversion of the 14α-methyl group to 14α-hydroxymethyl, 14α-carboaldehyde, and 14α-formyl intermediates followed by elimination of formic acid with concomitant introduction of the Δ14,15 double bond into the sterol core. CYP51 s are targets for antifungal and cholesterol-lowering drugs.

The present invention describes polynucleotides encoding novel CYP51s, one of which modifies β-amyrin or a β-amyrin derivative. Identification of the genes encoding enzymes responsible for modification of β-amyrin or β-amyrin derivatives in a variety of crops will allow the manipulation of the same. Manipulation of the β-amyrin pathway will result in changes in the levels or structures of the saponins. A decrease in saponin production will result in an enhancement of plant resistance to pests. Foods originating from plants having an increased level of triterpenes are thought to have a cholesterol lowering effect while decreased triterpenes are believed to result in better tasting foods. Thus, transgenic plants having altered levels of triterpenes may be resistant to pests and foods prepared with seeds having altered levels or structures of saponins will have increased nutritional value or better flavor.

SUMMARY OF THE INVENTION

The instant invention relates to isolated polynucleotides encoding enzymes involved in triterpene synthesis. Specifically, this invention concerns isolated polynucleotides encoding novel cytochrome P450 monooxygenase enzymes of the CYP51 class, designated CYP51H, that modify β-amyrin or β-amyrin derivatives.

The present invention concerns an isolated polynucleotide comprising a nucleotide sequence encoding a CYP51H polypeptide having an amino acid sequence of at least 80% sequence identity, based on the Clustal V method of alignment, when compared to SEQ ID NOs:14 and 26; or a full complement of such polynucleotide.

In a further embodiment, the instant invention is directed to an isolated polynucleotide selected from SEQ ID NOs:5, 13, 19, and 25. The invention also includes the full complement of any of these polynucleotides.

In another embodiment, the instant invention relates to a recombinant DNA construct comprising the isolated polynucleotide of the present invention operably linked to at least one regulatory sequence.

In a further embodiment, the instant invention concerns an isolated host cell comprising the recombinant DNA construct of the present invention. The host cell may be a yeast cell, bacterial cell, or a plant cell.

Compositions, including plants and plant parts, comprising the isolated polypeptide or polynucleotide of the present invention are also embodied by the present invention. The invention also includes transformed plants that arise from transformed host cells of higher plants and seeds or grains derived from such transformed plants. Such transgenic plants include those having an altered level of molecules derived from β-amyrin, or molecules with altered modifications.

The present invention also relates to a method of altering the level of expression of CYP51H polypeptide in a plant cell comprising: transforming plant tissue with a nucleic acid fragment from at least a portion of the isolated polynucleotide of the present invention, wherein the nucleic acid fragment is capable of altering expression of native CYP51H, regenerating the plant tissue into a transgenic plant, and evaluating the transgenic plant for altered level of expression of CYP51H when compared to a plant having wild type level of expression of native CYP51H.

In addition, the present invention relates to a method of producing a plant with altered levels of CYP51H comprising: transforming a plant cell with a recombinant DNA construct of the present invention; growing the transformed plant cell under conditions that promote the regeneration of a whole plant from the transformed cell; wherein the plant regenerated from the transformed cell produces an amount of CYP51H that is greater than the amount of the CYP51H that is produced in a plant that is regenerated from a plant cell of the same species as the plant that is not transformed with the recombinant DNA construct of the present invention; and optionally transforming the plant cell with a second recombinant DNA construct comprising a nucleic acid sequence encoding a polypeptide that regulates expression of at least one enzyme of the triterpene pathway; and growing the transformed plant cell under conditions that promote the regeneration of a whole plant from the transformed cell; wherein the plant regenerated from the transformed cell produces an amount of CYP51H that is greater than the amount of the CYP51H that is produced in a plant that is regenerated from a plant cell of the same species that is not transformed with the recombinant DNA construct and enzyme of the triterpene pathway of the second recombinant DNA construct.

The present invention is also directed to a method of producing a plant resistant to at least one fungus comprising: transforming a plant cell with the recombinant DNA construct of the present invention; growing the transformed plant cell under conditions that promote the regeneration of a whole plant from the transformed cell; wherein the plant regenerated from the transformed cell produces an amount of CYP51H that is greater than the amount of the CYP51H that is produced in a plant that is regenerated from a plant cell of the same species as the plant that is not transformed with the recombinant DNA construct; and optionally transforming the plant cell with a second recombinant DNA construct comprising a nucleic acid sequence encoding a polypeptide that regulates expression of at least one enzyme of the triterpene pathway; and growing the transformed plant cell under conditions that promote the regeneration of a whole plant from the transformed cell; wherein the plant regenerated from the transformed cell produces an amount of CYP51H that is greater than the amount of the CYP51H that is produced in a plant that is regenerated from a plant cell of the same species as the plant that is not transformed with the recombinant DNA construct and said enzyme of the triterpene pathway of said second recombinant DNA construct, thereby producing a plant resistant to fungi.

Also included in the invention are the grains from the transgenic plants of the invention.

BRIEF DESCRIPTION OF THE FIGURES AND SEQUENCE LISTING

The invention can be more fully understood from the following detailed description and the accompanying Sequence Listing which form a part of this application.

The following sequence descriptions and Sequence Listing attached hereto comply with the rules governing nucleotide and/or amino acid sequence disclosures in patent applications as set forth in 37 C.F.R. §1.821-1.825.

FIG. 1 depicts the structures of β-amyrin and Avenacin A-1 highlighting the multiple modifications that must take place to derive the latter from the former.

SEQ ID NO:1 is the nucleotide sequence of the hexaploid oat RFLP probe isu441.

SEQ ID NO:2 is the nucleotide sequence of primer ISU441-GSPF1 used to obtain additional 3' end sequence of the gene cluster for avenacin biosynthesis in *A. strigosa* accession S75 and used for sequencing the genomic fragment encoding AsCyp51H1.

SEQ ID NO:3 is the nucleotide sequence of primer ISU441-GSPF2 used to obtain additional 3' end sequence of the gene cluster for avenacin biosynthesis in *A. strigosa* accession S75.

SEQ ID NO:4 is the nucleotide sequence of primer ISU441-GSPR2 used to amplify the 5' end of the gene cluster for avenacin biosynthesis in *A. strigosa* accession S75.

SEQ ID NO:5 is the nucleotide sequence of the cDNA encoding AsCyp51H1.

SEQ ID NO:6 is the nucleotide sequence of primer ISU441cF01 used in the PCR amplification of the 1639-bp cDNA containing the coding region of the AsCyp51H1 gene, and for sequencing the genomic fragment encoding AsCyp51H1 and the sad2 mutants.

SEQ ID NO:7 is the nucleotide sequence of primer ISU441cR01 used in the PCR amplification of the 1639-bp cDNA containing the coding region of the AsCyp5l H1 gene and the sad2 mutants, and used for sequencing the sad2 mutants.

SEQ ID NO:8 is the nucleotide sequence of primer ISU441gF1 used to sequence pCR®4-TOPO plasmids that might contain the 1639-bp cDNA comprising the coding region of the AsCyp51H1 gene, and used for sequencing the genomic fragment encoding AsCyp51H1 and the sad2 mutants.

SEQ ID NO:9 is the nucleotide sequence of primer ISU441cF03 used for sequencing the genomic fragment encoding AsCyp51H1.

SEQ ID NO:10 is the nucleotide sequence of primer ISU441cF04 used for sequencing the genomic fragment encoding AsCyp51H1.

SEQ ID NO:11 is the nucleotide sequence of primer ISU441gF2 used for sequencing the genomic fragment encoding AsCyp51H1.

SEQ ID NO:12 is the nucleotide sequence of primer ISU441gF4 used for sequencing the genomic fragment encoding AsCyp51H1 and the sad2 mutants.

SEQ ID NO:13 is the nucleotide sequence of the genomic fragment encoding AsCyp51H1.

SEQ ID NO:14 is the amino acid sequence of AsCyp51H1 derived from the cDNA fragment shown in SEQ ID NO:5 or the genomic fragment shown in SEQ ID NO:13.

SEQ ID NO:15 is the nucleotide sequence of primer ISU441pF01 used to amplify the sad2 mutants.

SEQ ID NO:16 is the nucleotide sequence of primer ISU441cR03 used for sequencing the sad2 mutants.

SEQ ID NO:17 is the nucleotide sequence of primer ISU441indeR used for sequencing the sad2 mutants.

SEQ ID NO:18 is the nucleotide sequence of primer ISU441gF5 used for sequencing the sad2 mutants.

SEQ ID NO:19 is the nucleotide sequence of the genomic fragment encoding AsCyp51H2.

SEQ ID NO:20 is the nucleotide sequence of primer ASCYPA2F01.

SEQ ID NO:21 is the nucleotide sequence of primer ASCYPA2R02.

SEQ ID NO:22 is the nucleotide sequence of primer ASCYPA2F03.

SEQ ID NO:23 is the nucleotide sequence of primer ASCYPA2R04.

SEQ ID NO:24 is the nucleotide sequence of primer ASCYPA2F05.

SEQ ID NO:25 is the nucleotide sequence of the cDNA fragment encoding AsCyp51H2.

SEQ ID NO:26 is the amino acid sequence of AsCyp51H2 derived from the genomic fragment shown in SEQ ID NO:19 or the cDNA fragment shown in SEQ ID NO:25.

SEQ ID NO:27 is the nucleotide sequence of the entry Vector for AsCyp51H1 comprising ATTL1-AsCyp51H1-ATTL2.

SEQ ID NO:28 is the nucleotide sequence of the entry Vector for BAS comprising ATTL3-BAS-ATTL4.

SEQ ID NO:29 is the nucleotide sequence of the section between the RB and LB of the maize recombinant DNA construct 1.

SEQ ID NO:30 is the nucleotide sequence of the section between the RB and LB of the maize recombinant DNA construct 2.

SEQ ID NO:31 is the nucleotide sequence of the section between the RB and LB of the soybean recombinant DNA construct 1.

SEQ ID NO:32 is the nucleotide sequence of the section between the RB and LB of the soybean recombinant DNA construct 2.

The Sequence Listing contains the one letter code for nucleotide sequence characters and the three letter codes for amino acids as defined in conformity with the IUPAC-IUBMB standards described in 1984 in the *Biochemical J.* 219:345-373 and in 1985 in *Nucleic Acids Res.* 13:3021-3030 which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucleotide/isolated polynucleotide" and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-nautral or altered nucleotide bases. A polynucleotide in the form of a polymer of DNA may be comprised of one or more segments of cDNA, genomic DNA, synthetic DNA, or mixtures thereof. An isolated polynucleotide of the present invention may include all or part of the isolated polynucleotide, such as for example a polynucleotide comprising the nucleotide sequence selected from the group consisting of SEQ ID NOs:5, 13, 19, and 25, or the full complement of such nucleotide sequences.

The term "isolated" polynucleotide is one that has been substantially separated or purified from other polynucleotides of the organism in which the polynucleotide naturally occurs, i.e., other chromosomal and extrachromosomal DNA and RNA, by conventional nucleic acid purification methods. The term also embraces recombinant polynucleotides and chemically synthesized polynucleotides.

The present invention is directed to isolated polynucleotides encoding CYP51Hs. While not intending to be bound by any theory or theories of operation, it is believed that these enzymes are membrane bound.

As used herein "CYP51H polynucleotides" refers to polynucleotides that encode novel cytochrome P450 monooxygenase enzymes which modify β-amyrin or a β-amyrin derivative in a reaction subsequent to that of β-amyrin synthase. "CYP51H enzymes" refer to the cytochrome P450 enzymes of the invention.

As used herein "cytochrome P450", "P450", "CYP450", and "cytochrome P450 monooxygenase" are used interchangeably herein. These comprise a large number of polypeptides that are grouped into families based solely on sequence homology. Many of the primary modifications to β-amyrin indicated in FIG. 1 are likely to be mediated by cytochrome P450 monooxygenases. These include oxidation at C16, C21, C30, or C23, and epoxidation at C12, C13. Cytochrome P450 monooxygenases are also involved in the biosynthesis of a multitude of other compounds, as described in Nelson D. R., 1999, *Arch. Biochem. Biophys.* 369:1-10. While some single cytochrome P450 monooxygenase enzymes can metabolize multiple substrates, many of these enzymes are highly substrate specific.

Triterpenoid saponins are synthesized via the isoprenoid pathway by cyclization of 2,3-oxidosqualene to give pentacyclic triterpenoids, primarily oleanane (β-amyrin) or dammarane skeletons. The triterpenoid backbone then undergoes various modifications (oxidation, substitution, and glycosylation), mediated by cytochrome P450-dependent monooxygenases, glycosyltransferases, and other enzymes.

Triterpenes, also known as triterpenoids, include and are not limited to sapinogenins and sterols.

As used herein, "substantially similar" refers to polynucleotides having nucleic acid sequences wherein changes in one or more nucleotide bases results in substitution of one or more amino acids, that do not affect the functional properties of the polypeptide encoded by the nucleic acid sequence. "Substantially similar" also refers to polynucleotides wherein changes in one or more nucleotide bases does not affect the ability of the nucleic acid sequence to mediate alteration of gene expression by antisense or co-suppression technology among others. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting polypeptide. It is therefore understood that the invention encompasses more than the specific exemplary sequences.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Sequence alignments and percent identity calculations were performed using the Megalign program of the LASERGENE bioinformatics computing suite (DNASTAR Inc., Madison, Wis.). Multiple alignment of the sequences was performed using the Clustal V method of alignment (Higgins, D. G. et al., 1992, *Comput. Appl. Biosci.* 8(2):189-191) with the default parameters (GAP PENALTY=10, GAP LENGTH PENALTY=10). Default parameters for pairwise alignments using the Clustal V method were KTUPLE 1, GAP PENALTY=3, WINDOW=5 and DIAGONALS SAVED=5.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequence encoding the CYP51H proteins as set forth in SEQ ID NOs:14 and 26. The skilled artisan is well aware of the "codon-bias" exhibited by a specific host cell in usage of nucleotide codons to specify a given amino acid. Therefore, when synthesizing a polynucleotide for improved expression of a specific gene in a host cell, it is desirable to design the polynucleotide such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well-established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences upstream (5' non-coding sequences), within, and downstream (3' non-coding sequences) the coding sequence. "Native gene" refers to a gene as found in nature with its own regulatory sequences, not necessarily in its natural location. "Chimeric or heterologous" "gene or polynucleotide" refers any gene or polynucleotide that is not native to a plant. A chimeric or heterologous gene may comprise regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a polynucleotide capable of controlling the expression of a coding sequence or functional RNA. In general, a coding sequence is located 3' to a promoter sequence. The promoter sequence consists of proximal and more distal upstream elements; the latter elements often referred to as enhancers.

Accordingly, an "enhancer" is a nucleotide sequence, which can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters that cause a gene to be expressed in most cell types at most times are commonly referred to as "constitutive promoters". New promoters of various types useful in plant cells are constantly being discovered; numerous examples may be found in the compilation by Okamuro and Goldberg published in 1989 (Biochem. *Plants* 15:1-82). It is further recognized that since in most cases the exact boundaries of regulatory sequences have not been completely defined, nucleic acid fragments of different lengths may have identical promoter activity.

The "translation leader sequence" or "leader" refers to a polynucleotide sequence located between the promoter of a gene and the coding sequence. The translation leader sequence is present in the fully processed mRNA upstream of the translation start site. The translation leader sequence may affect processing of the primary transcript to mRNA, mRNA stability or translation efficiency. Examples of translation leader sequences have been described (Turner and Foster, 1995, *Mol. Biotechnol.* 3:225-236).

The "3' non-coding region" or "terminator region" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., 1989, *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a DNA that is complementary to and derived from an mRNA. The cDNA can be single-stranded or converted into the double stranded form using, for example, the Klenow fragment of DNA polymerase I. "Sense" RNA refers to RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific gene transcript, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" and "under the control of" refer to the association of nucleic acid fragments on a single polynucleotide so that the function of one is affected by the function of the other. For example, a promoter is operably linked with a coding sequence when it is capable of affecting the expression of that coding sequence (i.e., that the coding sequence is under the transcriptional control of the promoter). Similarly, a polynucleotide may be under the control of a promoter that is capable of affecting the expression of the polynucleotide. Coding sequences can be operably linked to regulatory sequences in sense or antisense orientation.

The term "recombinant DNA construct" means, for example, that a recombinant nucleic acid sequence is made by an artificial combination of two otherwise separated nucleotide segments, e.g., by chemical synthesis or by the manipulation of isolated segments of nucleic acids by genetic engineering techniques.

The term "expression", as used herein refers to the transcription and stable accumulation of sense (mRNA) or antisense RNA derived from a polynucleotide of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference). One can also envision the use of "RNAi" related techniques to reduce the expression of the genes of the present invention. See for example U.S. Pat. No. 6,506,559. Such techniques rely on the use of constructs resulting in the accumulation of double stranded RNA with one strand complementary to the target gene to be silenced.

"Altered levels" or "altered expression" refers to the production of gene product(s) in transgenic organisms in amounts or proportions that differ from that of normal or non-transformed organisms. Altered levels include an increase and a decrease in gene product amounts compared to normal or non-transformed organisms. Accordingly, altered includes increase, enhance, amplify, multiply, elevate, raise, and the like as well as decrease, reduce, lower, prevent, inhibit, stop, eliminate, and the like.

"Mature" protein refers to a post-translationally processed polypeptide; i.e., one from which any pre- or pro-peptides present in the primary translation product has been removed. "Precursor" protein refers to the primary product of translation of mRNA; i.e., with pre- and pro-peptides still present. Pre- and pro-peptides may be but are not limited to intracellular localization signals.

A "signal peptide" is an amino acid sequence that is translated in conjunction with a protein and directs the protein to the secretory system (Chrispeels, M. (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel, N. (1992) *Plant Phys.* 100:1627-1632). A "chloroplast transit peptide" is an amino acid sequence that is translated in conjunction with a protein and directs the protein to the chloroplast or other plastid types present in the cell in which the protein is made. "Chloroplast transit sequence" refers to a nucleotide sequence that encodes a chloroplast transit peptide.

"Transformation" refers to the transfer of a nucleic acid fragment into the genome of a host organism, resulting in genetically stable inheritance. Host organisms containing the transformed nucleic acid fragments are referred to as "transgenic" organisms. "Host cell" refers the cell into which transformation of the recombinant DNA construct takes place and may include a yeast cell, a bacterial cell, and a plant cell. Examples of methods of plant transformation include Agrobacterium-mediated transformation (De Blaere et al., 1987, *Meth. Enzymol.* 143:277) and particle-accelerated or "gene gun" transformation technology (Klein et al., 1987, *Nature (London)* 327:70-73; U.S. Pat. No. 4,945,050), among others.

Expression of a chimeric CYP51H, for example, results in the production of a level of the encoded CYP51H protein in a transformed host cell that is altered as compared to the level produced in an untransformed host cell. Also, a transgenic plant, or plant part, comprising a polynucleotide of the present invention, such as for example, SEQ ID NOs:5, 13, 19, and 25, under the control of a heterologous promoter results in plants having altered levels of triterpenes. Plants may be selected from the group consisting of monocots and dicots. Monocots include and are not limited to corn, oat, rice, wheat, barley, palm, and the like. Dicots include and are not limited to *Arabidopsis*, soybean, oilseed Brassica, peanut, sunflower, safflower, cotton, tobacco, tomato, potato, cocoa, and the like. Plant parts include and are not limited to seeds and grains, for example.

Thus, isolated polynucleotides of the present invention can be incorporated into recombinant constructs capable of introduction into and replication in a host cell. A "vector" may be such a construct that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. Molecular Cloning: A Laboratory Manual; Cold Spring Harbor Laboratory Press: Cold Spring Harbor, 1989 (hereinafter "Sambrook").

"PCR" or "polymerase chain reaction" is a technique for the synthesis of large quantities of specific DNA segments. It consists of a series of repetitive cycles (Perkin Elmer Cetus Instruments, Norwark, Conn.). Typically, the double-stranded DNA is heat denatured, the two primers complementary to the 3' boundaries of the target segments are annealed at low temperature and then extended at an intermediate temperature. One set of these three consecutive steps is referred to as a cycle.

Oats having a sad2 mutation produce β-amyrin but produce very little or no avenacins. Eight mutations conferring a sad2 phenotype have been identified. Each of these has a lesion in the polynucleotide of the present invention that would render the polynucleotide incapable of expressing a functional mRNA encoding a functional protein. These data together with the biochemical data presented herein indicate that the non-mutated polynucleotide of the present invention encodes the enzyme AsCyp51H1 (also known in some portions of the literature as CYP51H10) responsible for a modification of β-amyrin or a β-amyrin derivative, which is not carried out in the sad2 mutants. Genomic and cDNA fragments encoding AsCyp51H1 are disclosed. Also identified is an AsCyp51H1 homolog AsCyp51H2 (also known in some portions of the literature as CYP51H11). The nucleotide sequence of AsCyp51H2 hybridizes to a probe prepared with the genomic sequence that encodes AsCyp51H1.

The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other CYP51Hs, either as cDNAs or genomic DNAs, may be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Sambrook). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full-length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., 1988, *Proc. Natl. Acad. Sci. U.S.A.* 85:8998-9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., 1989, *Proc. Natl. Acad. Sci. U.S.A* 86:5673-5677; Loh et al., 1989, *Science* 243:217-220). Products generated by the 3' and 5' RACE procedures can be combined to generate full-length cDNAs (Frohman and Martin, 1989, *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner,1984, *Adv. Immunol.* 36:1-34; Sambrook).

The nucleic acid fragments of the instant invention may be used to create transgenic plants in which CYP51Hs of the present invention are present at higher levels than normal or in cell types or developmental stages in which they are not normally found. This would have the effect of altering production of triterpenes in those cells. It is believed that overexpression of the polynucleotides of the invention, optionally in combination with polynucleotides encoding enzymes responsible for other steps in the saponin biosynthetic pathway, enhances resistance to at least one fungus. Suppression of the polynucleotides of the invention may result in legumes producing lower saponins, which in turn may improve the flavor.

A "plant resistant to at least one fungus" refers to a plant comprising a recombinant DNA construct of the present invention which when infected with a fungus is able to resist infection or to tolerate infection to a greater degree, resulting in less damage, more vigorous health and less or no loss of yield due to fungal infection relative to plants without the recombinant DNA construct of the present invention. The fungus is typically pathogenic. "Pathogenic" or "fungal pathogen" refer to a fungus that under conditions that do not include the recombinant DNA construct of the present invention, would cause disease in a plant. A transgenic plant comprising the recombinant DNA construct of the present invention is typically a plant more resistant to at least one fungus than a plant of the same species without the recombinant DNA construct of the present invention.

The embodiments of the present invention may be effective against a variety of plant fungal pathogens. Some specific fungal pathogens for the major crops include, but are not limited to, the following: Soybeans: *Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Colletotrichum dematium* (*Colletotichum truncatum*), *Corynespora cassiicola, Septoria glycines, Phyllosticta sojicola, Alternaria alternata, Microsphaera diffusa, Fusarium semitectum, Phialophora gregata, Glomerella glycines, Phakopsora pachyrhizi, Fusarium solani*; Canola: *Alternaria brassicae, Leptosphaeria maculans, Rhizoctonia solani, Sclerotinia sclerotiorum, Mycosphaerella brassicicola, Fusarium roseum, Alternaria alternata*; Alfalfa: *Phoma medicaginis* var. *medicaginis, Cercospora medicaginis, Pseudopeziza medicaginis, Leptotrichila medicaginis, Fusarium oxysporum, Verticillium albo-atrum, Stemphylium herbarum, Stemphylium alfalfae, Colletotrichum trifolii, Leptosphaerulina briosiana, Uromyces striatus, Sclerotinia trifoliorum, Stagonospora meliloti, Stemphylium botryosum, Leptotrochila medicaginis*; Wheat: *Urocystis agropyri, Alternaria aternata, Cladosporium herbarum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondite* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Bipolaris sorokiniana, Claviceps purpurea, Tilletia tritici, Tilletia laevis, Ustilago tritici, Tilletia indica, Rhizoctonia solani*; Sunflower: *Plasmophora halstedii, Sclerotinia sclerotiorum, Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Cephalosporium acremonium*; Corn: *Colletotrichum graminicola* (*Glomerella graminicola*), *Stenocarpella maydi* (*Diplodia maydis*), *Fusarium moniliforme* var. *subglutinans, Fusarium verticillioides, Gibberella zeae* (*Fusarium graminearum*), *Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Trichoderma viride, Claviceps sorghi, Diplodia macrospora, Sclerophthora macrospora, Sphacelotheca reiliana, Physopella zeae, Cephalosporium maydis, Cephalosporium acremonium*; Sorghum: *Exserohilum turcicum, Cercospora sorghi, Gloeocercospora sorghi, Ascochyta sorghina, Puccinia purpurea, Macrophomina phaseolina, Perconia circinata, Fusarium moniliforme, Alternaria alternata, Bipolaris sorghicola, Helminthosporium sorghicola, Curvularia lunata, Phoma insidiosa, Ramulispora sorghi, Ramulispora sorghicola, Phyllachara sacchari, Sporisorium reilianum* (*Sphacelotheca reiliana*), *Sphacelotheca cruenta, Sporisorium sorghi, Claviceps sorghi, Rhizoctonia solani, Acremonium strictum,* Colletotrichum (*Glomerella*) *graminicola* (*C. sublineolum*), *Fusarium graminearum, Fusarium oxysporum*; and the like.

Overexpression of CYP51H proteins of the instant invention may be accomplished by first constructing a recombinant DNA construct in which the coding region is operably linked to a promoter capable of directing expression of CYP51H in the desired tissues at the desired stage of development. The recombinant DNA construct may comprise promoter sequences and translation leader sequences derived from the same genes. 3' non-coding sequences encoding transcription termination signals may also be provided. The instant recombinant DNA construct may also comprise one or more introns in order to facilitate gene expression.

Plasmid vectors comprising the isolated polynucleotide of the invention may be constructed. The choice of plasmid vector is dependent upon the method that will be used to transform host cells. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., 1985, *EMBO J.* 4:2411-2418; De Almeida et al., 1989, *Mol. Gen. Genetics* 218:78-86), and thus that multiple events may have to be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate their secretion from the cell. It is thus envisioned that the recombinant DNA constructs described above may be further supplemented by altering the coding sequence to encode appropriate intracellular targeting signals such as transit signals (Keegstra, 1989, *Cell* 56:247-253), signal sequences with or without endoplasmic reticulum retention signals (Chrispeels, 1991, *Ann. Rev. Plant Phys. Plant Mol. Biol.* 42:21-53), or nuclear localization signals (Raikhel, N., 1992, *Plant Phys.* 100:1627-1632) with or without removing targeting signals that are already present. While the references cited give examples of each of these, the list is not exhaustive and more targeting signals of utility may be discovered in the future.

It may also be desirable to reduce or eliminate expression of CYP51H in plants for some applications. In order to accomplish this, a recombinant DNA construct designed for co-suppression of such enzymes can be constructed by linking a polynucleotide encoding an CYP51H to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated. Construction of chimeric nucleic acid fragments that result in the formation of hair-loop structures where portions of the polynucleotides of the invention are either the stem or the loop or the structure may also be prepared. It may also be possible to use small fragments of the nucleotides encoding CYP51H to prepare constructs that would serve as RNAi to suppress its expression. Any of the recombinant DNA constructs mentioned above may be introduced into a cell to eliminate expression of CYP51H in plants.

A variety of nucleic acid amplification-based methods of genetic and physical mapping may be carried out using the instant nucleic acid sequences. Examples include, and are not limited to, allele-specific amplification (Kazazian, H. H. jr, 1989, *J. Lab. Clin. Med.* 11:95-96), polymorphism of PCR-amplified fragments (CAPS; Sheffield, V. C., et al., 1993, *Genomics* 16:325-332), allele-specific ligation (Landegren, U., et al., 1988, *Science* 241:1077-1080), nucleotide extension reactions (Sokolov, B. P., 1990, *Nucleic Acid Res.* 18:3671), radiation hybrid mapping (Walter, M. A. et al., 1994, *Nat. Genet.* 7:22-28), fluorescence in situ hybridization (FISH; Svitashev, S. K. and Somers, D. A., 2002, *Plant Cell Tissue Organ Cult.* 69:205-214), and Happy Mapping (Dear, P. H. and Cook, P. R., 1989, Nucleic Acid Res. 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for all mapping methods.

While not intending to be bound by any theory or theories of operation, it is believed by those of skill in the art that altered levels of triterpenes have different effects. Increased levels of triterpenes such as avenacin in parts of the plant normally susceptible to fungal pathogen infection may endow the plant with resistance to at least some such pathogens, protecting the plants and so enhancing yield in circumstances of fungal pressure. Foods originating from plants having an increased level of triterpenes are thought to have a cholesterol lowering effect while decreased triterpenes are believed to result in better tasting foods. Accordingly, plants grown with altered levels of CYP51H may contribute to nutritious and/or better-flavored foods. Thus, also included in the invention are the grains from the transgenic plants of the invention.

The present invention is further defined in the following Examples, in which all parts and percentages are by weight and degrees are Celsius, unless otherwise stated. Examples 1-4 are actual, Examples 5-7 are prophetic. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated by reference in its entirety.

EXAMPLE 1

Generation of Mutants and Biochemical Characterization of sad2 Oat Mutants

Seed of the diploid oat species *Avena strigosa* were mutagenized with sodium azide and M2 seed from individual M1 plants were germinated and assessed for root fluorescence as a preliminary screen to identify saponin-deficient, or sad, oat mutants. Seedlings not producing avenacins were identified by HPLC and TLC analyses of methanolic root extracts from homozygous M3 seedlings of putative mutants.

Generation of Mutants

Seed of the diploid oat species *Avena strigosa* (accession S75 from the Institute of Grasslands and Environmental Research, Aberystwyth, Wales, UK) was mutagenized with sodium azide essentially as described (Rines, H. W., 1985, *Env. Exp. Bot.*, 25:7-17). Briefly, mutagenesis was performed as follows. Seeds were presoaked in an Erlenmeyer flask sealed with a rubber stopper using 0.5 ml water per seed while shaking in an orbital platform shaker at 120 cycles per minute. After presoaking for 4 hours the water was decanted. A solution of 10 mM sodium azide in 0.1 M sodium phosphate, pH 3.2 was prepared and immediately added to the seeds. After shaking, as above, for 1 hour the mutagen solution was decanted and the seeds rinsed with 5 to 6 changes of water with the last three water rinses extending over a period of 30 minutes. Rinsed seeds were drained and spread over paper in a fume hood to dry. M2 seed from individual M1 plants were germinated and assessed for root fluorescence as indicated below.

The major oat-root saponin avenacin A-1 contains N-methyl anthranilic acid and, thus, is primarily responsible for the bright blue fluorescence of young oat roots (Osbourn A. E. et al., 1994, *Physiol. Mol. Plant Pathol.* 45:457-467). The fact that avenacin A-1 is detectable by UV light allows root fluorescence to be used as a preliminary screen to identify saponin-deficient (sad) oat mutants. Seed of individual M2 families were germinated and assessed for root fluorescence. In the initial screens ten independent mutants with reduced fluorescence were identified after screening seedlings representing 1,289 M2 families as reported by Papadopoulou K. et al. (1999, *Proc. Natl. Acad. Sci. U.S.A.* 96:12923-1928). Subsequent mutant screens identified a further 40 independent avenacin-deficient mutants isolated on the basis of reduced root fluorescence.

Biochemical Characterization

Analysis of the root extracts of the original ten mutants was carried out as described (Papadopoulou K. et al., 1999, *Proc. Natl. Acad. Sci. U.S.A.* 96:12923-1928). Briefly, M3 seeds were germinated on moist filter paper for 2 days and terminal 0.5 cm sections of the roots from 20 seedlings per line were harvested and extracted in methanol. For HPLC analysis crude methanolic root extracts from M3 seedlings were prepared in triplicate and 100 µl aliquots were analyzed directly on a Hichrom Nucleosil 5 C18 reverse phase column (4.5×250 mm) under isocratic conditions in 75% methanol (flow rate 1 ml/min) with detection at 225 nm. The four avenacins were quantified by comparison of peak areas with those of standards of known concentration. Extracts for TLC analysis were dried down, resuspended in 1 ml water and applied to SepPak C18 reverse phase cartridges (Waters, Milford, Mass.) that had been pre-conditioned with 10 ml of methanol followed by 10 ml distilled water. After elution with 75% methanol samples were dried down, resuspended in 15 µl of 100% methanol, applied to the TLC plates, and separated using chloroform:methanol:water (13:6:1; v:v:v). Avenacins A-1 and B-1 and other fluorescent components were visualized under UV illumination at 302 nm. The TLC plate was then sprayed with p-anisaldehyde/sulphuric acid/acetic acid (1:1:48, v:v:v) and baked at 130° C. for 5 min to detect all four saponins. Root extracts derived from either M3 or F3 seedlings were compared on at least seven occasions with essentially the same outcome.

HPLC analysis of crude root extracts confirmed the absence of all four avenacins in mutant #1027; and reduced levels of avenacins (approximately 15% of that of the wild type) in extracts from mutant #791 (Papadopoulou K. et al., 1999, *Proc. Natl. Acad. Sci. U.S.A.* 96:12923-1928).

Genetic Analysis of sad Mutants

Test crosses were performed between the sad mutants and the wild type *A. strigosa* to determine if the saponin-deficient phenotype was due to a single mutation. Analysis of F2 generations from intermutant crosses identified at least 4 complementation groups in the initial 10 mutant lines. These loci were designated sad1 through sad4 (Papadopoulou K. et al., 1999, *Proc. Natl. Acad. Sci. U.S.A.* 96:12923-1928). Further analysis of the original 10 mutant lines determined 4 additional loci designated sad5 through sad8 (Qi X. et al., 2004, *Proc. Natl. Acad. Sci. U.S.A.* 101:8233-8238). Additional loci sad9 and sad10 were identified while analyzing the additional 40 mutant lines identified later. The sad2 locus was identified as a single dominant locus defined by independent mutants #791 and #1027 (Papadopoulou K. et al., 1999, *Proc. Natl. Acad. Sci. U.S.A.* 96:12923-1928).

Subsequent feeding experiments using radiolabled mevalonic acid (R-[2-$^{14}$C] MVA) on mutant roots indicated that sad2 mutants incorporated radioactivity into β-amyrin but either produced very small amounts of avenacins or not at all suggesting that they are blocked in a step early in the avenacin biosynthetic pathway (Trojanowska M. R. et al., 2001, *Phytochemistry* 56:121-129). Of the original 10 sad mutants the sad2 mutants were the only ones that accumulate β-amyrin. Screening of root extracts of the additional 40 mutant lines led to the identification of a further six candidate sad2-like mutants (mutants #283, #500, #638, #698, #1325 and #1412) on the basis of metabolite profiling experiments performed as described below.

A single seed of each line was soaked in 1% bleach for 10 minutes, rinsed three times with sterile distilled water, kept at 4° C. for approximately 24 hours, and then germinated on 1% agar at 22° C. for 6 days. Individual roots were harvested, freeze-dried, ground in liquid nitrogen, and extracted with methanol. Extracts were centrifuged, the supernatant removed and dried down prior to extraction with 100 µl CHCl$_3$/MeOH (7:3, v/v). Extracts were then spotted onto TLC plates together with a β-amyrin standard dissolved in chloroform. The TLC plates were developed with hexane:acetone (80:20, v/v). Iodine vapor was used to detect β-amyrin and other compounds.

Using this screen a further six candidate sad2-like mutants were identified that accumulate elevated levels of β-amyrin. These results were confirmed by quantitative GC/MS analysis as described below.

TMS Ether Derivatization and GC-MS Analysis.

To 50 µl of each sample extract prepared as above from sad mutants and wild type roots 100 µl of Tri-Sil reagent and 24.48 µg of 5β-cholestan-3β-ol (TMS) was added in glass-stoppered small clear reaction vials. After swirling to dissolve the samples, the vials were heated at 60° C. for 60 minutes. Excess reagent and solvent were removed under a nitrogen stream, and normally the residue was diluted to 200 µl with HPLC grade hexane for quantitation by gas chromatography (GC) with flame ionization detection (FID).

Gas chromatography-mass spectrometry (GC-MS) was carried out on a Hewlett Packard 5973 mass selective detector coupled to a Hewlett Packard 6890 gas chromatograph with a Hewlett Packard 6890 auto injector. The column was a 30 m long DB-5MS (J & W scientific Ltd, United Kingdom) with a 0.25 mm internal diameter and a film thickness of 0.25 micron. It was held for 1 minute at 250° C., then programmed to increase at 5° C./minute to 325° C., and held for 10 minutes at 325° C. The injector was set at 250° C. and a 2 µl injection volume was used. The flow was set at 3 psi and operated in split mode with a split ratio of 10:1. The mass spectrometer source was set at 230° C. and the quadrupole at 106° C. The mass spectrometer was scanned between masses 35 and 800 in 1 second for full scan spectra after a 5 minute solvent delay. Selected ion recording masses of 498.4, 218.2, 203.2, 460.4, 370.4 and 355.3 were sequentially monitored with a dwell setting of 30 (3.64 cycles/second) between 8 and 20 minutes.

Quantitation of β-amyrin was performed using 5β-Cholestan-3β-ol (TMS) as internal standard and preparing a calibration line by analyzing a fixed amount of internal standard against a varying amount of β-amyrin. The area of the 370 ion was used for the internal standard and the area of the 218 ion used for β-amyrin. The results in Table 1, below, clearly demonstrate that sad2 mutants 791 and 1027 have much larger amounts of β-amyrin than sad1 mutants or wild type plants. Table 1 presents the quantity of β-amyrin obtained from GC-MS analyses of S75 (wt), 610 and 109 (sad1), and 791 and 1027 (sad2) roots. The results are presented as the mean β-amyrin content or µg/g of fresh freeze-dried root ± the standard deviation. Two independent extractions were done for each root except, for the sad1 mutant 610.

TABLE 1

Quantity of β-amyrin in sad1, sad2, and wt Roots

| Sample | Mean β-amyrin Content |
|---|---|
| 791 | 48.5 ± 9.0 |
| 791 | 38.7 ± 3.2 |
| 1027 | 42.4 ± 5.4 |
| 1027 | 47.7 ± 4.7 |
| S75 | 2.7 ± 0.2 |
| S75 | 2.0 ± 0.0 |
| 610 | 0.7 ± 0.0 |
| 109 | 0.8 ± 0.0 |
| 109 | 0.8 ± 0.0 |

These results suggest that the sad2 mutations affect a step downstream of β-amyrin synthase.

EXAMPLE 2

Isolation of the AsCypH1 Genomic and cDNA Fragments

The genomic polynucleotide fragment encoding the gene affected in sad2 mutants was isolated from *A. strigosa* accession S75 genomic DNA and from a library prepared from oat as follows.

The genomic polynucleotide fragment present in *A. strigosa* accession S75 and affected by the sad2 mutations was identified from a gene cluster identified for avenacin biosynthesis (Qi X. et al., 2004, *Proc. Natl. Acad. Sci. U.S.A.* 101:8233-8238). First, the hexaploid oat RFLP probe isu441 (Rayapati, P. J., et al., 1994, *Theor. Appl. Genet.* 89:831-837) previously mapped to the gene cluster for avenacin biosynthesis in diploid oat (Qi X. et al., 2004, *Proc. Natl. Acad. Sci. U.S.A.* 101:8233-8238) was used. Probe isu441 (which is a cDNA-derived probe) was sequenced by using the ABI PRISM® Big-Dye™ Terminator Cycle Sequencing Ready Reaction Kit (Applied Biosystems) with M13 forward and reverse primers (Qiagen Ltd) and its nucleotide sequence is shown in SEQ ID NO:1. The resulting 480-nt fragment was found to share sequence similarity with obtusifoliol 14α-demethylases, sterol biosynthetic enzymes belonging to the CYP51 family of P450s. The fragment lies in the 3' region of the predicted P450 coding sequence and includes the polyA tail. Further sequence was obtained towards the 3'-end of the gene using the GenomeWalker™ kit following instructions provided by the manufacturer (Clontech Ltd) and DNA from *A. strigosa* accession S75 as the template. Two primers, ISU441-GSPF1 and ISU441-GSPF2 were used in this experiment. The nucleotide sequences of these primers are shown in SEQ ID NOs:2 and 3, respectively.

ISU441-GSPF1:
5'-CTGACTTCTCCATTTCCCAAGCAAGA-3'    (SEQ ID NO:2)

ISU441-GSPF2:
5'-CTACTAGCACCTATTTGCACGGATGT-3'    (SEQ ID NO:3)

The 5'-end cDNA fragment was obtained by using GeneRacer™ Kit following instructions provided by the manufacturer (Invitrogen Ltd). Total RNA was isolated from the root tips of S75. A PCR fragment of around 1.3 kb was amplified from RACE-ready cDNA using the GeneRacer™ 5' Primer and ISU441-GSPR2 (shown in SEQ ID NO:4), which is an isu441-specific primer.

ISU441-GSPR2:
5'-ATCCTCCTCTCTTCCAACACGAAACC-3'    (SEQ ID NO:4)

This 1.3-kb PCR fragment was cloned into PCR-Script Amp SK (+) plasmid by following the protocol for the PCR-Script™ Amp Electroporation-Competent cell Cloning Kit provided by the manufacturer (Stratagene Ltd). Sequencing was conducted by using the ABI PRISM® Big-Dye™ Terminator Cycle Sequencing Ready Reaction Kit (Applied Biosystems) with M13 forward and reverse primers (Qiagen Ltd). By merging the 5'-end and 3'-end sequences a sequence corresponding to an approximately 1790 bp fragment derived from isu441 was obtained from S75 and is shown in SEQ ID NO:5. This cDNA contains an entire open reading frame corresponding to nucleotides 103-1572. The gene corresponding to this cDNA was designated AsCyp51H1. The 1639-bp cDNA containing the coding region of this gene was amplified by PCR with primer pair ISU441cF01 and ISU441cR01 (shown in SEQ ID NOs:6 and 7, respectively), and cloned into pCR®4-TOPO plasmid (Invitrogen Ltd).

ISU441cF01
5'-CCAGTCAGGAGGATTTCAAATTCGTATTCA-3'    (SEQ ID NO:6)

ISU441cR01
5'-CGACGCCTTATTGTAAATAAGCCCAT-3'    (SEQ ID NO:7)

Plasmids from 8 positive clones were sequenced with M13 forward and reverse primers (Qiagen Ltd), and primer ISU441gF1 (shown in SEQ ID NO:8), respectively. A mutation-free clone was identified (pCR®4-TOPO:isu441c-7) and was used for further experiments.

ISU441gF1
5'-ACGAGGGTGAAGTCGATCTGAAACAAGAG-3'    (SEQ ID NO:8)

The genomic DNA fragment of the AsCyp51H1 gene was amplified from *A. strigosa* accession S75 genomic DNA by PCR using oligonucleotide primers ISU441cF01 and ISU441cR01 (mentioned above) using Expand High Fidelity PCR System (Roche Molecular Biochemicals). The 50 µl PCR reaction contained 100 ng genomic DNA, 0.2 µM forward primer, 0.2 µM reverse primer, 200 µM dNTPs, 1× reaction buffer with 1.5 mM $MgCl_2$, and 2.6 U of Expand High Fidelity PCR System Enzyme Mix. After initial denaturation at 94° C. for 2 minutes, amplification was carried out with 35 cycles of 1) denaturation at 94° C. for 30 seconds, 2) annealing at 63° C. for 30 seconds, and 3) extension at 68° C. for 4 minutes. The amplified product was purified using a Qiagen PCR Purification Kit (Qiagen Ltd) and then used for direct sequencing with primers ISU441cF01, ISU441cF03, ISU441cF04, ISU441gF1, ISU441gF2 and ISU441-GSPF1 (the nucleotide sequences of which are shown in SEQ ID NOs:6, 9, 10, 8, 11, and 2, respectively).

ISU441cF03
5'-CAATTATATCCATCGCTGCAGTAG-3'    (SEQ ID NO:9)

ISU441cF04
5'-ATGTTGATCTCATTCGACAGGAAGT-3'    (SEQ ID NO:10)

-continued

ISU441gF2
5'-TGTCGAGGAGCAAAAGCAAATGATGAG-3'    (SEQ ID NO:11)

ISU441gF4:
5'-GAACAAGTGCGATGGATTATGGTA-3'    (SEQ ID NO:12)

Oligonucleotide primer ISU441gF4 (the nucleotide sequence of which is shown in SEQ ID NO:12) was designed and used for sequencing through the remaining gap to produce an entire genomic sequence encoding AsCyp51H. Comparison of the genomic DNA sequence with that obtained for the full-length cDNA identified two introns. The cDNA sequence starts at nucleotide 2881 of the genomic sequence. There is a 348-nucleotide intron at nucleotide 77 of the cDNA sequence and a 973-nucleotide intron at nucleotide 576 of the cDNA sequence.

To extend the sequence towards the 5' end in order to obtain a possible promoter sequence a BAC library derived from *A. strigosa* accession S75 genomic DNA was screened with a probe generated from plasmid pCR®4-TOPO: isu441c-7. For this purpose a 1639-bp cDNA probe was generated from plasmid DNA of clone pCR®4-TOPO: isu441c-7 (containing AsCyp51H1 cDNA and described above) by PCR with the primer pair ISU441cF01 and ISU441cR01 (shown in SEQ ID NOs:6 and 7). A BAC library was constructed as described by Bakht et. al. (Plant & Animal Genome XI Conference, Jan. 11-15, 2003, San Diego, Calif., P82) and was screened with this probe. Shotgun sequencing of one of the positive clones (clone #B460D15) yielded a further 2882 bp of sequence upstream from 5'-end of the full-length cDNA. This region was defined as putative promoter sequence of AsCyp51H1 gene. The 5992 bp genomic sequence of the AsCyp51H gene is shown in SEQ ID NO:13. The amino acid sequence of the enzyme encoded by this gene has 490 amino acids and are shown in SEQ ID NO:14.

EXAMPLE 3

Cloning and Sequencing of AsCyp51H1 Alleles From Different sad2 Mutants

The sad2 mutants #791 and #1027 accumulate β-amyrin and so were considered likely to be blocked in a cytochrome P450-mediated step early in the pathway. Previous genetic analysis (Qi X. et al., 2004, *Proc. Natl. Acad. Sci. U.S.A.* 101:8233-8238) indicated that Sad2 is closely linked to Sad1. This gene, Sad1, has been designated AsbAS1 and has been previously cloned, characterized, and demonstrated to encode β-amyrin synthase, the enzyme that catalyzes the first committed step in avenacin biosynthesis (Haralampidis K. et al., 2001, *Proc. Natl. Acad. Sci. U.S.A.* 98:13431-13436). Sad2 co-segregates with Sad1 in a population of 2040 F2 individuals (Qi X. at al., 2004, *Proc. Natl. Acad. Sci. U.S.A.* 101:8233-8238). Several BAC clones that contained both AsCyp51H1 and AsbAS1 were identified by hybridization of the BAC colony filters with the cDNA probes from the two genes. Analysis of the sequence of one of these clones (clone #B460D15) indicated that AsCyp51H1 was within 100 kb of AsbAS1. AsCyp51H1 had been predicted to encode a cytochrome P450 enzyme and was known to be genetically linked to Sad1 therefore it was a candidate for Sad2. This was addressed by sequencing the AsCyp51H1 gene in the two original sad2 mutants (#791 and #1027) and in the new sad2-like mutants identified by metabolite profiling.

Genomic DNA from S75, the confirmed sad2 mutants #791, #1027 and the six candidate sad2-like mutants #283, #500, #638, #698, #1325 and #1412 were amplified by PCR with the primer pair ISU441pF01 (shown in SEQ ID NO:15) and ISU441cR01 (shown in SEQ ID NO:7).

ISU441pF01:
5'-CGTGGCTTTTTTCCATTTCTCC-3'    (SEQ ID NO:15)

The PCR products were purified using Qiagen PCR Purification Kit (Qiagen Ltd) and used for direct sequencing with primers ISU441pF01, ISU441cR03, ISU441indeR, isu441gF5, ISU441gF4, ISU441gF1, ISU441gF2, and ISU441cR01 (shown in SEQ ID NOs:15, 16, 17, 18, 12, 8, 11, and 7, respectively).

ISU441cR03:
5'-GAGATCAATTCCTGTCACCACC-3'    (SEQ ID NO:16)

ISU441indeR:
5'-GCACACTAACATTTTCTATATCGTTTC A-3'    (SEQ ID NO:17)

ISU441gF5:
5'-TACTATGTGAATATAAGTAATGTT-3'    (SEQ ID NO:18)

Sequencing was carried out using the ABI PRISM® Big-Dye™ Terminator Cycle Sequencing Ready Reaction Kit (Applied Biosystems). Point mutations were found in all the sad2 and sad2-like mutants. In the original sad2 mutants #791 and #1027 and in five of the six sad2-like mutants these mutations were found to be in the coding region of the AsCyp51H1 gene and are predicted to cause amino acid substitutions as follows. In mutant #1412 nucleotide 338 was thymine instead of cytosine resulting in amino acid 113 being changed from threonine to isoleucine. In mutant #1027 nucleotide 371 was thymine instead of cytosine to resulting in amino acid 124 being changed from alanine to valine. In mutant #698 nucleotide 1670 was adenine instead of guanine resulting in amino acid 233 being changed from alanine to threonine. In mutant #1325 nucleotide 1866 was thymine instead of cytosine resulting in amino acid 298 being changed from serine to phenylalanine. In mutant #638 nucleotide 1922 was adenine instead of guanine resulting in amino acid 317 being changed from glutamic acid to lysine. In mutant #283 nucleotide 2277 was adenine instead of guanine resulting in amino acid 435 being changed from glycine to aspartic acid. In mutant #791 nucleotide 2360 was thymine instead of cytosine resulting in amino acid 463 being changed from proline to serine. In mutant #500 the mutation was at the exon-intron boundary having adenine at nucleotide 475 instead of guanine resulting in a longer exon.

One would expect that mutations causing amino acid substitutions would not effect transcription, but mutations that disrupt splicing might result in an unstable message. Northern blot analysis of transcripts from the sad2 mutants was consistent with this. Mutant #500 lacks AsCyp51H1 transcript while the other mutants still possess transcripts corresponding to AsCyp51H1.

In summary, multiple independent alleles of the sad2 mutant were isolated. All accumulate β-amyrin and either lack or produce reduced levels of avenacins. Each mutant has a copy of the AsCyp51H1 gene containing a molecular lesion that would be expected to encode a non-functional enzyme or an unstable transcript. Taken together these data indicate that Sad2 is synonymous with AsCyp51H1, which encodes an enzyme catalyzing a step subsequent to that carried out by β-amyrin synthase in the biosynthetic pathway for avenacins.

EXAMPLE 4

Cloning of AsCyp51H2

Other P450s that may be involved in the modification of β-amyrin may be found by sequencing DNA that hybridizes with probes prepared from AsCyp51H1. For this purpose a BAC clone that showed a positive reaction when hybridizing with AsCyp51H1 cDNA as a probe was sequenced and analyzed as follows.

Shotgun sequencing analysis of a BAC clone (clone# B286H18) which showed a positive reaction when using AsCyp51H1 cDNA as probe revealed some fragments with sequence similarity to AsCyp51H1 (74% sequence identity at the nucleic acid level). Comparison of the genomic AsCyp51H1 sequence with the newly obtained BAC sequences enabled the identification of a putative homologous gene. This putative homologous gene contains a 3-kb promoter region, three exons, and two introns, was designated AsCyp51H2, and its nucleotide sequence is shown in SEQ ID NO:19.

The tissue distribution of AsCyp51H2 was analyzed by PCR amplification of total RNA isolated from the root tips, shoots, old leaves, and flowers of S75. RT-PCR amplification using primer pair ASCYPA2F01 and ASCYPA2R02 (shown in SEQ ID NOs:20 and 21, respectively) revealed that AsCyp51H2 only expresses in oat flowers.

```
ASCYPA2F01
5'-CAGTTAGCGTCATGTTGTTCTC-3'      (SEQ ID NO:20)

ASCYPA2R02
5'GAACACGCTAAAGGCTTGCAT-3'        (SEQ ID NO:21)
```

The cDNA fragment containing the coding sequence for AsCyp51H2 was obtained by PCR amplification of total RNA with primer pair ASCYPA2F03 and ASCYPA2R04 (shown in SEQ ID NOs:22 and 23, respectively).

```
ASCYPA2F03
5'-GCTTCCCTGAGAACTACACCATGG-3'    (SEQ ID NO:22)

ASCYPA2R04
5'-ATCAACCACACCTTCTTCCTCC-3'      (SEQ ID NO:23)
```

The amplified PCR fragment was cloned into pCR®4-TOPO (Invitrogen Ltd). Plasmids from 7 positive clones were sequenced with M13 forward and reverse primers (Qiagen Ltd), and primer ASCYPA2F05 (shown in SEQ ID NO:24), respectively.

```
ASCYPA2F05
5'-AGCATACCCGCTTCATCGTTG-3'       (SEQ ID NO:24)
```

Sequencing was carried out using the ABI PRISM® Big-Dye™ Terminator Cycle Sequencing Ready Reaction Kit (Applied Biosystems). A mutation-free clone was identified and designated pCR®4-TOPO:AsCypA2. The nucleotide sequence of the cDNA insert in this clone is shown in SEQ ID NO:25. The deduced amino acid sequence of nucleotides 18 through 1487 of SEQ ID NO:25 are shown in SEQ ID NO:26. Nucleotides 1488-1490 represent a stop codon.

EXAMPLE 5

Recombinant DNA Constructs to Express AsCyp51H1 in Other Species

Following are examples of recombinant DNA constructs that can be used to express AsCyp51H1 in monocot or dicot species, either alone or in combination with another gene from the same biosynthetic pathway, using corn and soybean as examples. Constitutive promoters are used, and a person skilled in the art will appreciate that, depending on the target pathogen or other considerations, targeted promoters such as those of the examples described earlier in this text may be equally or even more efficacious or preferable due to special end uses of the plant material. Depending on the species and the enzymatic activities present in that species, other genes from the biosynthetic pathways might be included to increase expression levels.

In the examples below the following abbreviations for nucleic acid fragments comprising the different components are used:

"RB" and "LB" correspond to the right and left borders of the T-DNA.

"CAMV35S ENH" is the enhancer region of the cauliflower mosaic virus 35S promoter, which increases the level of expression of promoters to which it is attached (Benfey P. N., et al., 1990, *EMBO J.* 9:1685-1696).

"UBI PRO" is the promoter of the maize ubiquitin gene, as described in (Christensen et al., 1992, *Plant Mol. Biol.* 18:675-689).

"UBI 5'UTR" is the 5' leader region of the same maize ubiquitin gene.

"UBI INTRON1" is the intron of the same ubiquitin gene. Inclusion of this intron has been shown to increase expression levels.

"ATTR1" is a recombination site as described in the Gateway™ cloning system manual (Invitrogen, Carlsbad, Calif., USA).

"CCDB" is a bacterial negative selectable marker described in the Gateway™ cloning system manual.

"ATTR2" is a recombination site as described in the Gateway™ cloning system manual.

"PINII" is the transcription termination gene from the potato protease inhibitor II gene.

"CAMV35SPRO" is the promoter of the cauliflower mosaic virus 35S gene, a constitutive promoter commonly used in plants (Odell J. T. et al., 1985, *Nature* 313:810-812).

"ADH1 INTRON1" is the intron of the maize ADH1 gene. Inclusion of this intron has been shown to increase expression levels (Luehrsen K. R. and Walbot V., 1991, *Mol. Gen. Genet.* 225:81-93).

"BAR" is an herbicide resistance gene commonly used as a selectable marker in corn transformation.

"SCP1" is a synthetic constitutive promoter for use in plants and is described in U.S. Pat. 6,072,050.

"OMEGA 5' UTR" is the 5' leader region of a tobacco mosaic virus gene, whose use has been shown to enhance translation levels (Gallie et al., 1989, in *Molecular Biology of RNA*, ed. Cech (Liss, New York), pp. 237-256).

"BAS" is the coding sequence for the β-amyrin synthase gene (Haralampidis K. et al., 2001, *Proc. Natl. Acad. Sci. U.S.A.* 98:13431-13436).

"SPC1" is a coding sequence for a polypeptide that provides resistance to the antibiotic spectinomycin, allowing bacterial selection Svab, Z. and Maliga, P., 1991, *Mol. Gen. Genet.* 228:316-319.

"ColE1 ORI" is a DNA origin of replication functional in *E. coli*.

Constructs for the Expression of Saponin Biosynthetic Genes in Maize

Fragments containing the open reading frames of AsCyp51H1 and BAS are obtained respectively from clones described in earlier examples and as described in (Haralampidis K. et al., 2001, *Proc. Natl. Acad. Sci. U.S.A.* 98:13431-13436). In each case PCR amplification is carried out with primers that result in the open reading frames being flanked by restriction sites allowing their cloning into the BamHI and EcoRV restriction sites of modified Gateway Entry Vectors (Invitrogen, Carlsbad, Calif., USA). BamHI and EcoRV are added to AsCyp51H1, while BamHI and HpaI are added to BAS (EcoRV and HpaI both leave blunt ends). Other restriction sites could be used so long as they do not cut the genes internally. After ligation, the two resulting "entry vectors" consist of ATTL1-AsCyp51H1-ATTL2 and ATTL3-BAS-ATTL4, and both contain kanamycin resistance for bacterial selection. The sequences of the resulting polynucleotides are shown in SEQ ID NOs:27 and 28. ATTL1, 2, 3, and 4 are recombination sites provided in the Invitrogen Gateway cloning system (Carlsbad, Calif., USA).

Maize Recombinant DNA Construct 1: E35S-UBI-AsCYP51H1-PINII

This construct can be used to express the AsCYP51H1 gene alone in corn. The AsCYP51H1 entry vector is used in a Gateway LR reaction with a Gateway modified *Agrobacterium* transformation vector backbone modified from pSB1 (Komari, T. et al., 1996, *Plant J.* 10:165-174) by the addition of the following components at the cos site: RB-CAMV35S ENH-UBI PRO-UBI 5'UTR-UBI INTRON1-ATTR1-CCDB-ATTR2-PINII+CAMV35S ENH-CAMV35S PRO-ADH1 INTRON1-BAR-PINII–LB-SPC-ColE1 ORI. In this Gateway reaction, ATTL1 and ATTL2 recombine with ATTR1 and ATTR2, thereby transferring the AsCYP51H1 gene into the destination vector, replacing CCDB, which is toxic to *E. coli*, and allowing screening for successful clones as described in the Gateway manual (Invitrogen, Carlsbad, Calif., USA). This resulting construct contains a T-DNA which will be transferred into the plant genome and contains RB-CAMV35S ENH-UBI PRO-UBI 5'UTR-UBI INTRON1-ATTB1-AsCYP51H1-ATTB2-PINII+ CAMV35S ENH-CAMV35S PRO-ADH1 INTRON1-BAR-PINII–LB. The nucleotide sequence of the region between the RB and LB is shown in SEQ ID NO:29 and the reminder of the vector is described in Kormai, T. et al., op cit., with the exception of the SPC and ColE1 components. This construct is electroporated into LBA4404 *Agrobacterium tumefaciens* cells and used in transformation experiments such as those described in Example 6 below.

Maize Recombinant DNA Construct 2: E35S-UBI-AsCYP51H1-PINII+UBI-BAS–PINII

This construct allows the simultaneous expression of the AsCYP51H1 and BAS. The AsCYP51H1 and BAS entry vectors are used together in a Gateway LR reaction with a Gateway modified *Agrobacterium* transformation vector backbone modified from pSB1 (Komari, T. et al., 1996, *Plant J.* 10:165-174) by the addition of the following components at the cos site: RB-CAMV35S ENH-UBI PRO-UBI 5'UTR-UBI INTRON1-ATTR1-CCDB-ATTR2-PINII+CAMV35S ENH-UBI PRO-UBI 5'UTR-UBI INTRON1-ATTR3-CCDB-ATTR4-PINII+CAMV35S ENH-CAMV35S PRO-ADH1 INTRON1-BAR-PINII–LB-SPC-ColE1 ORI. In this Gateway reaction, ATTL1 and ATTL2 recombine with ATTR1 and ATTR2, while ATTL3 and ATTL4 recombine with ATTR3 and ATTR4. As a result both, AsCYP51H1 and BAS, are transferred in to replace the CCDB genes, which allows screening for successful recombination as noted earlier. The final construct, thus, contains as T-DNA which will be transferred into the plant genome RB-CAMV35S ENH-UBI PRO-UBI 5'UTR-UBI INTRON1-ATTB1-AsCYP51H1-ATTB2-PINII+ CAMV35S ENH-UBI PRO-UBI 5'UTR-UBI INTRON1-ATTB3-BAS-ATTB4-PINII+CAMV35S ENH-CAMV35S PRO-ADH1 INTRON1-BAR-PINII–LB. The nucleotide sequence of the fragment corresponding to the region between RB and LB is shown in SEQ ID NO:30 and the reminder of the vector is described in Kormai, T. et al., op cit., with the exception of the SPC and ColE1 components. These constructs may be electroporated into LBA4404 *Agrobacterium tumefaciens* cells and used in transformation experiments such as those described in Example 6 below.

Constructs for the Expression of Saponin Biosynthetic Genes in Soybean

To prepare the two recombinant DNA constructs described below for the expression of saponin biosynthetic genes in soybean the following steps are done first. The AsCyp51H1 and BAS open reading frames are obtained by PCR amplification as described above for the maize constructs, except that in assembling constructs for expression in soybean, different restriction endonuclease sites are built into the PCR primers such that NcoI and BamHI will flank the AsCyp51H1 open reading frame coding sequence while XbaI and XmaI will flank that of BAS.

Soybean Recombinant DNA Construct 1: SCP1-O'-AsCyp51H1-PINII

This construct can be used to express the AsCYP51H1 gene alone in dicots. After ligating a polynucleotide comprising the open reading frame of AsCyp51H1 into a vector containing SCP1-O'-NcoI-BamHI-PINII, the plasmid is linearized for bombardment by cutting with the restriction enzymes NruI and Eco47III and extracting the desired band of DNA from a gel. This process also removes the nucleotides encoding ampicillin resistance used for bacterial selection. This insert contains SCP1 PRO-OMEGA 5'UTR-AsCyp51H1-PINII and its nucleotide sequence is shown in SEQ ID NO:31. This fragment is used for soybean transformation as described in Example 7 below.

Soybean Recombinant DNA Construct 2:

SCP1-O'-AsCyp51H1-PINII+SUP-O'-BAS-PINII

This construct allows simultaneous expression of AsCYP51H1 and BAS in dicots. A polynucleotide comprising the open reading frame of BAS will be ligated into a vector containing SUP PRO-OMEGA 5'UTR, the XbaI and XmaI restriction sites, and PINII. This resulting cassette will then be ligated into the Soybean Recombinant DNA Fragment 1 plasmid constructed above, using the restriction enzymes BlpI and Eco47III. Prior to its use in bombardment of cells this final plasmid will be linearized by digestion with the flanking restriction enzyme NruI and the desired DNA band will be isolated after separation by gel electrophoresis. This process also removes the polynucleotide encoding ampicillin resistance which is used for bacterial selection. The isolated insert contains SCP1 PRO-OMEGA 5'UTR-AsCyp51H1-PINII+SUP PRO-OMEGA 5'UTR-BAS-PINII. The nucleotide sequence of this insert is shown in SEQ ID NO:32. This fragment may be used for soybean transformation as described in Example 7 below.

EXAMPLE 6

Agrobacterium-mediated Transformation of Maize and Regeneration of Transgenic Plants The recombinant DNA constructs prepared in Example 5 above may be used to prepare transgenic maize plants as follows.

Maize may be transformed with any of the polynucleotide constructs described in Example 5 using the method of Zhao(U.S. Pat. No. 5,981,840, and PCT patent publication WO98/32326). Briefly, immature embryos are isolated from maize and the embryos contacted with a suspension of Agrobacterium, where the bacteria are capable of transferring the polynucleotide construct to at least one cell of at least one of the immature embryos (step 1: the infection step). In this step the immature embryos are immersed in an Agrobacterium suspension for the initiation of inoculation. The embryos are co-cultured for a time with the Agrobacterium (step 2: the co-cultivation step). The immature embryos are cultured on solid medium following the infection step. Following this co-cultivation period an optional "resting" step is performed. In this resting step, the embryos are incubated in the presence of at least one antibiotic known to inhibit the growth of Agrobacterium without the addition of a selective agent for plant transformants (step 3: resting step). The immature embryos are cultured on solid medium with antibiotic, but without a selecting agent, for elimination of Agrobacterium and for a resting phase for the infected cells. Next, inoculated embryos are cultured on medium containing a selective agent and growing transformed callus is recovered (step 4: the selection step). The callus is then regenerated into plants (step 5: the regeneration step), and calli grown on selective medium are cultured on solid medium to regenerate the plants.

EXAMPLE 7

Transformation Of Somatic Soybean Embryo Cultures and Regeneration Of Soybean Plants Transformation of soybean with the polynucleotide constructs of Example 5 may be accomplished using the following soybean transformation procedures.

The following stock solutions and media are used for transformation and regeneration of soybean plants:

Stock Solutions (per Liter)

100× Sulfate Stock: 37.0 g MgSO4.7H2O, 1.69 g MnSO4.H2O, 0.86 g ZnSO4.7H2O, 0.0025 g CuSO4.5H2O.

100× Halides Stock: 30.0 g CaCl2.2H2O, 0.083 g KI, 0.0025 g CoCl2.6H2O,

100× P, B, Mo Stock: 18.5 g KH2PO4, 0.62 g H3BO3, 0.025 g Na2MoO4.2H2O

100× Fe EDTA Stock: 3.724 g Na2EDTA, 2.784 g FeSO4.7H2O.

2,4-D Stock: 10 mg/mL.

1000× Vitamin B5 Stock: 10.0 g myo-inositol, 0.10 g nicotinic acid, 0.10 g pyridoxine HCl, 1 g thiamine.

Media (per Liter)

SB196: 1 ml B5 vitamin stock, 1 mL 2,4-D stock, 10 ml of each of the remaining above stock solutions, 0.463 g (NH4)2 SO4, 2.83 g KNO3, 1 g asparagine, 10 g sucrose, pH 5.7.

SB103: 1 package Murashige & Skoog salts mixture, 1 ml B5 vitamin stock, 750 mg MgCl2 hexahydrate, 60 g maltose, 2 g gelrite, pH 5.7.

SB166: SB103 supplemented with 5 g per liter activated charcoal.

SB71-4: Gamborg's B5 salts (Gibco-BRL catalog No. 21153-028), 1 ml B5 vitamin stock, 30 g sucrose, 5 g TC agar, pH 5.7.

Soybean embryogenic suspension cultures are maintained in 35 ml liquid medium (SB196) on a rotary shaker (150 rpm) at 28° C. with fluorescent lights providing a 16 hour day/8 hour night cycle. Cultures are subcultured every 2 weeks by inoculating approximately 35 mg of tissue into 35 ml of fresh liquid media.

Soybean embryogenic suspension cultures are transformed by the method of particle gun bombardment (see Klein et al.,1987, *Nature* 327:70-73) using a DuPont Biolistic PDS1000/He instrument.

In particle gun bombardment procedures it is possible to use either purified entire plasmid DNA or DNA constructs containing only the recombinant DNA expression cassette(s) of interest. For every eight bombardment transformations, 30 μl of suspension is prepared containing 1 to 90 picograms (pg) of DNA construct per base pair of DNA fragment. The recombinant DNA plasmid or construct used to express the antifungal gene is on a separate recombinant DNA plasmid or construct from the selectable marker gene. All recombinant DNA plasmids or constructs are co-precipitated onto gold particles as follows. The DNAs in suspension are added to 50 μl of a 20 to 60 mg/ml 0.6 μm gold particle suspension and then combined with 50 μl 2.5 M CaCl2 and 20 μl 0.1 M spermidine. The mixture is pulse vortexed 5 times, centrifuged in a microfuge for 10 seconds, and the supernatant removed. The DNA-coated particles are then washed once with 150 μl of 100% ethanol, pulse vortexed, centrifuged in a microfuge again, and resuspended in 85 μl of anhydrous ethanol. Five μl of the DNA-coated gold particles are then loaded on each macrocarrier disk.

Approximately 150 to 250 mg of two-week-old soybean embryogenic suspension culture is placed in an empty 60 mm×15 mm petri plate and the residual liquid is removed from the tissue using a pipette. The tissue is placed about 3.5 inches away from the retaining screen and each plate of tissue is bombarded once. Membrane rupture pressure is set at 650 psi and the chamber is evacuated to −28 inches of Hg. Eighteen plates are bombarded, and, following bombardment, the tissue from each plate is divided between two flasks, placed back into liquid media, and cultured as described above.

Seven days after bombardment, the liquid medium is exchanged with fresh SB196 medium supplemented with 50 mg/ml hygromycin or 100 ng/ml chlorsulfuron, depending on the selectable marker gene used in transformation. The selective medium is refreshed weekly or biweekly. Seven weeks post-bombardment, green, transformed tissue is observed growing from untransformed, necrotic embryogenic clusters. Isolated green tissue is removed and inoculated into individual flasks to generate new, clonally-propagated, transformed embryogenic suspension cultures. Thus, each new line is treated as independent transformation event. These suspensions can then be maintained as suspensions of embryos clustered in an immature developmental stage through subculture or can be regenerated into whole plants by maturation and germination of individual somatic embryos.

Transformed embryogenic clusters are removed from liquid culture and placed on solid agar medium (SB166)

containing no hormones or antibiotics for one week. Embryos are cultured at 26° C. with mixed fluorescent and incandescent lights on a 16-hour day 8-hour night schedule. After one week, the cultures are then transferred to SB103 medium and maintained in the same growth conditions for 3 additional weeks. Prior to transfer from liquid culture to solid medium, tissue from selected lines is assayed by PCR or Southern analysis for the presence of the antifungal gene.

Somatic embryos become suitable for germination after 4 weeks and are then removed from the maturation medium and dried in empty petri dishes for 1 to 5 days. The dried embryos are then planted in SB71-4 medium where they are allowed to germinate under the same light and germination conditions described above. Germinated embryos are transferred to sterile soil and grown to maturity.

Various modifications of the invention in addition to those shown and described herein will be apparent to those skilled in the art from the foregoing description. Such modifications are also intended to fall within the scope of the appended claims.

The disclosure of each reference set forth above is incorporated herein by reference in its entirety.

What is claimed is:

1. An isolated polynucleotide comprising:
   a) a nucleotide sequence encoding a Cyp51H enzyme having an amino acid sequence that is at least 95% identical, based on the Clustal V method of alignment with pairwise alignment default parameters of KTUPLE=1, GAP PENALTY=3, WINDOW=5 and DIAGONALS SAVED=5, when compared to SEQ ID NO:14; or
   b) a nucleotide sequence comprising the full complement of (a).

2. The polynucleotide of claim 1, wherein the amino acid sequence of the polypeptide comprises SEQ ID NO:14.

3. The polynucleotide of claim 1 wherein the nucleotide sequence comprises one of SEQ ID NO:5 or SEQ ID NO:13.

4. A vector comprising the polynucleotide of claim 1.

5. A recombinant DNA construct comprising the isolated polynucleotide of claim 1 operably linked to at least one regulatory sequence.

6. A method for transforming a cell, comprising transforming a cell with the recombinant DNA construct of claim 5.

7. A transformed cell comprising the recombinant DNA construct of claim 5.

8. A method for producing a transgenic plant comprising transforming a plant cell with the recombinant DNA construct of claim 5 and regenerating a transgenic plant from the transformed plant cell.

9. A transgenic plant comprising the recombinant DNA construct of claim 5.

10. A seed comprising the recombinant DNA construct of claim 5.

11. An isolated host cell comprising the recombinant DNA construct of claim 5.

12. The host cell of claim 10 wherein said host cell is selected from a yeast cell, a bacterial cell, and a plant cell.

13. A transgenic plant comprising a polynucleotide of claim 1 operably linked to a heterologous promoter, said plant having an altered level of a triterpene.

14. The plant of claim 13 wherein said triterpene is a saponin derived from β-amyrin and said level is increased.

15. The plant of claim 13 wherein said triterpene is a saponin derived from β-amyrin and said level is decreased.

16. The plant of claim 13 wherein said plant is selected from the group consisting of a monocot and a dicot.

17. The plant of claim 16 wherein said monocot is selected from the group consisting of wheat, oat, rice, and corn.

18. The plant of claim 16 wherein said dicot is soybean.

* * * * *

SEQUENCE LISTING

```
<160> NUMBER OF SEQ ID NOS: 32

<210> SEQ ID NO 1
<211> LENGTH: 480
<212> TYPE: DNA
<213> ORGANISM: Artificial
<220> FEATURE:
<223> OTHER INFORMATION: RFLP probe isu441

<400> SEQUENCE: 1
cctaaaggta ccacgttagc acatcttgta atgctaacag gtaaggtgcc acacacttac      60 aaggacccg aggtctatga tccagatcgg tttcgtgttg aagagagga ggataaaatt      120 gggggtaaac tctcttacac aatttttggt gctggaaggc atgctggcgc tggcgagtcc      180
tttgctttca tgcaaataaa gattatctgg agccatttgc tgagaaattt tgatcttaaa      240
ctgacttctc catttcccaa gcaagattgg agcaagttta taatagagcc taaaggcaaa      300
gtaatggtaa gttacaagag atgtcgtatg cctgcaaact aaatctggca ttttatatgt      360
ctactagcac ctatttgcac ggatgtatct ttgtgtgcgt gtagaagaca tgtttggtag      420
ttatccatgg gcttatttac aataaggcgt cgcctttta tgtattattt acttcacttc      480

<210> SEQ ID NO 2
<211> LENGTH: 26
<212> TYPE: DNA
<213> ORGANISM: Artificial Sequence
<220> FEATURE:
<223> OTHER INFORMATION: Oligonucleotide primer ISU441-GSPF1

<400> SEQUENCE: 2
ctgacttctc catttcccaa gcaaga      26

<210> SEQ ID NO 3
<211> LENGTH: 26
<212> TYPE: DNA
<213> ORGANISM: Artificial Sequence
<220> FEATURE:
<223> OTHER INFORMATION: Oligonucleotide primer ISU441-GSPF2

<400> SEQUENCE: 3
ctactagcac ctatttgcac ggatgt      26

<210> SEQ ID NO 4
<211> LENGTH: 26
<212> TYPE: DNA
<213> ORGANISM: Artificial Sequence
<220> FEATURE:
<223> OTHER INFORMATION: Oligonucleotide primer ISU441-GSPR2

<400> SEQUENCE: 4
```

```
atcctcctct cttccaacac gaaacc                                           26
```

<210> SEQ ID NO 5
<211> LENGTH: 1790
<212> TYPE: DNA
<213> ORGANISM: Avena strigosa
<220> FEATURE:
<221> NAME/KEY: misc_feature
<222> LOCATION: (1)..(1790)
<223> OTHER INFORMATION: cDNA for AsCYPA
<220> FEATURE:
<221> NAME/KEY: misc_feature
<222> LOCATION: (1)..(1790)
<223> OTHER INFORMATION: cDNA for AsCYP51H10

<400> SEQUENCE: 5

```
gcattgactg ctaccagctg tgtgctggac actcgttcac agtgaaccag tcaggaggat       60
ttcaaattcg tattcagtgt gaatcctcta gtcaataacg acatggacat gacaatttgc      120
gtcgtttggt tggtcttagc aattatatcc atcgctgcag tagtatccaa gagttcaaag      180
cgaagcaatg cctctgattc agtggtgaca cgaccacctc caccggtggt gacaggaatt      240
gatctcctca gttcttaca tgctctttgt agaaaggacc ctgaagctgc aatgatgtat       300
ctgtataaca agttaggcag tattttcaca ttaagttttt tgtggaaaag agtaaccatc      360
ttgattgggc acgaggcctc cattcctttc tttcatggtt tggagtcaga tgtttcacaa      420
ggaaatttca atgagttcac cgtgccaatg ttcggcaaag agaatgggta tgctgtggaa      480
tatgctactc gaattgagca gtctcgcttc ttctatgatt ctctaaaggc atcgcagctg      540
aggagccatg ttgatctcat tcgacaggaa gtggaggagt actttgcaaa atggggagac      600
gagggtgaag tcgatctgaa acaagagttc accaagttac tcatgttgat tgctggtcgc      660
tgcctacttg gaagtgaggt ccgagatacg atatttggtg agttctacac attgtttgct      720
gatattgagg aggggtcaa cttgttcagt tacatgttcc catatatgcc ggttccagta      780
aacaaccgac gagacagagc acaaatgaag cttacaagta tagtgtctga gattgtgagg      840
tcaagaaaga gatgcaaccg cgtcgaggat gatatgctgc agagactgat agattccaga      900
tataaagatg gtcgtccaac aactgaaggg gaggtttccg ggatgatcat tggacttata      960
tttgctggaa agcacacaag tacaatcact gcctcctgga ccggagcttg ccttttgacc     1020
catccaaaat tcctaggtgc tgctgtcgag agcaaaagc aaatgatgag taaatacaag      1080
gataatatag actacaatat cctgtcagaa atggagattt tgcatagttg catcaaagag     1140
gcaggtcgga tgtatcccgc agcgccggtg ttgctgcgca agacactgaa ggagatcagt     1200
gtgcagacaa gagagggag tgaatatggt atccctaaag gtaccacgtt agcacatctt      1260
gtaatgctaa caggtaaggt gccacacact acaaggacc ccgaggtcta tgatccagat      1320
cggtttcgtg ttggaagaga ggaggataaa attggggggta aactctctta cacaattttt     1380
ggtgctggaa ggcatgcttg cgctggcgag tcctttgctt tcatgcaaat aaagattatc     1440
tggagccatt tgctgagaaa ttttgatctt aaactgactt ctccatttcc caagcaagat     1500
tggagcaagt ttataataga gcctaaaggc aaagtaatgg taagttacaa gagatgtcgt     1560
atgcctgcaa actaaatctg gcattttata tgtctactag cacctatttg cacggatgta     1620
tctttgtgtg cgtgtagaag acatgtttgg tagttatcca tgggcttatt tacaataagg      1680
cgtcgccttt ttatgtatta tttacttcac ttcatggacc ttttcttcaa acatttcgtt     1740
ggtcggcatg ttatgtaatg cttcataata ataattgctt ctgttatgtg               1790
```

```
<210> SEQ ID NO 6
<211> LENGTH: 30
<212> TYPE: DNA
<213> ORGANISM: Artificial Sequence
<220> FEATURE:
<223> OTHER INFORMATION: Oligonucleotide primer ISU441cF01

<400> SEQUENCE: 6
ccagtcagga ggatttcaaa ttcgtattca                                    30

<210> SEQ ID NO 7
<211> LENGTH: 26
<212> TYPE: DNA
<213> ORGANISM: Artificial Sequence
<220> FEATURE:
<223> OTHER INFORMATION: Oligonucleotide primer ISU441cR01

<400> SEQUENCE: 7
cgacgcctta ttgtaaataa gcccat                                        26

<210> SEQ ID NO 8
<211> LENGTH: 29
<212> TYPE: DNA
<213> ORGANISM: Artificial Sequence
<220> FEATURE:
<223> OTHER INFORMATION: Oligonucleotide primer ISU441gF1

<400> SEQUENCE: 8
acgagggtga agtcgatctg aaacaagag                                     29

<210> SEQ ID NO 9
<211> LENGTH: 24
<212> TYPE: DNA
<213> ORGANISM: Artificial Sequence
<220> FEATURE:
<223> OTHER INFORMATION: Oligonucleotide primer ISU441cF03

<400> SEQUENCE: 9
caattatatc catcgctgca gtag                                          24

<210> SEQ ID NO 10
<211> LENGTH: 25
<212> TYPE: DNA
<213> ORGANISM: Artificial Sequence
<220> FEATURE:
<223> OTHER INFORMATION: Oligonucleotide primer ISU441cF04

<400> SEQUENCE: 10
atgttgatct cattcgacag gaagt                                         25

<210> SEQ ID NO 11
<211> LENGTH: 27
<212> TYPE: DNA
<213> ORGANISM: Artificial Sequence
<220> FEATURE:
<223> OTHER INFORMATION: Oligonucleotide primer ISU441gF2

<400> SEQUENCE: 11
tgtcgaggag caaaagcaaa tgatgag                                       27

<210> SEQ ID NO 12
<211> LENGTH: 24
<212> TYPE: DNA
<213> ORGANISM: Artificial Sequence
<220> FEATURE:
<223> OTHER INFORMATION: Oligonucleotide primer ISU441gF4
```

<400> SEQUENCE: 12
gaacaagtgc gatggattat ggta                                              24

<210> SEQ ID NO 13
<211> LENGTH: 5992
<212> TYPE: DNA
<213> ORGANISM: Avena strigosa
<220> FEATURE:
<221> NAME/KEY: misc_feature
<222> LOCATION: (1)..(5992)
<223> OTHER INFORMATION: Genomic sequence for AsCYP51H
<220> FEATURE:
<221> NAME/KEY: misc_feature
<222> LOCATION: (1)..(5992)
<223> OTHER INFORMATION: Genomic sequence for AsCYP51H10

<400> SEQUENCE: 13
tgtacaggac acgtacaacc aaaaaactcc ttttgttccc attgagtgaa tttgtgtcga      60
tagggaccca tgcaaagaat tcaatctata ttgattgcca aaactaacgt tgcacgttaa     120
cggacagata gtttaccttc agtttggagt aaactcatgc tcgaaggtac aatactaata     180
aggtcattgc agcataagac acatgctagg cttcaaatga ttaattgagt acatgaaaga     240
gtatatattt taaaaatgat aagaaattca caaaccagat caagtaacgt cgaaggtttg     300
gaagagtgca caaccccaa tttcaaagat aggaaaattc agtttattga tcacacaata      360
gtgagagaca cggcccttgc aaaacagact gccaaaccac tgcatagtcg ccaaaacaac     420
gacaataaag ctcgaaaact atctccaagg agcagagcat gacgggccac actaagactt     480
ggaatggagg aatgctactt ttaatccatg ccgccttaat tacggaaatt tttcacgaat     540
aacacgctaa agtgacaaag atatatacct aattccacat gacagacgaa ccatgcatcc     600
attgcaaccc aataacttat agatcgtgtt aaggtgaggg aatgatttt gtgtaagagt      660 aaacactttg ttataagtta acataaaaaa ccaaatattt acaaactcta ataacaatac     720
aattgaataa cgagagtgta tttacttgga tcaagtgtct tgtccatatt gtcacatagt     780
cactacaaac attattctta caaagtatc cacatcaaaa aaataaatta tattatgtat      840
aaaaagcaac ataagaccta aaatagagag atattctaga aattcttaca aaagccaaac    900
atccagctgc taatatggta gaccatattg gtatttaaac atatcacaac taggggtttt    960
gtttctcgct ggaaggaaat acttgtgggc aatggtattt ccggttttcg aaaatactag   1020
agctgccggt caaactacct cccgaatttt ttcaaacaaa cccatccaaa gtttatcaaa   1080 attcttaaa ttttagaaaa atattaaaat acctatgaat ttggtatggt agtatttgtt    1140
cttagtggta accggaaaca cccgtttctg actacatacc cgaacatcgg tcaagaataa   1200
aaacctgatc ataaccattg aatctccgta agtttgctaa cgtatcatgc tgttctcatg   1260
ttacataaga aaaatgataa aaatcccctc gatttagtaa cactatgcat taggtttgta   1320
gaagagtaaa tgtttgagaa aatgatagta gattattaat atttgtcctg accatgcgca   1380
tgagacacta gctaagtgtc ccatagtaag tattgacaca tctagagata tgtccatgtc   1440
ttaaatatcg tgtatttgtt atattaagga tataaatgtg agaatatgtt ggtataacat   1500
tggaaaaaat gttaacatac taaacatgac tacctcacat ttttacgga cattgatatt    1560 ctagaactat caataccgct atactaccag taggatatca tcttcaatat cgatgatgta   1620
gatatgcaaa cttgcacttt caaagaatg tttaatataa ttttctaagt gaactatcta    1680
ccgagacatt atatctttaa taatataaaa aattctttat tgattttcct gaatttgaaa   1740
cccaaaatat gtcggtctac ctcttcgaaa aatgacattt agctcatggt atgtcttttt   1800

```
ccatgatata ataaagtaat ttgtatctta tatttaagta tacaagtcat tcaaaaggta   1860
gttttagtca tgtgatattt tttgtgtggt gtctctagaa taattattaa taaattcaaa   1920
attttagtat gtatataacc ataaatttat ttctcaagca aataaaatga gattaagaca   1980
ttgccctcgc aattgcgagg tctacctggc tagtgagaga aaaaggaga acatgcattg   2040 aaccagagag agagtaataa atgagataac ccttataatc tcaaacaata taaaaagct   2100 cttaggacta ataatcctga acagaggtag taacatgcaa ctgtatgcat tgcgaactac   2160
gcattttgat gacatgacat gtcattaaat aatgaaaaca gtcttgtggt aactagctat   2220
gttaccataa cacaagacat gtctaagtaa gatgagtcta tgatataata aatgagatat   2280
tccataaaac tagatataag ttactaccca ctctgaagat gataacaaag aatagtaatg   2340
cacgcatgac aatacactat ttactagtct tctgtaaatt tatccgatca aaatggcctg   2400
ctcgggttgc aatgcattct cacgtgttga agtttctgat atcgatgtaa ggtggtcata   2460
caagacgaga ataccaatgg agtactagat ctcgatggac taagcatatg caaattttat   2520
ctgaacaaga agcaggctta ctcaggttgc aatgtattct cacgtactgt tgccttgctc   2580
cagacgaccc gcatgcaaaa gcgagcttgt cccctagagt tgtgaatact agtttcatta   2640
gaaacatcac gtactgcgaa agccattaat gcctctgtga acacaatcgg gcagtattga   2700
ctagaatctc caagatcagg ccatgaaatt agttgtttac ttgataatat tgtccaagag   2760
ttagggttta ggtcaagtag aggccgtggc ttttttccat ttctccataa taaaagggct   2820
taggtcaagt agtagctgcc tatataaatg aggcattgcg gggttcctta ctcacttgtg   2880
tgcattgact gctaccagct gtgtgctgga cactcgttca cagtgaacca gtcaggagga   2940
tttcaaattc gtattcaggt atgcttgatt ttagttttta agtcatatga gttcattttt   3000
agatcatttt ttcatacgag agaaataaga ctagggctag gtttgttctt catatgggcc   3060
gggtgcaaca tttcgataac aatcacgcat cagagctatt acttgttctt ctgaatttc    3120 tatagccttt aaaaaccgac aatcagagtt caattaccaa tctagtcttg gtcatatttt   3180
gtttcttaat gaagtgtttt tgcttcactt tgtccttgtg gagtcgaatg tggcttcctg   3240
tttagactgt tagctaggtt cacccttttca gatttcttca tactaattat cttcatattc   3300
tgccagtgtg aatcctctag tcaataacga catggacatg acaatttgcg tcgtttggtt   3360
ggtcttagca attatatcca tcgctgcagt agtatccaag agttcaaagc gaagcaatgc   3420
ctctgattca gtggtgacac gaccacctcc accggtggtg acaggaattg atctcctcaa   3480
gttcttacat gctctttgta gaaaggaccc tgaagctgca atgatgtatc tgtataacaa   3540
gttaggcagt atttttcacat taagttttt gtggaaaaga gtaaccatct tgattgggca   3600
cgaggcctcc attcctttct ttcatggttt ggagtcagat gtttcacaag gaaatttcaa   3660
tgagttcacc gtgccaatgt tcggcaaaga gaatgggtat gctgtggaat atgctactcg   3720
aattgagcag tctcgcttct tctatgattc tctaaaggca tcgcagctga ggagccatgt   3780
tgatctcatt cgacaggaag tggaggtaat tacaaaaata tacattgatg ccatcatgcc   3840
tgtaccattc tagcttgtga gaaatgctat ttttttagaag aagtcgcaat taatccatgt   3900
aggattatga agaactgagt ttggtagttc atatttctat ttccatttca aaaatagaaa   3960
atgttgcact gttcgtagac tcaacatagc atcttcagca cttaatctta ctatgtgaat   4020
ataagtaatg tttcatgtgg aattgtgtgt tgtaacaaat ctaattttaa aaataaaaca   4080
aaaaatccta tggctcattc ctaaaatgaa acgatataga aaatgttagt gtgcaaaaga   4140
```

-continued

```
agaagtagag tatgcatcca tcctttatag tctaatttat tatggattgg atgtttcttt    4200
aattctcaaa tgaaatgctt gaaatcccgg gtcttgtact ttttatagta ttgtgtactt    4260
gccatagaaa aaatagtcta ctttccattc tcatatttcc ccgtggtaaa ttggaatggc    4320
tgaataaata tgtaaatggc aggtgtactt tttatgctcg ctctgtcgtt attaattagt    4380
aagtatacat atatagtttg aaactaattt atgaaaatta aacagccaga gttagaataa    4440
accaataaat tacccaacat ctatgagaac aagtgcgatg gattatggta attatatctt    4500
attcctcgtt ataaagttgg attaccagat atttgatcag ggtctatgtc gaacccttc     4560 ccacatgaaa catatgaatt agcctaaaaa atactgttat ttcttataat aatacttatt    4620
aattgattca cttgaaaaca gggttacatg tagttatttc gctacgatcg aaagaataaa    4680
aataatatgt gaacattttc tataaactta tgttgttccc cgcttctaga tttacgacca    4740
cacacttatc catcgatcta atacactata ttctacagga gtactttgca aaatggggag    4800
acgagggtga agtcgatctg aaacaagagt tcaccaagtt actcatgttg attgctggtc    4860
gctgcctact tggaagtgag gtccgagata cgatatttgg tgagttctac acattgtttg    4920
ctgatattga ggaggggggt caacttgttca gttacatgtt cccatatatg ccggttccag    4980
taaacaaccg acgagacaga gcacaaatga agcttacaag tatagtgtct gagattgtga    5040
ggtcaagaaa gagatgcaac cgcgtcgagg atgatatgct gcagagactg atagattcca    5100
gatataaaga tggtcgtcca acaactgaag gggaggttc cgggatgatc attggactta    5160
tatttgctgg aaagcacaca agtacaatca ctgcctcctg gaccggagct tgccttttga    5220
cccatccaaa attcctaggt gctgctgtcg aggagcaaaa gcaaatgatg agtaaataca    5280
aggataatat agactacaat atcctgtcag aaatggagat tttgcatagt tgcatcaaag    5340
aggcaggtcg gatgtatccc gcagcgccgg tgttgctgcg caagacactg aaggagatca    5400
gtgtgcagac aagagaggga ggtgaatatg gtatccctaa aggtaccacg ttagcacatc    5460
ttgtaatgct aacaggtaag gtgccacaca cttacaagga ccccgaggtc tatgatccag    5520
atcggtttcg tgttgaaga gaggaggata aaattggggg taaactctct tacacaattt    5580
ttggtgctgg aaggcatgct tgcgctggcg agtcctttgc tttcatgcaa ataaagatta    5640
tctggagcca tttgctgaga aattttgatc ttaaactgac ttctccattt cccaagcaag    5700
attggagcaa gtttataata gagcctaaag gcaaagtaat ggtaagttac aagagatgtc    5760
gtatgcctgc aaactaaatc tggcatttta tatgtctact agcacctatt tgcacggatg    5820
tatctttgtg tgcgtgtaga agacatgttt ggtagttatc catggcttta tttacaataa    5880
ggcgtcgcct ttttatgtat tatttacttc acttcatgga ccttttcttc aaacatttcg    5940
ttggtcggca tgttatgtaa tgcttcataa taataattgc ttctgttatg tg           5992
```

<210> SEQ ID NO 14
<211> LENGTH: 490
<212> TYPE: PRT
<213> ORGANISM: Avena strigosa
<220> FEATURE:
<221> NAME/KEY: MISC_FEATURE
<222> LOCATION: (1)..(490)
<223> OTHER INFORMATION: AsCYP51H translation
<220> FEATURE:
<221> NAME/KEY: MISC_FEATURE
<222> LOCATION: (1)..(490)
<223> OTHER INFORMATION: AsCYP51H10 translation

<400> SEQUENCE: 14

Met Asp Met Thr Ile Cys Val Val Trp Leu Val Leu Ala Ile Ile Ser

-continued

```
1               5                   10                  15
Ile Ala Ala Val Val Ser Lys Ser Ser Lys Arg Ser Asn Ala Ser Asp
                20                  25                  30

Ser Val Val Thr Arg Pro Pro Pro Val Val Thr Gly Ile Asp Leu
        35                  40                  45

Leu Lys Phe Leu His Ala Leu Cys Arg Lys Asp Pro Glu Ala Ala Met
        50                  55                  60

Met Tyr Leu Tyr Asn Lys Leu Gly Ser Ile Phe Thr Leu Ser Phe Leu
65                  70                  75                  80

Trp Lys Arg Val Thr Ile Leu Ile Gly His Glu Ala Ser Ile Pro Phe
                85                  90                  95

Phe His Gly Leu Glu Ser Asp Val Ser Gln Gly Asn Phe Asn Glu Phe
            100                 105                 110

Thr Val Pro Met Phe Gly Lys Glu Asn Gly Tyr Ala Val Glu Tyr Ala
            115                 120                 125

Thr Arg Ile Glu Gln Ser Arg Phe Phe Tyr Asp Ser Leu Lys Ala Ser
            130                 135                 140

Gln Leu Arg Ser His Val Asp Leu Ile Arg Gln Glu Val Glu Glu Tyr
145                 150                 155                 160

Phe Ala Lys Trp Gly Asp Glu Gly Val Asp Leu Lys Gln Glu Phe
                165                 170                 175

Thr Lys Leu Leu Met Leu Ile Ala Gly Arg Cys Leu Leu Gly Ser Glu
            180                 185                 190

Val Arg Asp Thr Ile Phe Gly Glu Phe Tyr Thr Leu Phe Ala Asp Ile
            195                 200                 205

Glu Glu Gly Val Asn Leu Phe Ser Tyr Met Phe Pro Tyr Met Pro Val
        210                 215                 220

Pro Val Asn Asn Arg Arg Asp Arg Ala Gln Met Lys Leu Thr Ser Ile
225                 230                 235                 240

Val Ser Glu Ile Val Arg Ser Arg Lys Arg Cys Asn Arg Val Glu Asp
                245                 250                 255

Asp Met Leu Gln Arg Leu Ile Asp Ser Arg Tyr Lys Asp Gly Arg Pro
            260                 265                 270

Thr Thr Glu Gly Glu Val Ser Gly Met Ile Ile Gly Leu Ile Phe Ala
        275                 280                 285

Gly Lys His Thr Ser Thr Ile Thr Ala Ser Trp Thr Gly Ala Cys Leu
        290                 295                 300

Leu Thr His Pro Lys Phe Leu Gly Ala Ala Val Glu Glu Gln Lys Gln
305                 310                 315                 320

Met Met Ser Lys Tyr Lys Asp Asn Ile Asp Tyr Asn Ile Leu Ser Glu
                325                 330                 335

Met Glu Ile Leu His Ser Cys Ile Lys Glu Ala Gly Arg Met Tyr Pro
            340                 345                 350

Ala Ala Pro Val Leu Leu Arg Lys Thr Leu Lys Glu Ile Ser Val Gln
            355                 360                 365

Thr Arg Glu Gly Gly Tyr Gly Ile Pro Lys Gly Thr Thr Leu Ala
        370                 375                 380

His Leu Val Met Leu Thr Gly Lys Val Pro His Thr Tyr Lys Asp Pro
385                 390                 395                 400

Glu Val Tyr Asp Pro Asp Arg Phe Arg Val Gly Arg Glu Glu Asp Lys
                405                 410                 415

Ile Gly Gly Lys Leu Ser Tyr Thr Ile Phe Gly Ala Gly Arg His Ala
            420                 425                 430
```

Cys Ala Gly Glu Ser Phe Ala Phe Met Gln Ile Lys Ile Ile Trp Ser
            435                 440                 445

His Leu Leu Arg Asn Phe Asp Leu Lys Leu Thr Ser Pro Phe Pro Lys
    450                 455                 460

Gln Asp Trp Ser Lys Phe Ile Ile Glu Pro Lys Gly Lys Val Met Val
465                 470                 475                 480

Ser Tyr Lys Arg Cys Arg Met Pro Ala Asn
                485                 490

<210> SEQ ID NO 15
<211> LENGTH: 22
<212> TYPE: DNA
<213> ORGANISM: Artificial Sequence
<220> FEATURE:
<223> OTHER INFORMATION: Oligonucleotide primer ISU441pF01

<400> SEQUENCE: 15
cgtggctttt ttccatttct cc                                              22

<210> SEQ ID NO 16
<211> LENGTH: 22
<212> TYPE: DNA
<213> ORGANISM: Artificial Sequence
<220> FEATURE:
<223> OTHER INFORMATION: Oligonucleotide primer ISU441cR03

<400> SEQUENCE: 16
gagatcaatt cctgtcacca cc                                              22

<210> SEQ ID NO 17
<211> LENGTH: 27
<212> TYPE: DNA
<213> ORGANISM: Artificial Sequence
<220> FEATURE:
<223> OTHER INFORMATION: Oligonucleotide primer ISU441indeR

<400> SEQUENCE: 17
gcacactaac attttctata tcgtttc                                         27

<210> SEQ ID NO 18
<211> LENGTH: 24
<212> TYPE: DNA
<213> ORGANISM: Artificial Sequence
<220> FEATURE:
<223> OTHER INFORMATION: Oligonucleotide primer ISU441gF5

<400> SEQUENCE: 18
tactatgtga atataagtaa tgtt                                            24

<210> SEQ ID NO 19
<211> LENGTH: 14299
<212> TYPE: DNA
<213> ORGANISM: Avena strigosa
<220> FEATURE:
<221> NAME/KEY: misc_feature
<222> LOCATION: (1)..(14299)
<223> OTHER INFORMATION: AsCYP51H2 genomic sequence
<220> FEATURE:
<221> NAME/KEY: misc_feature
<222> LOCATION: (1)..(14299)
<223> OTHER INFORMATION: AsCYP51H11 genomic sequence

<400> SEQUENCE: 19
aagatattag atttaacact ctaaaattat ttagatgatg tggtttaatc gtggtgcctc     60

-continued

```
ttttagatat gtatatggct tttagtatat gctagatgct agatgggtag cataaatttt    120
ggtagctggt gaattaggag gctaacataa gacaagtgat acgtcggaaa tgtatctata    180 attttgatg ttccatgctt gtttagtatc tattttgttt tgctttgtct acacattgag     240 gtgttttat atcttttcta gaactaatct attaacaagt tgccacagtg ctagttgcct     300
gttttcttct gttttggtt ccagaaaggc agaaaatcaa aattctcgga attggatgga     360
acaaaagcca aatttaatat tttaccgtgg gcgacacgaa tcaagaagac gagacggagg    420
ggcgccaaag ggcggccaga ccccctaggc gtgggtgggc ccagctcacg cttgggcagg    480
gtgtggcccc ctggcggccc ccttcctcgc ctcttcgtct agaagaagcc cccgatgcag    540
aaaacctagg cacccgatca aaactccacg aaaccttcta tagacgccgc caccatcgtc    600
cctagatcgg ggggatctga agttcttccc gggaccctgc cggaggggag atcatcctga    660
ggccttcttc tccggtatga agcgtgagta gttccacctt ggactacggg tccatgtagt    720
agctagatgg ttgtatctcc tccttgtgct ttcatgtata gatcttgtga gctctgttca    780
tgatcaagat caaatctatt tgtaatcatg catgttgtgt ttgcggagat ccgatggata    840
ttgagattac tatgtcagat tgattaatgg ttttgtctat ttgatattat catgtctgtg    900
ttgtttgtga gcttgcattc tctccttttgt taagagctat attggccaaa tagttgctag    960
tgactccaat agagggtatt tatgctcgat agtgggttca tgcctctagt tttcaagaga   1020
agtgacaaaa atctcttcgg ttgtagatgt gctattgcca ctagggagaa caacggtctc   1080
ttattcatgg aacaagtgga ttgtttatct tacacacttt gcttaaagca gttgtctgtt   1140
gcttgcaact taatacttga ggggttcgg atgataacct gaaggtggac tactagtcat    1200
agatgcagtt ggatggcggt ctatgtatat tgttgtattg cccaatcgaa tcgcatagga   1260 tcttttttgtc aggtattgca ttgttatgcc ttgctcagtt cctctcaatt gccctgctgt   1320
aatttgttta tccttcatgc cctattgttt atctaaggag agcatctcta gtaaactata   1380
gatcccggtc caatctttac cagtgataca tcttatactg tttacttgct gcaaaccatt   1440
catcaccttc cacaccatac gtttaatcct ttgttacagc aaatcggtga gcttgacaac   1500
ctcactgatt cgttggggca aagtcttaag tttgtgttgt gaaggttttt acgttgcttg   1560
caacactttt gagacgtttt cttcctccta ctggtttgat aacctcggtt tcttactgag   1620
ggaaaacttg ccgttgtgct tatcacacct tcctcttggg gttttcaact aaacgtccca   1680
cgacagtact gggcgtcatc aacaagctta gagcatctcc aatagacgcg tagcgcaata   1740
aaaccgccaa tttagcgtgc ggagacagat ttgcacactc caaccagcac tgcataatcg   1800
cacgtgcgct aaattttagc acgtggcatt atgcaccatc atgagagatg tatttagcgt   1860
gtatttagcg ctcaggctcc agcgcgctgc aaatatcgac gacacgcgac tcgcaaccgt   1920
caatcttaaa attttgtgca cccttctgcc ttcctcctcg cgctgcctcc gatgtttttc   1980
cggcgatgga tgcctccacc agcactcctc caaccccct agtctttaga ccctgccgcc    2040
gttcgcaaac cctaacgctt gcaccgcaac aaactctgct gccggcgtcg tccatgttct   2100
cttcgcccac ccacgcagg cgagcgtcca gggtgcctcc cctgccgcc gcgaaggaaa     2160 ggaatgcccg cctcaaacgg ctggcggctg cggtgactgc tggccaaaag aagggcaaga   2220
cagctgcggg cattgccgcg tgacgagtcc agccgctatc gggccaattc cagccattgc   2280
cgtatcgtgc cgcctcccaa gcttttgaat tatgacatga atttgaacta tgctcatgat   2340
cttttgcaat gctccagcct gttgcgtgct gcattttac agcgccggga gcacacctga    2400
aaaatgcaaa atcattgctg taaaactagt ttagcgcatc agattatcac acgtctgttg   2460
```

```
gagatgctct tagcacgcac cctcacccaa ctggccgcat tccatctcaa atctaacaag    2520
gtggtccata caaggtaggt cgtgttggca ctggaccatg atctaacgac atcgagaatc    2580
acctgcgcgc gcgagcacct actctactat atataaccac acgcttctcg agtatgtatc    2640
tctcggctca caactcatgc cctgactcat agtattgatc ctgttgcaat cctcttgagc    2700 tttcttgta accaagagtt cattatttct gcagtgatgt ccctaaatcc attggctaaa    2760
gtttgaagta tccaggtatg ctcgatgtat tgtagaactc ttttaataaa gtagtaataa    2820
aaggccgatg caaaggctag gtagaggcca agtgcaaccc ttttcgataa aattgtacta    2880
gtatttgcta acgacatcga ttgtgcattt tatcatgcca taatcaaccc atttaacttt    2940
agacgcatca tctccaggtt cttgtgtcaa tcctatcacg gcttccctga gaactacacc    3000
atggcgttaa cagttagcgt catgttgttc tccctagcgc ttgttctcat cactgcagta    3060
gtcgcgaaga ttacaagtgg gagaattatc acagatcccg tgtgtgccct accagctcca    3120
cctgaggtca agggtattgc tcttctcaga ctcttgccta ctctgtttac agagggccct    3180
gaagctacaa tgcactatct gcataacaag cttggcagtg cattcacagt cagttttctt    3240
tggaaaaaga caaccttctt ggttggacag gaggcctccg ctattttctt ccaagggttg    3300
gagtcagagg ttacccaagg aaatttattt gagtttaccg tccccatgtt tggcacagag    3360
gtaggcttcg gcgtagatta cgctactcgc agggagcata cccgcttcat cgttgagtct    3420
ctaaagccat cacaactcag aagctatgtt gatcccatgc tgcaagaagt ggaggtaaat    3480
aacaaattaa cccaacctgg ctcttcttta ttcatttaaa ctatatggca tttatttgga    3540 caccccttgga ttaaataatt aactcggaca tgttaattag tcaagataaa ctttgctcag    3600
aattagttca tcttgtttcc aattgtaaga caaatactca atgtgggact aaagttccac    3660
gtcttcctta atttgggaca agagacgtgg aactaattct caattgtaaa attaaactta    3720
tatatctgtc caactaattc tcaatgtggg acaaagttcc attcgtcttg cgatggatgt    3780
tgcatgattg agtcaactga gcttaatatc tagaattatt gtaaaaaaac aaatgagctt    3840
ggcccaatat ttcaaataag ttgagtttaa tattggcccc acgagtacgg ctatgtttgt    3900
gagagctcca ctccgtcaaa cttcaccgca cctcaaaact ccgctccacc tcttagctct    3960
agaggaacaa aaaactgtat gggacaattg ttaactccaa cttcaaatta tgtatgggct    4020
actgtagaaa gataaataca ccatgtttat ttttcagagt ccgaacgttg ttttctagtt    4080
tacaagaaca tgcatctaac taagacatct gaacttctga ccaattatca ctagaagggg    4140
ggaaaaatgg gctcataggg ctgctgcata gagaagagca atgccataag aggtaatttc    4200
gtgaacaggc aactcagatc tcaataatgc acatggacac aatgtaaatg aacaacccaa    4260
caagcattca caagaacaca acgtcaacaa tttatcttac agagttatag gaacacacgc    4320
cattttctca taaaacccca aaagctttgt gtttcaattt atcgatagaa aaagaagta    4380 caatttataa gcctaagaaa aggccaacac ctataatcac acacccaaca ctcaaaacaa    4440
gaatatgact aaatggccga aatcgtcaa gtgattctcc aagacgccac aaagtgaact    4500
ccttccctaa acagaacct tgccaatgaa agtcgcagtg cttgtgcatc gtcaaaatta    4560
ccaagagcca gccagccgca accaagatgc gttccacccg aatcccgcga gccaacgatg    4620
gctcaactgg gagcattgtt gctccggcct cagcccagat acggggcacg ccatcggcac    4680
aacggctacc tcctagccac ctcaacggac tttcaagcat gaagccttca acagcccgcc    4740
attaggcaca gaggccagcc gaccactgct catccggagg cttgctcgcg ctgtcaaagg    4800
```

```
aagatcctcg tcggtgcaag ccaccacgat accactcgag aggccggcac gccatctgca   4860
ccgcaagacg cctcatatgt gtccagtact aagatccatg ataaagaact acggcccgaa   4920
ccagtgagtc aagtcoccaa gatgacgcct ccatggaggg tgcaacatca aagccatcat   4980
cgtcgcccga tcactactag aaaaagggtt ataggtaatc caaacatccg tggctcacgt   5040
ggttggagtg ccccacgggt aaaacaggcg tggcgcacct gtgggcagtg ccctactagt   5100
aactaaatct aaggttttca cccgggacat aaacccctagg cgagaaaggt gctaaaactc   5160
cttggtgacg cgtcataggg aacggcgccc tcgggcgtca ccgtctcatc agctctaaaa   5220
ggcagggctt tcgcaaccga gcattgtccg ttcttctcca tgaggtccta ggctggccct   5280
tcatgggagg agtcaccggc agatccccgc acagctacct cagattagca tcgccagcca   5340
cctagcaccg cccacccttc cgtcagcgcc gcacaagcgc catgagccac cacgccaaga   5400
tggtgttggg cttaaatcaa ccaggcagag caacaacacc ctgcgctcga aacctaggaa   5460
cacgacgat gagtgggcag attggccatg ggccacttga ccaagattag gggaagcaaa    5520
ccagcgccgc catggcacca tccccagctg cccaacacct cccgctacca tcaccgttgc   5580
tcgccatcca gcaacagcgc taccagataa ggatctggca ccagagcccg atcgtgacca   5640
gccaggcagg gcccgagcag cagcgccatc acgccctcca ccatgcgcca acaccgacag   5700
gacacaccac cgtgtcgctc caccaccgc cggaagcggt ggatgggaag ggcgcggcga    5760
gcggctaggg tttgcgccct tggtcgcctg ccataggaac acataccata attatgtaaa   5820
acaacatcag agatgagtga accatagaat caaacgagct tgatgtcggg cgccgccctg   5880
aatcttggaa tatcttgagt gccaccatca agggttgtga gctatatttg tagcacccca   5940
aatcgccttc cccaatgttg tccctggtgt ggaatggtga cctcggttgt ttcttttggc   6000
ggcgggtcga gcacgaagtg gctaaggagg cgtaggagta ggcggaggcc cctgcatcta   6060
gccgggagtc tgatgacgga ggaagggttg aatggagatc tcgacactgg tgccacggaa   6120
ctcgtggcaa tggggcagga acaaggattc gtgccggagt tgacggacgg tgggtggagg   6180
agcggcgggc caatgggca gatggaagca aggaggacga ggagggtgaa gggagcaaat    6240
catgggatga tgcagactcg ctgtagggag gggatcgccg gagatggttg cggcggcaaa   6300
cactagaata gacagacgtc tatgttttat gacgcggaga ttccacatag tcgtgggtgt   6360
tcagagttct acgattcgtg ctattctatt ttgcacttca tcgtcctatc cacccgacga   6420
acctggcacg gtagagaaca aaaattggac tgcggaggtc ctcggcgccg atggcacatc   6480
ccttcgacga atctgacgat gtcgggtcag ggtctgaggt cggccggccc agagtggtgt   6540
cgtgtccatt cccaccttga ttactttcaa ggacctcggc ggctgtcggc gacaggagag   6600
atggccacag catgtgtagg caaagggagg agtggcataa cagcatgaag ttgtgacggc   6660
ggccctccat atttcccgat ctgatgttgc tttattttt ccgatctaga tttgctacac    6720
tatttcatct tctaatccac tgcttctagt ctgttggcat ggcttctgca gaggttattt   6780
ttctgaactt gtggaatatc gtcacatggt ggaagttatg cccctctccg tttgataccg   6840
gtcatggtcc aaatcggctg atcgatacaa aatgattttt gataataaaa ttgtagcgtt   6900
cacttctgac tacttgacct aacacaatct ggacacatgc atgtttagac ccaaaacttc   6960
atggcaattt tccacccata aaggatatat tgccgataaa aattcatttg aggtgttcat   7020
cctcaattca cccacgataat tcaattgatt actagacctg tagatgtggt ttcagactag   7080
atatagaaga agacaaaaag tacatgcgtt gttttgtaaa aaggaacgcc ttgccgataa   7140
aaattggatg taaaccaggg tgttttctcg aagctgtcaa acagctcgta tgaatctaca   7200
```

```
ggctagattg ggcgtccggg ataagcccgg gacgcccaca tgtatataga gtttgatttc    7260
cggtctatgt tgtggagaag aagcaaggga acgggaaaga gagaatgaag ggggaaatga    7320
ggacgaattc gtcctggagc ggacgtctgg ggtatatatc agtggcattg gtgggtaaat    7380
ttcccacaac tctatggccg gttagaaata ttaggaggcg cgggaggtgg agtgaagtag    7440
gtgaagcatt tctttcgcga cttcacaaaa ataaactagg ggcgcgacct gctccactct    7500
agctaaaagg tgaagtttag gccagcttca cccgctccgg tgctaaaacg gtggagtcga    7560
gctgtcccaa acacggtgtg agcagggccg gtcctgagat tttgggggcc ggggcgaga     7620 ctaaaacttg gccccttat taatatagac atcacaatag ttttttgaatt ttaatatata    7680 aatctcaata ataataaatc ttatctatga ttgtaccggt attagcctta aattttttgt    7740
aaatatctcc tctatgagat cctactaagg caaccatctc ttttgctctt ttccttttag    7800
cgtggcaaat ggacactttc tctcgatgaa tacgacatga tatagacgat gctgaaaaac    7860
aaatttatga caaataccga atggtacaaa ctatacatcg tatatgtgaa ggtatatatt    7920
agataatagt aatgcaatat ttaaaacaaa attagaataa agtttttaaaa aagagaaccc    7980 taaaacacga tgagatgtta cctactgcag ctagaaggtc gctgtcagct gatcgttgtg    8040
tcacattaaa cattgaaaaa tgtcctggtt ctgcacgcgt tagactgtcg gtgcagggcc    8100
ctgcgtcgat ggcagcttgg gtgcgtgcgg gcgagcacgc cacacgcgag gagatgagca    8160
gtcactggag gtcgatcgat ggcttatttt ttggtgtcat atgctcctac atgatctatg    8220
gcccatcagg tccttttatt accgttgttg gctgtcaata cctttttactt attccatata   8280 gaaaactgac tttttttttct aagtacctgc atgtagtaca tcacatctca ggtggggccc    8340
ctagattttt ggggccctgg gcggcggcac accctgccca ccccagggcc ggccctgggt    8400
ctgagtaacc tgattttgac gctgttttaa tgatgaatct gactggtgga gcctgaacgt    8460
caggctgatg tgacacatgt ggacggacgg gtgtggatgg ccgttaacgg caaaagttac    8520
aaaaaacccc cacagttggg gctagagttt caaaaaacca tcaaaaaaat aaaaaattta    8580
aaaacaccaa atttggagca agaggttgca aaggttcttt tatgctatta tcatgcaatc    8640
atgacataga ttgttttttag ataaatattg aacaattttt taacaatatt ttaaaacaca    8700
aacagtaaaa gtattttctt ttctaattat tctagggttg tatacaccct tttcttgttt     8760
ttaaattaaa atcaaataaa tcttatctag ctcctctccc aggatccgag ccacatgtga    8820
ggccccctcc ttgtctgcac ccgtaataac atgatataca acaactcgat tatccatccg    8880
ttcatagaaa tacacaagag tagcttcagt catagcttat aaaagcaaca ttagaagtga    8940
gtcaatccaa tgtatggtat tgaacctacc ctaaatttca aagcattttt tagatttaag    9000
tatctgatgt gtagtatcga ttaatgtgtg catagtttgg atcgaagagg atattgacca    9060
atgagcgaag gctatcatcc attgtaaata taagcagaga attgtaattc aaatcattaa    9120
tattgatttg tgtgagctaa taattttcat ttatagcaat tctgcaaaat tctccttagc    9180
cacagcctct gtgcatgtag gctgttagaa taaaattcca gtttcttagt agaaaaatac    9240
tcttcatatc cattttcccc aggatgtgaa gagagttgct aggtctgaat agatctagaa    9300
ttttggtgtt aagtttaatt aaaaaaaagt ttaattagca acactatgca ttataaatgc    9360
ttagttcagg aacatttgtg aaccaattgc atgtctacat tcatttagcc atctctactt    9420
tataggaagg tttaggacat agatccaaat cataatatag atagtattag attgcctgcc    9480
agcctacctg acgagtaggc tatagtaaaa agaaaatgca caagtaaata aacatgattt    9540
```

```
tcatatctag aagaaaaatg cacagctcaa tcagatagag aagataatgc ctgacaagaa      9600
gaagaatcca atgcaaatta gatgagagaa cagtgtcaca gcagaactgc atccacctaa      9660
aacaaaaaat acggtgaaag ccgaaggatt actctcggat atttagaatt gaaccatgtg      9720
tgcaagaagt tttatcatga cacgaaatgc tgcagaaatt gtaagactgg caaaaaatga      9780
agtgcacaag acattaccag cattggagat gaacatggca agacgaggtg cacatctcac      9840
atagatgcag caacctaagt gaaaaaataa cggatagagg aaaatcaacc tgtagcacca      9900
cgctgcagtg aaggcgaatt ttggacgcgc ctaaccatgg actggaagga ttctcttgtg      9960
gatcaaagaa ctcgccctag aaatcaacca agattgttgt tgaagtggcg atgtagctgc     10020
caaacatcgc tggtcgggc acagaaaaaa tagtcggaca cgggactgca gtctccacca      10080
tgactcagaa gatgaggact ccagacagct gcgtcgtgtc cgacacaagg ggccgtagaa     10140
gaggatattt gatctcgagc taagccccctt gggcctcaag catacggtct atacggtaag    10200
aacctctgca acctcttgct ccaatttggt gttttgaaaa aaattatttt tttggtggtc     10260
ttttgaaact ctagccccaa ttgtggtggt tttttgtaat ttttgccgtt aacggccatc     10320
cacgttcgtt cgtccgtcca catgtgtcac gtcagcctga tgttcgggcc ccaccagtca     10380
gagtcatcat tagaggagcg tcaaagccag atcaatgcta tctgcacctt catgtcccaa     10440
atccgatgct ttctgaaatt gttaaagtgt ttggtggtct tttaaaaccc tagccccaat     10500
tgtgatgttt ttttgtaaat ttctcccgca aaaaggagt gagaattagg ttaattctaa      10560
gtctagcgtg cgatctcaga tgcaacccta tttgtaaata aaatatagct gcaaccacac     10620
ttgccaataa agagtgtcac ttataaccac ttgcaactga aaccctactt gcaaccgaaa     10680
atctcactct caattccact tgcaactcaa cagacgcacg aatcactgca gatccaaatag    10740
acaaggagag tatatataat ttttttcccgc cgagtcttaa attagatact atatgcaaca    10800
aaaaaaatat aatttctatc atatttgaaa aaaaatttaa aatggcaaga catgtaaact     10860
tcctttctct acctagagtg aattttttaaa acctaggtac acttgatcca gattatactt    10920
actctgcctc tgggttacat agctttctga atctgaagtt gcgaaaaatt tctgaaaagg     10980
agagttcctt tataccgctt attcagaatt ttgtcatagt tggctcaagc tacatagttt     11040
ttggttttca gtacgaaatt tggcacgctc atacgtgctt ctctacatga aaaatttatt     11100
tcattttttt tactttgttt agttgttatt ttaaatttac tattcataac agattatgag     11160
taccatgttc cactgtgtaa tttggttctt cctcgaaaca ggctttcgtc caactatatt     11220
aatatagcaa ccaaccatga gactgctgct gggccagata gcacaacgcc caaaaacaaa     11280
aagaaaaga aaagaaaaa gaagagaaga cgaaaaacaa aagaagagaa aacaaggccg       11340
ataacagcgg ctcgacgaaa acaaggttgg cccgccatcg ctgcgccctc cggagaatgc    11400
ccaccactga cctagcactc caaaaacgac gcgtatcaag caacaccttc aagaaggaaa     11460
gcgacgacac cgacgatgtt gcccggaaaa atcctagggt ttcccccgat actcggcggg    11520
aggtggagaa gaggtacacc cgacgcccctt caggaaggac ggcaacaccc gcaggcgtta    11580
ccacgtcggt gtcaaaacga caaggatttc tcctgacccc tcaaaaaaac cacattccca     11640
gatgcttcgg attgctccac cactctcacc gcccacaagc atgcgccacc acggacgagc    11700
cgccaccccc gtcatctcac cgtgacccat gatccgagac cggacagaca aaaggaggg    11760
gacttcggcg agagccgatg ctatagaagc acgcgggagg gaactgcctc caccgtcgga    11820
ggacggtaac cgaccggatg caggaacatg ggcaaaccag gccctcgcta gcctggccga    11880
gcccgaatgg tcccgtgaag ccccgctgcc gcactgcagc aagggtgccg ctgccaatat     11940
```

```
caactgtagc gctagcccca cctcccccgt ccaccggagg atccaccgcc actgcagatc    12000
cccaccgcca agctgcagca tcgtcgccat catgcgcacc cggaccaacc ggaccgccac    12060
cggaccgcga cacaccatcg taaaccacct cccggagcca cctccgtcag aaggtcgttc    12120
gcgccgagca ccttcggggg ccgccgcccc agcatccacg ctctcgtgcc cgtaacaggc    12180
agagaacggc tcgccgacgc ctaggaatgc cgcgccaccg acatagcacg gttgtcagac    12240
agagccgtct ttaccagggc aaccaacaga ggacacgcat cgattcggac cgggacagcg    12300
aaggcagcgc caaagcctgc acccagggcc gccggatctg ggcccacctg cccagatcg     12360 acgaccacga cggtgcaaac tggcaagttc aagacacaa ccgcctacag gaggtcgtcg      12420
gagctgacct cccccgatcc cgcctggtcc aggacgaggc ccgcatgccc agatcggggc    12480
ccgcctagcc tcaagatctg gccgcgttgc cggcaaccac ccgctgccgc cacccgggcc    12540
acagagccgc cgcgccgttc gtcgcccgcg ccggagtcg ctgccgctgt gaagacgccg      12600
ccgggccgag taccacgccg cccatgccgc actgccgcag gtggctgccg cccggcgagg    12660
ccgccctgcg cacgggaaaa gaagatcccg ccgccgccag ccccgcgcgg gcttcgcccg    12720
gtggagctct ccggcggcgg cgggggagga gggggaggg agaggcgagt ggcggcgctc      12780
gggatgggag cgtctccgtc gcccgcaccg taatttggtt cttctacgaa gctaagaaaa    12840
taatgttggc attaaccatg ttgcacacac gcattgtcat gtagttttttt cctattgcgt   12900 gtgttgatta atggccagat gcacactgtg tttgtgctac ggaggaatca actgatcgtg    12960
ggcaaccagt ttgttacata ggaataaacg aaagaaagcg aaaatgtcgc aaatctgtga    13020
atacattatg ttgtgggtgt gtcttcatct gggtgttctt ccacctcgtg tcttcctcac    13080
atgtgtgatc cacattctat gttatgaaaa atataatagg gtcaacatta attctggcaa    13140
ataatataat catttctttg aaatgcatgg tgtgtactta tgtttgctga tgaagtatta    13200
gatttaaaac ttgtaatatg tgattatatt tcgcagaact actttgcaaa atgggaggaa    13260
gaaggtgtgg ttgatctgaa atatgagttc aaggagctac tcatgttgat ctcaggtcga    13320
tgccttgttg gaaaagaggt ccgagagaag atgtttggcc agttctgcac attatatcat    13380
caaatcgagg aaggtttgaa ctttgccagt tcatgttcc catacatccc tattccagta     13440
aaccacaggc gtgacagagc acggatcaag cttagaggga ttctctccga ggttgtgagg    13500
tcacgtaaga gcttaaacca tgtcaaggag gatgtgttgc aaaggtttat agatgcaaca    13560
tataaagacg gccgtggcac aaccgtagaa gaggtcagcg cattgatcat taccttgatt    13620
tttgctggaa acactcaag tgcaatgact agcacctgga ctgctgcttg ccttttggat      13680
catgcaaatt ccttagatgc tgctttagag gagcaaagga aaataattgg taaatacaaa    13740
gacaagatag actacaatat attgtcagag atgggcgtcc tgcatagttg catcaaggag    13800
gcggcacgga tgcaccctgc tccgccagcg ttggtccgcc aggtaaagaa gcacgtcaca    13860
gtgcgtacaa aagagggcaa tgaatatggc atttccagag gtcacacctt agtacacctt    13920
gtaatgctca atggtctgtt gccacacatt tacaaggatc ctgaggtgta tgatccagat    13980
cgatttcgtc ccataaggga ggaggataaa gctgctggta aattctccta cacatctttc    14040
ggtgctggaa ggcatgcgtg cggtggagag gcctatgctt acatgcaaat caaaattata    14100
tttagccatt tgctgaggaa ttttgaactc aagctggttt cttctttccc caagccagac    14160
tggacccagt ttctgccaga gcctaaaggg gaagtcatgg taagctataa gagacgtcgt    14220
ttgcctagcg actgactaac atatttttct ctatcttaat atatatatga agacatgcaa    14280
```

-continued

```
gcctttagcg tgttcttga                                              14299
```

<210> SEQ ID NO 20
<211> LENGTH: 22
<212> TYPE: DNA
<213> ORGANISM: Artificial Sequence
<220> FEATURE:
<223> OTHER INFORMATION: Oligonucleotide primer ASCYPA2F01

<400> SEQUENCE: 20

```
cagttagcgt catgttgttc tc                                             22
```

<210> SEQ ID NO 21
<211> LENGTH: 21
<212> TYPE: DNA
<213> ORGANISM: Artificial Sequence
<220> FEATURE:
<223> OTHER INFORMATION: Oligonucleotide primer ASCYPA2R02

<400> SEQUENCE: 21

```
gaacacgcta aaggcttgca t                                              21
```

<210> SEQ ID NO 22
<211> LENGTH: 24
<212> TYPE: DNA
<213> ORGANISM: Artificial Sequence
<220> FEATURE:
<223> OTHER INFORMATION: Oligonucleotide primer ASCYPA2F03

<400> SEQUENCE: 22

```
gcttccctga gaactacacc atgg                                           24
```

<210> SEQ ID NO 23
<211> LENGTH: 22
<212> TYPE: DNA
<213> ORGANISM: Artificial Sequence
<220> FEATURE:
<223> OTHER INFORMATION: Oligonucleotide primer ASCYPA2R04

<400> SEQUENCE: 23

```
atcaaccaca ccttcttcct cc                                             22
```

<210> SEQ ID NO 24
<211> LENGTH: 21
<212> TYPE: DNA
<213> ORGANISM: Artificial Sequence
<220> FEATURE:
<223> OTHER INFORMATION: Oligonucleotide primer ASCYPA2F05

<400> SEQUENCE: 24

```
agcatacccg cttcatcgtt g                                              21
```

<210> SEQ ID NO 25
<211> LENGTH: 1553
<212> TYPE: DNA
<213> ORGANISM: Avena strigosa
<220> FEATURE:
<221> NAME/KEY: misc_feature
<222> LOCATION: (1)..(1553)
<223> OTHER INFORMATION: AsCYPA2 cDNA
<220> FEATURE:
<221> NAME/KEY: misc_feature
<222> LOCATION: (1)..(1553)
<223> OTHER INFORMATION: AsCYPH11 cDNA

<400> SEQUENCE: 25

```
tccctgagaa ctacaccatg gcgttaacag ttagcgtcat gttgttctcc ctagcgcttg     60
```

-continued

```
ttctcatcac tgcagtagtc gcgaagatta caagtgggag aattatcaca gatcccgtgt      120
gtgccctacc agctccacct gaggtcaagg gtattgctct tctcagactc ttgcctactc      180
tgtttacaga gggccctgaa gctacaatgc actatctgca taacaagctt ggcagtgcat      240
tcacagtcag ttttctttgg aaaaagacaa ccttcttggt tggacaggag gcctccgcta      300
ttttcttcca agggttggag tcagaggtta cccaaggaaa tttatttgag tttaccgtcc      360
ccatgtttgg cacagaggta ggcttcggcg tagattacgc tactcgcagg gagcataccc      420
gcttcatcgt tgagtctcta aagccatcac aactcagaag ctatgttgat ccatgctgc      480 aagaagtgga gaactacttt gcaaatggga ggaagaagg tgtggttgat ctgaaatatg      540
agttcaagga gctactcatg ttgatctcag gtcgatgcct tgttggaaaa gaggtccgag      600
agaagatgtt tggccagttc tgcacattat atcatcaaat cgaggaaggt ttgaactttg      660
ccagtttcat gttcccatac atccctattc agtaaaccca caggcgtgac agagcacgga      720
tcaagcttag agggattctc tccgaggttg tgaggtcacg taagagctta aaccatgtca      780
aggaggatgt gttgcaaagg tttatagatg caacatataa agacggccgt ggcacaaccg      840
tagaagaggt cagcgcattg atcattacct tgattttgc tggaaaacac tcaagtgcaa      900
tgactagcac ctggactgct gcttgccttt tggatcatgc aaattcctta gatgctgctt      960
tagaggagca aaggaaaata attggtaaat acaaagacaa gatagactac aatatatatgt     1020 cagagatggg cgtcctgcat agttgcatca aggaggcggc acggatgcac cctgctccgc     1080
cagcgttggt ccgccaggta aagaagcacg tcacagtgcg tacaaaagag ggcaatgaat     1140
atggcatttc cagaggtcac accttagtac accttgtaat gctcaatggt ctgttgccac     1200
acatttacaa ggatcctgag gtgtatgatc cagatcgatt tcgtcccata agggaggagg     1260
ataaagctgc tggtaaattc tcctacacat ctttcggtgc tggaaggcat gcgtgcggtg     1320
gagaggccta tgcttacatg caaatcaaaa ttatatttag ccatttgctg aggaattttg     1380
aactcaagct ggtttcttct ttccccaagc cagactggac ccagtttctg ccagagccta     1440
aaggggaagt catggtaagc tataagagac gtcgtttgcc tagcgactga ctaacatatt     1500
tttctctatc ttaatatata tatgaagaca tgcaagcctt tagcgtgttc ttg            1553
```

```
<210> SEQ ID NO 26
<211> LENGTH: 490
<212> TYPE: PRT
<213> ORGANISM: Avena strigosa
<220> FEATURE:
<221> NAME/KEY: MISC_FEATURE
<222> LOCATION: (1)..(490)
<223> OTHER INFORMATION: AsCYPA2 protein
<220> FEATURE:
<221> NAME/KEY: MISC_FEATURE
<222> LOCATION: (1)..(490)
<223> OTHER INFORMATION: AsCYP51H11 protein

<400> SEQUENCE: 26
```

```
Met Ala Leu Thr Val Ser Val Met Leu Phe Ser Leu Ala Leu Val Leu
 1               5                  10                  15

Ile Thr Ala Val Val Ala Lys Ile Thr Ser Gly Arg Ile Ile Thr Asp
            20                  25                  30

Pro Val Cys Ala Leu Pro Ala Pro Pro Glu Val Lys Gly Ile Ala Leu
        35                  40                  45

Leu Arg Leu Leu Pro Thr Leu Phe Thr Glu Gly Pro Glu Ala Thr Met
    50                  55                  60
```

-continued

```
His Tyr Leu His Asn Lys Leu Gly Ser Ala Phe Thr Val Ser Phe Leu
 65                  70                  75                  80

Trp Lys Lys Thr Thr Phe Leu Val Gly Gln Glu Ala Ser Ala Ile Phe
                 85                  90                  95

Phe Gln Gly Leu Glu Ser Glu Val Thr Gln Gly Asn Leu Phe Glu Phe
            100                 105                 110

Thr Val Pro Met Phe Gly Thr Glu Val Gly Phe Gly Val Asp Tyr Ala
            115                 120                 125

Thr Arg Arg Glu His Thr Arg Phe Ile Val Glu Ser Leu Lys Pro Ser
        130                 135                 140

Gln Leu Arg Ser Tyr Val Asp Pro Met Leu Gln Val Glu Asn Tyr
145                 150                 155                 160

Phe Ala Lys Trp Glu Glu Gly Val Val Asp Leu Lys Tyr Glu Phe
                165                 170                 175

Lys Glu Leu Leu Met Leu Ile Ser Gly Arg Cys Leu Val Gly Lys Glu
            180                 185                 190

Val Arg Glu Lys Met Phe Gly Gln Phe Cys Thr Leu Tyr His Gln Ile
        195                 200                 205

Glu Glu Gly Leu Asn Phe Ala Ser Phe Met Phe Pro Tyr Ile Pro Ile
210                 215                 220

Pro Val Asn His Arg Arg Asp Arg Ala Arg Ile Lys Leu Arg Gly Ile
225                 230                 235                 240

Leu Ser Glu Val Val Arg Ser Arg Lys Ser Leu Asn His Val Lys Glu
                245                 250                 255

Asp Val Leu Gln Arg Phe Ile Asp Ala Thr Tyr Lys Asp Gly Arg Gly
            260                 265                 270

Thr Thr Val Glu Glu Val Ser Ala Leu Ile Ile Thr Leu Ile Phe Ala
            275                 280                 285

Gly Lys His Ser Ser Ala Met Thr Ser Thr Trp Thr Ala Ala Cys Leu
290                 295                 300

Leu Asp His Ala Asn Ser Leu Asp Ala Ala Leu Glu Glu Gln Arg Lys
305                 310                 315                 320

Ile Ile Gly Lys Tyr Lys Asp Lys Ile Asp Tyr Asn Ile Leu Ser Glu
                325                 330                 335

Met Gly Val Leu His Ser Cys Ile Lys Glu Ala Ala Arg Met His Pro
            340                 345                 350

Ala Pro Pro Ala Leu Val Arg Gln Val Lys Lys His Val Thr Val Arg
        355                 360                 365

Thr Lys Glu Gly Asn Glu Tyr Gly Ile Ser Arg Gly His Thr Leu Val
    370                 375                 380

His Leu Val Met Leu Asn Gly Leu Leu Pro His Ile Tyr Lys Asp Pro
385                 390                 395                 400

Glu Val Tyr Asp Pro Asp Arg Phe Arg Pro Ile Arg Glu Glu Asp Lys
                405                 410                 415

Ala Ala Gly Lys Phe Ser Tyr Thr Ser Phe Gly Ala Gly Arg His Ala
            420                 425                 430

Cys Gly Gly Glu Ala Tyr Ala Tyr Met Gln Ile Lys Ile Ile Phe Ser
            435                 440                 445

His Leu Leu Arg Asn Phe Glu Leu Lys Leu Val Ser Ser Phe Pro Lys
        450                 455                 460

Pro Asp Trp Thr Gln Phe Leu Pro Glu Pro Lys Gly Glu Val Met Val
465                 470                 475                 480

Ser Tyr Lys Arg Arg Arg Leu Pro Ser Asp
```

-continued

<210> SEQ ID NO 27
<211> LENGTH: 3727
<212> TYPE: DNA
<213> ORGANISM: Artificial Sequence
<220> FEATURE:
<223> OTHER INFORMATION: AsCYP51H1 entry vector
<220> FEATURE:
<221> NAME/KEY: misc_feature
<222> LOCATION: (1)..(3727)
<223> OTHER INFORMATION: AsCYP51H1 Entry Vector

<400> SEQUENCE: 27

```
ctgacggatg gccttttgc gtttctacaa actcttcctg ttagttagtt acttaagctc      60
gggcccccaaa taatgattt attttgactg atagtgacct gttcgttgca acaaattgat    120
aagcaatgct ttttataat gccaactttg tacaaaaaag caggctggat ccacacgacg    180
ccatggacat gacaatttgc gtcgtttggt tggtcttagc aattatatcc atcgctgcag    240
tagtatccaa gagttcaaag cgaagcaatg cctctgattc agtggtgaca cgaccacctc    300
caccggtggt gacaggaatt gatctcctca agttcttaca tgctctttgt agaaaggacc    360
ctgaagctgc aatgatgtat ctgtataaca agttaggcag tattttcaca ttaagttttt    420
tgtggaaaag agtaaccatc ttgattgggc acgaggcctc cattcctttc tttcatggtt    480
tggagtcaga tgtttcacaa ggaaatttca atgagttcac cgtgccaatg ttcggcaaag    540
agaatgggta tgctgtggaa tatgctactc gaattgagca gtctcgcttc ttctatgatt    600
ctctaaaggc atcgcagctg aggagccatg ttgatctcat tcgacaggaa gtggaggagt    660
actttgcaaa atggggagac gagggtgaag tcgatctgaa acaagagttc accaagttac    720
tcatgttgat tgctggtcgc tgcctacttg gaagtgaggt ccgagatacg atatttggtg    780
agttctacac attgtttgct gatattgagg aggggtcaa cttgttcagt tacatgttcc    840
catatatgcc ggttccagta aacaaccgac gagacagagc acaaatgaag cttacaagta    900
tagtgtctga gattgtgagg tcaagaaaga atgcaaccg cgtcgaggat gatatgctgc    960
agagactgat agattccaga tataaagatg gtcgtccaac aactgaaggg gaggtttccg   1020
ggatgatcat tggacttata tttgctggaa agcacacaag tacaatcact gcctcctgga   1080
ccggagcttg cctttgacc catccaaaat tcctaggtgc tgctgtcgag gagcaaaagc   1140
aaatgatgag taaatacaag gataatatag actacaatat cctgtcagaa atggagattt   1200
tgcatagttg catcaaagag gcaggtcgga tgtatcccgc agcgccggtg ttgctgcgca   1260
agacactgaa ggagatcagt gtgcagacaa gagaggagg tgaatatggt atccctaaag   1320
gtaccacgtt agcacatctt gtaatgctaa caggtaaggt gccacacact acaaggacc   1380
ccgaggtcta tgatccagat cggtttcgtg ttggaagaga ggaggataaa attgggggta   1440
aactctctta cacaattttt ggtgctggaa ggcatgcttg cgctggcgag tcctttgctt   1500
tcatgcaaat aaagattatc tggagccatt tgctgagaaa ttttgatctt aaactgactt   1560
ctccatttcc caagcaagat tggagcaagt ttataatga gcctaaaggc aaagtaatgg   1620
taagttacaa gagatgtcgt atgcctgcaa actaagatat ctagacccag ctttcttgta   1680
caaagttggc attataagaa agcattgctt atcaattgt tgcaacgaac aggtcactat   1740
cagtcaaaat aaaatcatta tttgccatcc agctgcagct ctggcccgtg tctcaaaatc   1800
tctgatgtta cattgcacaa gataaaaata tatcatcatg aacaataaaa ctgtctgctt   1860
acataaacag taatacaagg ggtgttatga gccatattca acgggaaacg tcgaggccgc   1920
```

```
gattaaattc caacatggat gctgatttat atgggtataa atgggctcgc gataatgtcg      1980
ggcaatcagg tgcgacaatc tatcgcttgt atgggaagcc cgatgcgcca gagttgtttc      2040
tgaaacatgg caaaggtagc gttgccaatg atgttacaga tgagatggtc agactaaact      2100
ggctgacgga atttatgcct cttccgacca tcaagcattt tatccgtact cctgatgatg      2160
catggttact caccactgcg atccccggaa aaacagcatt ccaggtatta gaagaatatc      2220
ctgattcagg tgaaaatatt gttgatgcgc tggcagtgtc cctgcgccgg ttgcattcga      2280
ttcctgtttg taattgtcct tttaacagcg atcgcgtatt tcgtctcgct caggcgcaat      2340
cacgaatgaa taacggtttg gttgatgcga gtgattttga tgacgagcgt aatggctggc      2400
ctgttgaaca agtctggaaa gaaatgcata actttttgcc attctcaccg gattcagtcg      2460
tcactcatgg tgatttctca cttgataacc ttatttttga cgaggggaaa ttaataggtt      2520
gtattgatgt tggacgagtc ggaatcgcag accgatacca ggatcttgcc atcctatgga      2580
actgcctcgg tgagttttct ccttcattac agaaacggct ttttcaaaaa tatggtattg      2640
ataatcctga tatgaataaa ttgcagtttc atttgatgct cgatgagttt ttctaatcag      2700
aattggttaa ttggttgtaa cattattcag attgggcccc gttccactga gcgtcagacc      2760
ccgtagaaaa gatcaaagga tcttcttgag atccttttt tctgcgcgta atctgctgct      2820
tgcaaacaaa aaaaccaccg ctaccagcgg tggtttgttt gccggatcaa gagctaccaa      2880
ctctttttcc gaaggtaact ggcttcagca gagcgcagat accaaatact gttcttctag      2940
tgtagccgta gttaggccac cacttcaaga actctgtagc accgcctaca tacctcgctc      3000
tgctaatcct gttaccagtg gctgctgcca gtggcgataa gtcgtgtctt accgggttgg      3060
actcaagacg atagttaccg gataaggcgc agcggtcggg ctgaacgggg ggttcgtgca      3120
cacagcccag cttggagcga acgacctaca ccgaactgag atacctacag cgtgagctat      3180
gagaaagcgc cacgcttccc gaagggagaa aggcggacag gtatccggta agcggcaggg      3240
tcggaacagg agagcgcacg agggagcttc caggggggaaa cgcctggtat ctttatagtc      3300
ctgtcgggtt tcgccacctc tgacttgagc gtcgattttt gtgatgctcg tcagggggc      3360 ggagcctatg gaaaaacgcc agcaacgcgg ccttttttacg gttcctggcc ttttgctggc      3420
cttttgctca catgttcttt cctgcgttat cccctgattc tgtggataac cgtattaccg      3480
ctagcatgga tctcggggac gtctaactac taagcgagag tagggaactg ccaggcatca      3540
aataaaacga aaggctcagt cggaagactg ggcctttcgt tttatctgtt gtttgtcggt      3600
gaacgctctc ctgagtagga caaatccgcc gggagcggat ttgaacgttg tgaagcaacg      3660
gcccggaggg tggcgggcag gacgcccgcc ataaactgcc aggcatcaaa ctaagcagaa      3720
ggccatc                                                               3727

<210> SEQ ID NO 28
<211> LENGTH: 4520
<212> TYPE: DNA
<213> ORGANISM: Artificial Sequence
<220> FEATURE:
<223> OTHER INFORMATION: Entry Vector for BAS
<220> FEATURE:
<221> NAME/KEY: misc_feature
<222> LOCATION: (1)..(4520)
<223> OTHER INFORMATION: BAS entry vector

<400> SEQUENCE: 28
ctgacggatg gcctttttgc gtttctacaa actcttcctg ttagttagtt acttaagctc       60
```

-continued

| | |
|---|---|
| gggccccaac tttattatac aaagttggca ttataaaaaa gcattgctta tcaatttgtt | 120 |
| gcaacgaaca ggtcactatc agtcaaaata aaatcattat ttggatccac acgacgccat | 180 |
| gtggaggcta acaataggtg agggcggcgg tccgtggctg aagtcgaaca atggcttcct | 240 |
| tggccgccaa gtgtgggagt acgacgccga tgccggcacg ccggaagagc gtgccgaggt | 300 |
| tgagagggtg cgtgcggaat tcacaaagaa caggttccag aggaaggagt cacaggacct | 360 |
| tcttctacgc ttgcagtacg caaaagacaa ccctcttccg gcgaatattc cgacagaagc | 420 |
| caagcttgaa aagagtacag aggtcactca cgagactatc tacgaatcat tgatgcgagc | 480 |
| tttacatcaa tattcctctc tacaagcaga cgatgggcat tggcctggtg attacagtgg | 540 |
| gattctcttc attatgccta tcattatatt ctctttatat gttactagat cacttgacac | 600 |
| cttttatct ccggaacatc gtcatgagat atgtcgctac atttacaatc aacagaatga | 660 |
| agatggtggt tggggaaaaa tggttcttgg cccaagtacc atgtttggat cgtgtatgaa | 720 |
| ttatgcaacc ttaatgattc ttggcgagaa gcgaatggt gatcataagg atgcattgga | 780 |
| aaaagggcgt tcttggattt tatctcatgg aactgcaact gcaataccac agtggggaaa | 840 |
| aatatggttg tcgataattg gcgtttacga atggtcagga acaatcccta ttatacctga | 900 |
| attgtggttg gttccacatt ttcttccgat tcacccaggt cgttttggt gttttacccg | 960 |
| gttgatatac atgtcaatgg catatctcta tggtaagaaa tttgttgggc ctattagtcc | 1020 |
| tacaatatta gctctgcgac aagacctcta tagtataccct tactgcaaca ttaattggga | 1080 |
| caaggcgcgt gattattgtg caaaggagga ccttcattac ccacgctcac gggcacaaga | 1140 |
| tcttatatct ggttgcctaa cgaaaattgt ggagccaatt ttgaattggt ggccagcaaa | 1200 |
| caagctaaga gatagagctt taactaacct catggagcat atccattatg acgacgaatc | 1260 |
| aaccaaatat gtgggcattt gccctattaa caaggcattg aacatgattt gttgttgggt | 1320 |
| agaaaaccca aattcgcctg aattccaaca acatcttcca cgattccatg actatttgtg | 1380 |
| gatggcggag gatggaatga aggcacaggt atatgatgga tgtcatagct gggaactagc | 1440 |
| gttcataatt catgcctatt gttccacgga tcttactagc gagtttatcc cgactctaaa | 1500 |
| aaaggcgcac gagttcatga agaactcaca ggttctttc aaccacccaa atcatgaaag | 1560 |
| ctattatcgc cacagatcaa aaggctcatg gacccttca agtgtagata atggttggtc | 1620 |
| tgtatctgat tgtactgcgg aagctgttaa ggcattgcta ctattatcaa agatatccgc | 1680 |
| tgaccttgtt ggcgatccaa taaaacaaga caggttgtat gatgccttg attgcatcct | 1740 |
| atctttcatg aatacagatg gaacattttc tacctacgaa tgcaaacgga cattcgcttg | 1800 |
| gttagaggtt ctcaacccctt ctgagagttt tcggaacatt gtcgtggact atccatctgt | 1860 |
| tgaatgcaca tcatctgtgg ttgatgctct catattattt aaagagacga atccacgata | 1920 |
| tcgaagagca gagatagata aatgcattga agaagctgtt gtatttattg agaacagtca | 1980 |
| aaataaggat ggttcatggt atggctcatg gggtatatgt ttcgcatatg gatgcatgtt | 2040 |
| tgcagtaagg gcgttggttg ctacaggaaa aacctacgac aattgtgctt ctatcaggaa | 2100 |
| atcatgcaaa tttgtcttat caaagcaaca acaacaggt ggatggggtg aagactatct | 2160 |
| ttctagtgac aatggggaat atattgatag cggtaggcct aatgctgtga ccacctcatg | 2220 |
| ggcaatgttg gctttaattt atgctggaca ggttgaacgt gacccagtac cactgtataa | 2280 |
| tgctgcaaga cagctaatga atatgcagct agaaacaggt gacttccccc aacaggaaca | 2340 |
| catgggttgc ttcaactcct ccttgaactt caactacgcc aactaccgca atctataccc | 2400 |
| gattatggct cttggggaac ttcgccgtcg acttcttgcg attaagagct gagttatcta | 2460 |

```
gaaataatga ttttatttttg actgatagtg acctgttcgt tgcaacaaat tgataagcaa    2520 tgcttttta  taatgccaac tttgtataga aaagttgcca tccagctgca gctctggccc    2580
gtgtctcaaa atctctgatg ttacattgca caagataaaa atatatcatc atgaacaata    2640
aaactgtctg cttacataaa cagtaataca aggggtgtta tgagccatat tcaacgggaa    2700
acgtcgaggc cgcgattaaa ttccaacatg gatgctgatt tatatgggta taaatgggct    2760
cgcgataatg tcgggcaatc aggtgcgaca atctatcgct tgtatgggaa gcccgatgcg    2820
ccagagttgt ttctgaaaca tggcaaaggt agcgttgcca atgatgttac agatgagatg    2880
gtcagactaa actggctgac ggaatttatg cctcttccga ccatcaagca ttttatccgt    2940
actcctgatg atgcatggtt actcaccact gcgatcccg  gaaaaacagc attccaggta    3000
ttagaagaat atcctgattc aggtgaaaat attgttgatg cgctggcagt gtccctgcgc    3060
cggttgcatt cgattcctgt ttgtaattgt ccttttaaca gcgatcgcgt atttcgtctc    3120
gctcaggcgc aatcacgaat gaataacggt ttggttgatg cgagtgattt tgatgacgag    3180
cgtaatggct ggcctgttga acaagtctgg aaagaaatgc ataaactttt gccattctca    3240
ccggattcag tcgtcactca tggtgatttc tcacttgata accttatttt tgacgagggg    3300
aaattaatag gttgtattga tgttggacga gtcggaatcg cagaccgata ccaggatctt    3360
gccatcctat ggaactgcct cggtgagttt ctccttcat  tacagaaacg gcttttttcaa    3420 aaatatggta ttgataatcc tgatatgaat aaattgcagt ttcatttgat gctcgatgag    3480 ttttttctaat cagaattggt taattggttg taacattatt cagattgggc cccgttccac    3540
tgagcgtcag acccccgtaga aaagatcaaa ggatcttctt gagatccttt ttttctgcgc    3600
gtaatctgct gcttgcaaac aaaaaaacca ccgctaccag cggtggtttg tttgccggat    3660
caagagctac caactctttt tccgaaggta actggcttca gcagagcgca gataccaaat    3720
actgttcttc tagtgtagcc gtagttaggc caccacttca agaactctgt agcaccgcct    3780
acatacctcg ctctgctaat cctgttacca gtggctgctg ccagtggcga taagtcgtgt    3840
cttaccgggt tggactcaag acgatagtta ccggataagg cgcagcggtc gggctgaacg    3900
gggggttcgt gcacacagcc cagcttggag cgaacgacct acaccgaact gagataccta    3960
cagcgtgagc tatgagaaag cgccacgctt cccgaaggga gaaaggcgga caggtatccg    4020
gtaagcggca gggtcggaac aggagagcgc acgagggagc ttccagggg  aaacgcctgg    4080 tatctttata gtcctgtcgg gtttcgccac ctctgacttg agcgtcgatt tttgtgatgc    4140
tcgtcagggg ggcggagcct atggaaaaac gccagcaacg cggcctttt  acggttcctg    4200 gccttttgct ggccttttgc tcacatgttc tttcctgcgt tatcccctga ttctgtggat    4260
aaccgtatta ccgctagcat ggatctcggg gacgtctaac tactaagcga gagtagggaa    4320
ctgccaggca tcaaataaaa cgaaaggctc agtcggaaga ctgggccttt cgttttatct    4380
gttgtttgtc ggtgaacgct ctcctgagta ggacaaatcc gccgggagcg gatttgaacg    4440
ttgtgaagca acggcccgga gggtggcggg caggacgccc gccataaact gccaggcatc    4500
aaactaagca gaaggccatc                                                4520
```

<210> SEQ ID NO 29
<211> LENGTH: 7525
<212> TYPE: DNA
<213> ORGANISM: Artificial Sequence
<220> FEATURE:
<223> OTHER INFORMATION: Maize recombinant DNA construct 1

<400> SEQUENCE: 29

```
gtttacccgc caatatatcc tgtcaaacac tgatagttta aactgaaggc gggaaacgac    60
aatctgatca tgagcggaga attaagggag tcacgttatg accccgccg atgacgcggg    120
acaagccgtt ttacgtttgg aactgacaga accgcaacgt tgaaggagcc actcagccca   180
agctggtacg attgtaatac gactcactat agggcgaatt gagcgctgtt taaacgctct   240
tcaactggaa gagcggttac ccggaccgaa gcttagcccg atccccgggg ctgcaggaat   300
tcccatggag tcaaagattc aaatagagga cctaacagaa ctcgccgtaa agactggcga   360
acagttcata cagagtctct tacgactcaa tgacaagaag aaaatcttcg tcaacatggt   420
ggagcacgac acgcttgtct actccaaaaa tatcaaagat acagtctcag aagaccaaag   480
ggcaattgag acttttcaac aaagggtaat atccggaaac ctcctcggat tccattgccc   540
agctatctgt cactttattg tgaagatagt ggaaaaggaa ggtggctcct acaaatgcca   600
tcattgcgat aaaggaaagg ccatcgttga agatgcctct gccgacagtg gtcccaaaga   660
tggacccca cccacgagga gcatcgtgga aaagaagac gttccaacca cgtcttcaaa    720
gcaagtggat tgatgtgata tcaagctggg catgcctgca gtgcagcgtg accggtcgt    780
gccctctct agagataatg agcattgcat gtctaagtta taaaaaatta ccacatattt    840
tttttgtcac acttgtttga agtgcagttt atctatcttt atacatatat ttaaacttta   900
ctctacgaat aatataatct atagtactac aataatatca gtgttttaga gaatcatata   960
aatgaacagt tagacatggt ctaaaggaca attgagtatt ttgacaacag gactctacag  1020
ttttatcttt ttagtgtgca tgtgttctcc tttttttttg caaatagctt cacctatata  1080
atacttcatc cattttatta gtacatccat ttagggttta gggttaatgg ttttttataga 1140
ctaattttttt tagtacatct attttattct atttagcct ctaaattaag aaaactaaaa  1200
ctctatttta gttttttat ttaataattt agatataaaa tagaataaaa taaagtgact  1260
aaaaattaaa caaatacccct ttaagaaatt aaaaaaacta aggaaacatt tttcttgttt  1320
cgagtagata atgccagcct gttaaacgcc gtcgacgagt ctaacggaca ccaaccagcg  1380
aaccagcagc gtcgcgtcgg gccaagcgaa gcagacggca cggcatctct gtcgctgcct  1440
ctggaccct ctcgagagtt ccgctccacc gttggacttg ctccgctgtc ggcatccaga   1500
aattgcgtgg cggagcggca gacgtgagcc ggcacggcag gcggcctcct cctcctctca  1560
cggcacggca gctacggggg attccttttcc caccgctcct tcgctttccc ttcctcgccc  1620
gccgtaataa atagacaccc cctccacacc ctctttcccc aacctcgtgt tgttcggagc  1680
gcacacacac acaaccagat ctcccccaaa tccaccgtc ggcacctccg cttcaaggta   1740
cgccgctcgt cctcccccc cccccctctc taccttctct agatcggcgt tccggtccat   1800
ggttagggcc cggtagttct acttctgttc atgtttgtgt tagatccgtg tttgtgttag  1860
atccgtgctg ctagcgttcg tacacggatg cgacctgtac gtcagacacg ttctgattgc  1920
taacttgcca gtgtttctct ttggggaatc ctgggatggc tctagccgtt ccgcagacgg  1980
gatcgatttc atgatttttt ttgtttcgtt gcatagggtt tggtttgccc ttttcctttta 2040
tttcaatata tgccgtgcac ttgtttgtcg ggtcatcttt tcatgctttt ttttgtcttg  2100
gttgtgatga tgtggtctgg ttgggcggtc gttctagatc ggagtagaat tctgtttcaa  2160
actacctggt ggatttatta attttggatc tgtatgtgtg tgccatacat attcatagtt  2220
acgaattgaa gatgatggat ggaaatatcg atctaggata ggtatacatg ttgatgcggg  2280
ttttactgat gcatatacag agatgctttt tgttcgcttg gttgtgatga tgtggtgtgg  2340
```

```
ttgggcggtc gttcattcgt tctagatcgg agtagaatac tgtttcaaac tacctggtgt    2400
atttattaat tttggaactg tatgtgtgtg tcatacatct tcatagttac gagtttaaga    2460
tggatggaaa tatcgatcta ggataggtat acatgttgat gtgggtttta ctgatgcata    2520
tacatgatgg catatgcagc atctattcat atgctctaac cttgagtacc tatctattat    2580
aataaacaag tatgttttat aattattttg atcttgatat acttggatga tggcatatgc    2640
agcagctata tgtggatttt tttagccctg ccttcatacg ctatttattt gcttggtact    2700
gtttcttttg tcgatgctca ccctgttgtt tggtgttact tctgcaggtc gactctagag    2760
gatccacaag tttgtacaaa aaagcaggct ggatccacac gacgccatgg acatgacaat    2820
ttgcgtcgtt tggttggtct tagcaattat atccatcgct gcagtagtat ccaagagttc    2880
aaagcgaagc aatgcctctg attcagtggt gacacgacca cctccaccgg tggtgacagg    2940
aattgatctc ctcaagttct tacatgctct ttgtagaaag gaccctgaag ctgcaatgat    3000
gtatctgtat aacaagttag gcagtatttt cacattaagt ttttttgtgga aaagagtaac    3060 catcttgatt gggcacgagg cctccattcc tttctttcat ggtttggagt cagatgtttc    3120
acaaggaaat ttcaatgagt tcaccgtgcc aatgttcggc aaagagaatg ggtatgctgt    3180
ggaatatgct actcgaattg agcagtctcg cttcttctat gattctctaa aggcatcgca    3240
gctgaggagc catgttgatc tcattcgaca ggaagtggag gagtactttg caaaatgggg    3300
agacgagggt gaagtcgatc tgaaacaaga gttcaccaag ttactcatgt tgattgctgg    3360
tcgctgccta cttggaagtg aggtccgaga tacgatattt ggtgagttct acacattgtt    3420
tgctgatatt gaggaggggg tcaacttgtt cagttacatg ttcccatata tgccggttcc    3480
agtaaacaac cgacgagaca gagcacaaat gaagcttaca agtatagtgt ctgagattgt    3540
gaggtcaaga aagagatgca accgcgtcga ggatgatatg ctgcagagac tgatagattc    3600
cagatataaa gatggtcgtc caacaactga aggggaggtt tccgggatga tcattggact    3660
tatatttgct ggaaagcaca caagtacaat cactgcctcc tggaccggag cttgccttt    3720 gacccatcca aaattcctag gtgctgctgt cgaggagcaa aagcaaatga tgagtaaata    3780
caaggataat atagactaca atatcctgtc agaaatggag attttgcata gttgcatcaa    3840
agaggcaggt cggatgtatc ccgcagcgcc ggtgttgctg cgcaagacac tgaaggagat    3900
cagtgtgcag acaagagagg gaggtgaata tggtatccct aaaggtacca cgttagcaca    3960
tcttgtaatg ctaacaggta aggtgccaca cacttacaag gaccccgagg tctatgatcc    4020
agatcggttt cgtgttggaa gagaggagga taaaattggg ggtaaactct cttacacaat    4080
ttttggtgct ggaaggcatg cttgcgctgg cgagtccttt gctttcatgc aaataaagat    4140
tatctggagc catttgctga gaaattttga tcttaaactg acttctccat ttcccaagca    4200
agattggagc aagtttataa tagagcctaa aggcaaagta atggtaagtt acaagagatg    4260
tcgtatgcct gcaaactaag atatctagac ccagctttct tgtacaaagt ggtgttaacc    4320
tagacttgtc catcttctgg attggccaac ttaattaatg tatgaaataa aaggatgcac    4380
acatagtgac atgctaatca ctataatgtg ggcatcaaag ttgtgtgtta tgtgtaatta    4440
ctagttatct gaataaaaga gaaagagatc atccatattt cttatcctaa atgaatgtca    4500
cgtgtcttta taattctttg atgaaccaga tgcatttcat taaccaaatc catatacata    4560
taaatattaa tcatatataa ttaatatcaa ttgggttagc aaaacaaatc tagtctaggt    4620
gtgttttgcg aattgcggcc gccaccgcgg tggagctcga attccggtcc gggtcacctt    4680
```

-continued

```
tgtccaccaa gatggaactg cggccgctca ttaattaagt caggcgcgcc tctagttgaa      4740
gacacgttca tgtcttcatc gtaagaagac actcagtagt cttcggccag aatggcccgg      4800
accgaagctt ctgcaggaat tctgagctag cgaagttcct attccgaagt tcctattctt      4860
caaaaagtat aggaacttca gacgtcctcg agtccgtcct gtagaaaccc caacccgtga      4920
aatcaaaaaa ctcgacggcc tgtgggcatt cagtctggat cgcgaaaact gtggaattga      4980
tccagaattc gctagcgaag ttcctattcc gaagttccta ttctctagaa agtataggaa      5040
cttcagatct gagcttctag aaatccgtca acatggtgga gcacgacact ctcgtctact      5100
ccaagaatat caaagataca gtctcagaag accaaagggc tattgagact tttcaacaaa      5160
gggtaatatc gggaaacctc ctcggattcc attgcccagc tatctgtcac ttcatcaaaa      5220
ggacagtaga aaaggaaggt ggcacctaca aatgccatca ttgcgataaa ggaaaggcta      5280
tcgttcaaga tgcctctgcc gacagtggtc ccaaagatgg acccccaccc acgaggagca      5340
tcgtggaaaa agaagacgtt ccaaccacgt cttcaaagca gtggattga tgtgatgctc      5400 tagaaatccg tcaacatggt ggagcacgac actctcgtct actccaagaa tatcaaagat      5460
acagtctcag aagaccaaag ggctattgag acttttcaac aaagggtaat atcgggaaac      5520
ctcctcggat tccattgccc agctatctgt cacttcatca aaaggacagt agaaaaggaa      5580
ggtggcacct acaaatgcca tcattgcgat aaaggaaagg ctatcgttca agatgcctct      5640
gccgacagtg gtcccaaaga tggaccccca cccacgagga gcatcgtgga aaaagaagac      5700
gttccaacca cgtcttcaaa gcaagtggat tgatgtgata tctccactga cgtaagggat      5760
gacgcacaat cccactatcc ttcgcaagac ccttcctcta tataaggaag ttcatttcat      5820
ttggagagga cgagctgcag gtcgacggat caagtgcaaa ggtccgcctt gtttctcctc      5880
tgtctcttga tctgactaat cttggtttat gattcgttga gtaattttgg ggaaagcttc      5940
gtccacagtt ttttttttcga tgaacagtgc cgcagtggcg ctgatcttgt atgctatcct      6000
gcaatcgtgg tgaacttatg tcttttatat ccttcactac catgaaaagg ctagtaatct      6060
ttctcgatgt aacatcgtcc agcactgcta ttaccgtgtg gtccatccga cagtctggct      6120
gaacacatca tacgatattg agcaaagatc gatctatctt ccctgttctt taatgaaaga      6180
cgtcattttc atcagtatga tctaagaatg ttgcaacttg caaggaggcg tttctttctt      6240
tgaatttaac taactcgttg agtggccctg tttctcggac gtaaggcctt tgctgctcca      6300
cacatgtcca ttcgaatttt accgtgttta gcaagggcga aaagtttgca tcttgatgat      6360
ttagcttgac tatgcgattg ctttcctgga cccgtgcagc tgcggacgga tccaccatga      6420
gcccagaacg acgcccggcc gacatccgcc gtgccaccga gcggacatg ccggcggtct      6480 gcaccatcgt caaccactac atcgagacaa gcacggtcaa cttccgtacc gagccgcagg      6540
aaccgcagga gtggacggac gacctcgtcc gtctgcggga gcgctatccc tggctcgtcg      6600
ccgaggtgga cggcgaggtc gccggcatcg cctacgcggg ccctggaag gcacgcaacg      6660 cctacgactg gacggccgag tcgaccgtgt acgtctcccc ccgccaccag cggacgggac      6720
tgggctccac gctctacacc cacctgctga gtccctggag gcacagggc ttcaagagcg      6780 tggtcgctgt catcgggctg cccaacgacc cgagcgtgcg catgcacgag gcgctcggat      6840 atgcccccg cggcatgctg cgggcggcc gcttcaagca cggaactgg catgacgtgg      6900 gtttctggca gctggacttc agcctgccgg taccgccccg tccggtcctg cccgtcaccg      6960
agatctgatc cgtcgaccaa cctagacttg tccatcttct ggattggcca acttaattaa      7020
tgtatgaaat aaaaggatgc acacatagtg acatgctaat cactataatg tgggcatcaa      7080
```

| | |
|---|---:|
| agttgtgtgt tatgtgtaat tactagttat ctgaataaaa gagaaagaga tcatccatat | 7140 |
| ttcttatcct aaatgaatgt cacgtgtctt tataattctt tgatgaacca gatgcatttc | 7200 |
| attaaccaaa tccatataca tataaatatt aatcatatat aattaatatc aattgggtta | 7260 |
| gcaaaacaaa tctagtctag gtgtgttttg cgaattgcgg ccgctctagc gaagttccta | 7320 |
| ttccgaagtt cctattctct agaaagtata ggaacttcag atccagaatt cggtccgggc | 7380 |
| catcgtggcc tcttgctctt caggatgaag agctatgttt aaacgtgcaa gcgctactag | 7440 |
| acaattcagt acattaaaaa cgtccgcaat gtgttattaa gttgtctaag cgtcaatttg | 7500 |
| tttacaccac aatatatcct gccac | 7525 |

```
<210> SEQ ID NO 30
<211> LENGTH: 12125
<212> TYPE: DNA
<213> ORGANISM: Artificial Sequence
<220> FEATURE:
<223> OTHER INFORMATION: maize recombinant DNA construct 2

<400> SEQUENCE: 30
```

| | |
|---|---:|
| gtttacccgc caatatatcc tgtcaaacac tgatagttta aactgaaggc gggaaacgac | 60 |
| aatctgatca tgagcggaga attaagggag tcacgttatg accccgccg atgacgcggg | 120 |
| acaagccgtt ttacgtttgg aactgacaga accgcaacgt tgaaggagcc actcagccca | 180 |
| agctggtacg attgtaatac gactcactat agggcgaatt gagcgctgtt taaacgctct | 240 |
| tcaactggaa gagcggttac ccggaccgaa gcttgcatgc ctgcacccat ggagtcaaag | 300 |
| attcaaatag aggacctaac agaactcgcc gtaaagactg gcgaacagtt catacagagt | 360 |
| ctcttacgac tcaatgacaa gaagaaaatc ttcgtcaaca tggtggagca cgacacgctt | 420 |
| gtctactcca aaaatatcaa agatacagtc tcagaagacc aaagggcaat tgagactttt | 480 |
| caacaaaggg taatatccgg aaacctcctc ggattccatt gcccagctat ctgtcacttt | 540 |
| attgtgaaga tagtggaaaa ggaaggtggc tcctacaaat gccatcattg cgataaagga | 600 |
| aaggccatcg ttgaagatgc ctctgccgac agtggtccca agatggaccc ccacccacg | 660 |
| aggagcatcg tggaaaaaga agacgttcca accacgtctt caaagcaagt ggattgatgt | 720 |
| gatatcaagc tgggcatgcc tgcagtgcag cgtgacccgg tcgtgcccct ctctagagat | 780 |
| aatgagcatt gcatgtctaa gttataaaaa attaccacat attttttttg tcacacttgt | 840 |
| ttgaagtgca gtttatctat ctttatacat atatttaaac tttactctac gaataatata | 900 |
| atctatagta ctacaataat atcagtgttt tagagaatca tataaatgaa cagttagaca | 960 |
| tggtctaaag gacaattgag tattttgaca acaggactct acagtttat cttttttagtg | 1020 |
| tgcatgtgtt ctccttttt tttgcaaata gcttcaccta tataatactt catccatttt | 1080 |
| attagtacat ccatttaggg tttagggtta atggttttta tagactaatt ttttagtac | 1140 |
| atctatttta ttctatttta gcctctaaat taagaaaact aaaactctat tttagttttt | 1200 |
| ttatttaata atttagatat aaaatagaat aaaataaagt gactaaaaat taaacaaata | 1260 |
| cccctttaaga aattaaaaaa actaaggaaa cattttctt gtttcgagta gataatgcca | 1320 |
| gcctgttaaa cgccgtcgac gagtctaacg gacaccaacc agcgaaccag cagcgtcgcg | 1380 |
| tcgggccaag cgaagcagac ggcacggcat ctctgtcgct gcctctggac ccctctcgag | 1440 |
| agttccgctc caccgttgga cttgctccgc tgtcggcatc cagaaattgc gtggcggagc | 1500 |
| ggcagacgtg agccggcacg gcaggcggcc tcctcctcct ctcacggcac ggcagctacg | 1560 |

```
ggggattcct ttcccaccgc tccttcgctt tcccttcctc gcccgccgta ataaatagac   1620
accccctcca cacccthtttt ccccaacctc gtgttgttcg gagcgcacac acacacaacc   1680
agatctcccc caaatccacc cgtcggcacc tccgcttcaa ggtacgccgc tcgtcctccc   1740
cccccccccc tctctacctt ctctagatcg gcgttccggt ccatggttag ggcccggtag   1800
ttctacttct gttcatgttt gtgttagatc cgtgtttgtg ttagatccgt gctgctagcg   1860
ttcgtacacg gatgcgacct gtacgtcaga cacgttctga ttgctaactt gccagtgttt   1920
ctctttgggg aatcctggga tggctctagc cgttccgcag acgggatcga tttcatgatt   1980
ttttttgttt cgttgcatag ggtttggttt gccctttttcc tttatttcaa tatatgccgt   2040
gcacttgttt gtcgggtcat cttttcatgc ttttttttgt cttggttgtg atgatgtggt   2100
ctggttgggc ggtcgttcta gatcggagta gaattctgtt tcaaactacc tggtggatt    2160 attaatttg  gatctgtatg tgtgtgccat acatattcat agttacgaat tgaagatgat   2220
ggatggaaat atcgatctag gataggtata catgttgatg cgggttttac tgatgcatat   2280
acagagatgc ttttgttcg cttggttgtg atgatgtggt gtggttgggc ggtcgttcat    2340
tcgttctaga tcggagtaga atactgtttc aaactacctg gtgtatttat taattttgga   2400
actgtatgtg tgtgtcatac atcttcatag ttacgagttt aagatggatg gaaatatcga   2460
tctaggatag gtacatgt tgatgtgggt tttactgatg catatacatg atggcatatg     2520
cagcatctat tcatatgctc taaccttgag tacctatcta ttataataaa caagtatgtt   2580
ttataattat tttgatcttg atatacttgg atgatggcat atgcagcagc tatatgtgga   2640 ttttttttagc cctgccttca tacgctattt atttgcttgg tactgttttct tttgtcgatg   2700 ctcaccctgt tgtttggtgt tacttctgca ggtcgactct agaggatcca caagtttgta   2760
caaaaaagca ggctggatcc acacgacgcc atggacatga caatttgcgt cgtttggttg   2820
gtcttagcaa ttatatccat cgctgcagta gtatccaaga gttcaaagcg aagcaatgcc   2880
tctgattcag tggtgacacg accacctcca ccggtggtga caggaattga tctcctcaag   2940
ttcttacatg ctctttgtag aaaggaccct gaagctgcaa tgatgtatct gtataacaag   3000
ttaggcagta ttttcacatt aagttttttg tggaaaagag taaccatctt gattgggcac   3060
gaggcctcca ttcctttctt tcatggtttg gagtcgatg tttcacaagg aaatttcaat    3120
gagttcaccg tgccaatgtt cggcaaagag aatgggtatg ctgtggaata tgctactcga   3180
attgagcagt ctcgcttctt ctatgattct ctaaaggcat cgcagctgag gagccatgtt   3240
gatctcattc gacaggaagt ggaggagtac tttgcaaaat ggggagacga gggtgaagtc   3300
gatctgaaac aagagttcac caagttactc atgttgattg ctggtcgctg cctacttgga   3360
agtgaggtcc gagatacgat atttggtgag ttctacacat tgtttgctga tattgaggag   3420
ggggtcaact tgttcagtta catgttccca tatatgccgg ttccagtaaa caaccgacga   3480
gacagagcac aaatgaagct tacaagtata gtgtctgaga ttgtgaggtc aagaaagaga   3540
tgcaaccgcg tcgaggatga tatgctgcag agactgatag attccagata taaagatggt   3600
cgtccaacaa ctgaagggga ggtttccggg atgatcattg gacttatatt tgctggaaag   3660
cacacaagta caatcactgc ctcctggacc ggagcttgcc ttttgaccca tccaaaattc   3720
ctaggtgctg ctgtcgagga gcaaaagcaa atgatgagta aatacaagga taatatagac   3780
tacaatatcc tgtcagaaat ggagattttg catagttgca tcaaagaggc aggtcggatg   3840
tatcccgcag cgccggtgtt gctgcgcaag acactgaagg agatcagtgt gcagacaaga   3900
gagggaggtg aatatggtat ccctaaaggt accacgttag cacatcttgt aatgctaaca   3960
```

```
ggtaaggtgc cacacactta caaggacccc gaggtctatg atccagatcg gtttcgtgtt    4020
ggaagagagg aggataaaat tgggggtaaa ctctcttaca caattttttgg tgctggaagg   4080
catgcttgcg ctggcgagtc ctttgctttc atgcaaataa agattatctg gagccatttg    4140
ctgagaaatt ttgatcttaa actgacttct ccatttccca agcaagattg gagcaagttt    4200
ataatagagc ctaaaggcaa agtaatggta agttacaaga gatgtcgtat gcctgcaaac    4260
taagatatct agacccagct ttcttgtaca aagtggtgtt aacctagact tgtccatctt    4320
ctggattggc caacttaatt aatgtatgaa ataaaaggat gcacacatag tgacatgcta    4380
atcactataa tgtgggcatc aaagttgtgt gttatgtgta attactagtt atctgaataa    4440
aagagaaaga gatcatccat atttcttatc ctaaatgaat gtcacgtgtc tttataattc    4500
tttgatgaac cagatgcatt tcattaacca aatccatata catataaata ttaatcatat    4560
ataattaata tcaattgggt tagcaaaaca aatctagtct aggtgtgttt tgcgaattgc    4620
ggccgcggac cgaagcttgc atgcctgcag tgcagcgtga cccggtcgtg cccctctcta    4680
gagataatga gcattgcatg tctaagttat aaaaaattac cacatatttt ttttgtcaca    4740
cttgtttgaa gtgcagttta tctatcttta tacatatatt taaactttac tctacgaata    4800
atataatcta tagtactaca ataatatcag tgtttagag aatcatataa atgaacagtt    4860
agacatggtc taaaggacaa ttgagtattt tgacaacagg actctacagt tttatctttt    4920
tagtgtgcat gtgttctcct tttttttgc aaatagcttc acctatataa tacttcatcc    4980
attttattag tacatccatt taggggtttag ggttaatggt ttatagac taattttttt    5040
agtacatcta ttttattcta ttttagcctc taaattaaga aaactaaaac tctattttag    5100
tttttttatt taataattta gatataaaat agaataaaat aaagtgacta aaaattaaac    5160
aaatacccctt taagaaatta aaaaactaa ggaaacattt ttcttgtttc gagtagataa    5220
tgccagcctg ttaaacgccg tcgacgagtc taacggacac caaccagcga accagcagcg    5280
tcgcgtcggg ccaagcgaag cagacggcac ggcatctctg tcgctgcctc tggacccctc    5340
tcgagagttc cgctccaccg ttggacttgc tccgctgtcg gcatccagaa attgcgtggc    5400
ggagcggcag acgtgagccg gcacggcagg cggcctcctc ctcctctcac ggcacggcag    5460
ctacggggga ttccttttccc accgctcctt cgctttccct tcctcgcccg ccgtaataaa    5520
tagacacccc ctccacaccc tctttcccca acctcgtgtt gttcggagcg cacacacaca    5580
caaccagatc tcccccaaat ccacccgtcg gcacctccgc ttcaaggtac gccgctcgtc    5640
ctcccccccc ccccctctct accttctcta gatcggcgtt ccggtccatg gttagggccc    5700
ggtagttcta cttctgttca tgtttgtgtt agatccgtgt ttgtgttaga tccgtgctgc    5760
tagcgttcgt acacggatgc gacctgtacg tcagacacgt tctgattgct aacttgccag    5820
tgtttctctt tggggaatcc tgggatggct ctagccgttc cgcagacggg atcgatttca    5880
tgatttttttt tgtttcgttg catagggttt ggtttgccct tttcctttat ttcaatatat    5940
gccgtgcact tgtttgtcgg gtcatctttt catgcttttt tttgtcttgg ttgtgatgat    6000
gtggtctggt tgggcggtcg ttctagatcg gagtagaatt ctgtttcaaa ctacctggtg    6060
gatttattaa ttttggatct gtatgtgtgt gccatacata ttcatagtta cgaattgaag    6120
atgatggatg gaaatatcga tctaggatag gtatacatgt tgatgcgggt tttactgatg    6180
catatacaga gatgcttttt gttcgcttgg ttgtgatgat gtggtgtggt tgggcggtcg    6240
ttcattcgtt ctagatcgga gtagaatact gtttcaaact acctggtgta tttattaatt    6300
```

```
ttggaactgt atgtgtgtgt catacatctt catagttacg agtttaagat ggatggaaat    6360
atcgatctag gataggtata catgttgatg tgggttttac tgatgcatat acatgatggc    6420
atatgcagca tctattcata tgctctaacc ttgagtacct atctattata ataaacaagt    6480
atgttttata attattttga tcttgatata cttggatgat ggcatatgca gcagctatat    6540
gtggattttt ttagccctgc cttcatacgc tatttatttg cttggtactg tttcttttgt    6600
cgatgctcac cctgttgttt ggtgttactt ctgcaggtcg actctagagg atcccaactt    6660
tattatacaa agttgggatc cacacgacgc catgtggagg ctaacaatag gtgagggcgg    6720
cggtccgtgg ctgaagtcga acaatggctt ccttggccgc caagtgtggg agtacgacgc    6780
cgatgccggc acgccggaag agcgtgccga ggttgagagg gtgcgtgcgg aattcacaaa    6840
gaacaggttc cagaggaagg agtcacagga ccttcttcta cgcttgcagt acgcaaaaga    6900
caaccctctt ccggcgaata ttccgacaga agccaagctt gaaaagagta cagaggtcac    6960
tcacgagact atctacgaat cattgatgcg agctttacat caatattcct ctctacaagc    7020
agacgatggg cattggcctg gtgattacag tgggattctc ttcattatgc ctatcattat    7080
attctcttta tatgttacta gatcacttga cacctttta tctccggaac atcgtcatga    7140
gatatgtcgc tacatttaca atcaacagaa tgaagatggt ggttggggaa aaatggttct    7200
tggcccaagt accatgtttg gatcgtgtat gaattatgca accttaatga ttcttggcga    7260
gaagcgaaat ggtgatcata aggatgcatt ggaaaaaggg cgttcttgga ttttatctca    7320
tggaactgca actgcaatac cacagtgggg aaaaatatgg ttgtcgataa ttggcgttta    7380
cgaatggtca ggaaacaatc ctattatacc tgaattgtgg ttggttccac atttcttcc    7440
gattcaccca ggtcgtttt ggtgttttac ccggttgata tacatgtcaa tggcatatct    7500
ctatggtaag aaatttgttg ggcctattag tcctacaata ttagctctgc gacaagacct    7560
ctatagtata ccttactgca acattaattg ggacaaggcg cgtgattatt gtgcaaagga    7620
ggaccttcat tacccacgct cacgggcaca agatcttata tctggttgcc taacgaaaat    7680
tgtggagcca attttgaatt ggtggccagc aaacaagcta agagatagag ctttaactaa    7740
cctcatggag catatccatt atgacgacga atcaaccaaa tatgtgggca tttgccctat    7800
taacaaggca ttgaacatga tttgttgttg ggtagaaaac ccaaattcgc ctgaattcca    7860
acaacatctt ccacgattcc atgactattt gtggatggcg gaggatggaa tgaaggcaca    7920
ggtatatgat ggatgtcata gctgggaact agcgttcata attcatgcct attgttccac    7980
ggatcttact agcgagttta tcccgactct aaaaaaggcg cacgagttca tgaagaactc    8040
acaggttctt ttcaaccacc caaatcatga aagctattat cgccacagat caaaaggctc    8100
atggacccct tcaagtgtag ataatggttg gtctgtatct gattgtactg cggaagctgt    8160
taaggcattg ctactattat caaagatatc cgctgacctt gttggcgatc caataaaaca    8220
agacaggttg tatgatgcca ttgattgcat cctatctttc atgaatacag atggaacatt    8280
ttctacctac gaatgcaaac ggacattcgc ttggttagag gttctcaacc cttctgagag    8340
ttttcggaac attgtcgtgg actatccatc tgttgaatgc acatcatctg tggttgatgc    8400
tctcatatta tttaaagaga cgaatccacg atatcgaaga gcagagatag ataaatgcat    8460
tgaagaagct gttgtatta ttgagaacag tcaaaataag gatggttcat ggtatggctc    8520
atggggtata tgtttcgcat atggatgcat gtttgcagta agggcgttgg ttgctacagg    8580
aaaaacctac gacaattgtg cttctatcag gaaatcatgc aaatttgtct tatcaaagca    8640
acaaacaaca ggtggatggg gtgaagacta tctttctagt gacaatgggg aatatattga    8700
```

-continued

```
tagcggtagg cctaatgctg tgaccacctc atgggcaatg ttggctttaa tttatgctgg    8760
acaggttgaa cgtgacccag taccactgta taatgctgca agacagctaa tgaatatgca    8820
gctagaaaca ggtgacttcc cccaacagga acacatgggt tgcttcaact cctccttgaa    8880
cttcaactac gccaactacc gcaatctata cccgattatg gctcttgggg aacttcgccg    8940
tcgacttctt gcgattaaga gctgagttat ctagcaactt tgtatagaaa agttggttaa    9000
cctagacttg tccatcttct ggattggcca acttaattaa tgtatgaaat aaaaggatgc    9060
acacatagtg acatgctaat cactataatg tgggcatcaa agttgtgtgt tatgtgtaat    9120
tactagttat ctgaataaaa gagaaagaga tcatccatat ttcttatcct aaatgaatgt    9180
cacgtgtctt tataattctt tgatgaacca gatgcatttc attaaccaaa tccatataca    9240
tataaatatt aatcatatat aattaatatc aattgggtta gcaaaacaaa tctagtctag    9300
gtgtgttttg cgaattcggt ccggcgcgcc tctagttgaa gacacgttca tgtcttcatc    9360
gtaagaagac actcagtagt cttcggccag aatggcccgg accgaagctt ctgcaggaat    9420
tctgagctag cgaagttcct attccgaagt tcctattctt caaaaagtat aggaacttca    9480
gacgtcctcg agtccgtcct gtagaaaccc caacccgtga aatcaaaaaa ctcgacggcc    9540
tgtgggcatt cagtctggat cgcgaaaact gtggaattga tccagaattc gctagcgaag    9600
ttcctattcc gaagttccta ttctctagaa agtataggaa cttcagatct gagcttctag    9660
aaatccgtca acatggtgga gcacgacact ctcgtctact ccaagaatat caaagataca    9720
gtctcagaag accaaagggc tattgagact ttcaacaaa gggtaatatc gggaaacctc    9780
ctcggattcc attgcccagc tatctgtcac ttcatcaaaa ggacagtaga aaggaaggt    9840
ggcacctaca aatgccatca ttgcgataaa ggaaaggcta tcgttcaaga tgcctctgcc    9900
gacagtggtc ccaaagatgg acccccaccc acgaggagca tcgtggaaaa agaagacgtt    9960
ccaaccacgt cttcaaagca agtggattga tgtgatgctc tagaaatccg tcaacatggt   10020
ggagcacgac actctcgtct actccaagaa tatcaaagat acagtctcag aagaccaaag   10080
ggctattgag acttttcaac aaagggtaat atcgggaaac ctcctcggat tccattgccc   10140
agctatctgt cacttcatca aaaggacagt agaaaggaa ggtggcacct acaaatgcca   10200
tcattgcgat aaaggaaagg ctatcgttca agatgcctct gccgacagtg gtcccaaaga   10260
tggaccccca cccacgagga gcatcgtgga aaaagaagac gttccaacca cgtcttcaaa   10320
gcaagtggat tgatgtgata tctccactga cgtaagggat gacgcacaat cccactatcc   10380
ttcgcaagac ccttcctcta taaggaag ttcatttcat ttggagagga cgagctgcag   10440
gtcgacggat caagtgcaaa ggtccgcctt gtttctcctc tgtctcttga tctgactaat   10500
cttggtttat gattcgttga gtaattttgg ggaaagcttc gtccacagtt ttttttttcga   10560
tgaacagtgc cgcagtggcg ctgatcttgt atgctatcct gcaatcgtgg tgaacttatg   10620
tcttttatat ccttcactac catgaaaagg ctagtaatct ttctcgatgt aacatcgtcc   10680
agcactgcta ttaccgtgtg gtccatccga cagtctggct gaacacatca tacgatattg   10740
agcaaagatc gatctatctt ccctgttctt taatgaaaga cgtcattttc atcagtatga   10800
tctaagaatg ttgcaacttg caaggaggcg tttctttctt tgaatttaac taactcgttg   10860
agtggccctg tttctcggac gtaaggcctt tgctgctcca cacatgtcca ttcgaatttt   10920
accgtgttta gcaagggcga aaagtttgca tcttgatgat ttagcttgac tatgcgattg   10980
ctttcctgga cccgtgcagc tgcggacgga tccaccatga gcccagaacg acgcccggcc   11040
```

| | | | | |
|---|---|---|---|---|
| gacatccgcc | gtgccaccga | ggcggacatg | ccggcggtct | gcaccatcgt caaccactac | 11100 |
| atcgagacaa | gcacggtcaa | cttccgtacc | gagccgcagg | aaccgcagga ctggacggac | 11160 |
| gacctcgtcc | gtctgcggga | gcgctatccc | tggctcgtcg | ccgaggtgga cggcgaggtc | 11220 |
| gccggcatcg | cctacgcggg | cccctggaag | gcacgcaacg | cctacgactg gacggccgag | 11280 |
| tcgaccgtgt | acgtctcccc | ccgccaccag | cggacgggac | tgggctccac gctctacacc | 11340 |
| cacctgctga | agtccctgga | ggcacagggc | ttcaagagcg | tggtcgctgt catcgggctg | 11400 |
| cccaacgacc | cgagcgtgcg | catgcacgag | gcgctcggat | atgcccccccg cggcatgctg | 11460 |
| cgggcggccg | gcttcaagca | cgggaactgg | catgacgtgg | gtttctggca gctggacttc | 11520 |
| agcctgccgg | taccgccccg | tccggtcctg | cccgtcaccg | agatctgatc cgtcgaccaa | 11580 |
| cctagacttg | tccatcttct | ggattggcca | acttaattaa | tgtatgaaat aaaaggatgc | 11640 |
| acacatagtg | acatgctaat | cactataatg | tgggcatcaa | agttgtgtgt tatgtgtaat | 11700 |
| tactagttat | ctgaataaaa | gagaaagaga | tcatccatat | ttcttatcct aaatgaatgt | 11760 |
| cacgtgtctt | tataattctt | tgatgaacca | gatgcatttc | attaaccaaa tccatataca | 11820 |
| tataaatatt | aatcatatat | aattaatatc | aattgggtta | gcaaaacaaa tctagtctag | 11880 |
| gtgtgttttg | cgaattgcgg | ccgctctagc | gaagttccta | ttccgaagtt cctattctct | 11940 |
| agaaagtata | ggaacttcag | atccagaatt | cggtccgggc | catcgtggcc tcttgctctt | 12000 |
| caggatgaag | agctatgttt | aaacgtgcaa | gcgctactag | acaattcagt acattaaaaa | 12060 |
| cgtccgcaat | gtgttattaa | gttgtctaag | cgtcaatttg | tttacaccac aatatatcct | 12120 |
| gccac | | | | | 12125 |

<210> SEQ ID NO 31
<211> LENGTH: 2574
<212> TYPE: DNA
<213> ORGANISM: Artificial Sequence
<220> FEATURE:
<223> OTHER INFORMATION: Soybean recombinant DNA construct 1

<400> SEQUENCE: 31

| | | | | |
|---|---|---|---|---|
| cgacgtacgc | gtatcgatgg | cgccagctgc | aggcggccgc | catatgcatc ctaggcctat | 60 |
| taatattccg | gagtatacgt | agccggctaa | cgttaacaac | cggtacctct agaactatag | 120 |
| ctagcatgcg | tttaaactag | agatccgtca | acatggtgga | gcacgacact ctcgtctact | 180 |
| ccaagaatat | caaagataca | gtctcagaag | accaaagggc | tattgagact tttcaacaaa | 240 |
| gggtaatatc | gggaaacctc | ctcggattcc | attgcccagc | tatctgtcac ttcatcaaaa | 300 |
| ggacagtaga | aaaggaaggt | ggcacctaca | aatgccatca | ttgcgataaa ggaaaggcta | 360 |
| tcgttcaaga | tgcctctgcc | gacagtggtc | ccaaagatgg | accccacccc acgaggagca | 420 |
| tcgtggaaaa | agaagacgtt | ccaaccacgt | cttcaaagca | agtggattga tgtgatgatc | 480 |
| ctatgcgtat | ggtatgacgt | gtgttcaaga | tgatgacttc | aaacctacct atgacgtatg | 540 |
| gtatgacgtg | tgtcgactga | tgacttagat | ccactcgagc | ggctataaat acgtacctac | 600 |
| gcaccctgcg | ctaccatccc | tagagctgca | gcttattttt | acaacaatta ccaacaacaa | 660 |
| caaacaacaa | acaacattac | aattactatt | tacaattaca | gtcgacccgg tcgccaccat | 720 |
| ggacatgaca | atttgcgtcg | tttggttggt | cttagcaatt | atatccatcg ctgcagtagt | 780 |
| atccaagagt | tcaaagcgaa | gcaatgcctc | tgattcagtg | gtgacacgac cacctccacc | 840 |
| ggtggtgaca | ggaattgatc | tcctcaagtt | cttacatgct | ctttgtagaa aggaccctga | 900 |
| agctgcaatg | atgtatctgt | ataacaagtt | aggcagtatt | ttcacattaa gttttttgtg | 960 |

```
gaaaagagta accatcttga ttgggcacga ggcctccatt cctttctttc atggtttgga    1020
gtcagatgtt tcacaaggaa atttcaatga gttcaccgtg ccaatgttcg gcaaagagaa    1080
tgggtatgct gtggaatatg ctactcgaat tgagcagtct cgcttcttct atgattctct    1140
aaaggcatcg cagctgagga gccatgttga tctcattcga caggaagtgg aggagtactt    1200
tgcaaaatgg ggagacgagg gtgaagtcga tctgaaacaa gagttcacca agttactcat    1260
gttgattgct ggtcgctgcc tacttggaag tgaggtccga gatacgatat tggtgagtt     1320 ctacacattt tttgctgata ttgaggaggg ggtcaacttg ttcagttaca tgttcccata    1380
tatgccggtt ccagtaaaca accgacgaga cagagcacaa atgaagctta caagtatagt    1440
gtctgagatt gtgaggtcaa gaaagagatg caaccgcgtc gaggatgata tgctgcagag    1500
actgatagat tccagatata agatggtcg tccaacaact gaaggggagg tttccgggat     1560
gatcattgga cttatatttg ctggaaagca cacaagtaca atcactgcct cctggaccgg    1620
agcttgcctt ttgacccatc caaaattcct aggtgctgct gtcgaggagc aaaagcaaat    1680
gatgagtaaa tacaaggata atatagacta caatatcctg tcagaaatgg agattttgca    1740
tagttgcatc aaagaggcag gtcggatgta tcccgcagcg ccggtgttgc tgcgcaagac    1800
actgaaggag atcagtgtgc agacaagaga gggaggtgaa tatggtatcc ctaaaggtac    1860
cacgttagca catcttgtaa tgctaacagg taaggtgcca cacacttaca aggaccccga    1920
ggtctatgat ccagatcggt ttcgtgttgg aagagaggag gataaaattg ggggtaaact    1980
ctcttacaca atttttggtg ctggaaggca tgcttgcgct ggcgagtcct ttgctttcat    2040
gcaaataaag attatctgga gccatttgct gagaaatttt gatcttaaac tgacttctcc    2100
atttcccaag caagattgga gcaagtttat aatagagcct aaaggcaaag taatggtaag    2160
ttacaagaga tgtcgtatgc ctgcaaacta aggatcctta gagtcaacct agacttgtcc    2220
atcttctgga ttggccaact taattaatgt atgaaataaa aggatgcaca catagtgaca    2280
tgctaatcac tataatgtgg gcatcaaagt tgtgtgttat gtgtaattac tagttatctg    2340
aataaaagag aaagagatca tccatatttc ttatcctaaa tgaatgtcac gtgtctttat    2400
aattctttga tgaaccagat gcatttcatt aaccaaatcc atatacatat aaatattaat    2460
catatataat taatatcaat tgggttagca aaacaaatct agtctaggtg tgttttgcga    2520
attaaggtcc gggtaacccc aatcgctacg ctcagcccgg tatgttgtta tagc           2574

<210> SEQ ID NO 32
<211> LENGTH: 6889
<212> TYPE: DNA
<213> ORGANISM: Artificial Sequence
<220> FEATURE:
<223> OTHER INFORMATION: Soybean Recombinant DNA construct 2

<400> SEQUENCE: 32
cgacgtacgc gtatcgatgg cgccagctgc aggcggccgc catatgcatc ctaggcctat      60
taatattccg gagtatacgt agccggctaa cgttaacaac cggtacctct agaactatag     120
ctagcatgcg tttaaactag agatccgtca acatggtgga gcacgacact ctcgtctact     180
ccaagaatat caaagataca gtctcagaag accaaagggc tattgagact ttcaacaaa     240 gggtaatatc gggaaacctc ctcggattcc attgcccagc tatctgtcac ttcatcaaaa    300
ggacagtaga aaaggaaggt ggcacctaca atgccatca ttgcgataaa ggaaaggcta     360
tcgttcaaga tgcctctgcc gacagtggtc ccaaagatgg acccccaccc acgaggagca    420
```

```
tcgtggaaaa agaagacgtt ccaaccacgt cttcaaagca agtggattga tgtgatgatc    480
ctatgcgtat ggtatgacgt gtgttcaaga tgatgacttc aaacctacct atgacgtatg    540
gtatgacgtg tgtcgactga tgacttagat ccactcgagc ggctataaat acgtacctac    600
gcaccctgcg ctaccatccc tagagctgca gcttattttt acaacaatta ccaacaacaa    660
caaacaacaa acaacattac aattactatt tacaattaca gtcgacccgg tcgccaccat    720
ggacatgaca atttgcgtcg tttggttggt cttagcaatt atatccatcg ctgcagtagt    780
atccaagagt tcaaagcgaa gcaatgcctc tgattcagtg gtgacacgac cacctccacc    840
ggtggtgaca ggaattgatc tcctcaagtt cttacatgcc ctttgtagaa aggaccctga    900
agctgcaatg atgtatctgt ataacaagtt aggcagtatt ttcacattaa gttttttgtg    960
gaaaagagta accatcttga ttgggcacga ggcctccatt cctttctttc atggtttgga   1020
gtcagatgtt tcacaaggaa atttcaatga gttcaccgtg ccaatgttcg gcaaagagaa   1080
tgggtatgct gtggaatatg ctactcgaat tgagcagtct cgcttcttct atgattctct   1140
aaaggcatcg cagctgagga gccatgttga tctcattcga caggaagtgg aggagtactt   1200
tgcaaaatgg ggagacgagg gtgaagtcga tctgaaacaa gagttcacca gttactcat   1260
gttgattgct ggtcgctgcc tacttggaag tgaggtccga gatacgatat ttggtgagtt   1320
ctacacattg tttgctgata ttgaggaggg ggtcaacttg ttcagttaca tgttcccata   1380
tatgccggtt ccagtaaaca accgacgaga cagagcacaa atgaagctta caagtatagt   1440
gtctgagatt gtgaggtcaa gaaagagatg caaccgcgtc gaggatgata tgctgcagag   1500
actgatagat tccagatata aagatggtcg tccaacaact gaaggggagg tttccgggat   1560
gatcattgga cttatatttg ctggaaagca cacaagtaca atcactgcct cctggaccgg   1620
agcttgcctt ttgacccatc caaaattcct aggtgctgct gtcgaggagc aaaagcaaat   1680
gatgagtaaa tacaaggata atatagacta caatatcctg tcagaaatgg agattttgca   1740
tagttgcatc aaagaggcag gtcggatgta tcccgcagcg ccggtgttgc tgcgcaagac   1800
actgaaggag atcagtgtgc agacaagaga gggaggtgaa tatggtatcc ctaaaggtac   1860
cacgttagca catcttgtaa tgctaacagg taaggtgcca cacacttaca aggaccccga   1920
ggtctatgat ccagatcggt ttcgtgttgg aagagaggag gataaaattg ggggtaaact   1980
ctcttacaca atttttggtg ctggaaggca tgcttgcgct ggcgagtcct ttgctttcat   2040
gcaaataaag attatctgga gccatttgct gagaaatttt gatcttaaac tgacttctcc   2100
atttcccaag caagattgga gcaagtttat aatagagcct aaaggcaaag taatggtaag   2160
ttacaagaga tgtcgtatgc ctgcaaacta aggatcctta gagtcaacct agacttgtcc   2220
atcttctgga ttggccaact taattaatgt atgaaataaa aggatgcaca catagtgaca   2280
tgctaatcac tataatgtgg gcatcaaagt tgtgtgttat gtgtaattac tagttatctg   2340
aataaaagag aaagagatca tccatatttc ttatcctaaa tgaatgtcac gtgtctttat   2400
aattctttga tgaaccagat gcatttcatt aaccaaatcc atatacatat aaatattaat   2460
catatataat taatatcaat tgggttagca aaacaaatct agtctaggtg tgttttgcga   2520
attaaggtcc gggtaacccc aatcgctacg ctcagccgtt cactcggcct gacttaatta   2580
atgagcggcc gcagttccat cttggtggac aaaggtgacc cggaccgaag ctggggatc   2640
tgagcttcta gctagagatc cgtcaacatg gtggagcacg acactctcgt ctactccaag   2700
aatatcaaag atacagtctc agaagaccaa agggctattg agactttca acaagggta    2760
atatcgggaa acctcctcgg attccattgc ccagctatct gtcacttcat caaaaggaca   2820
```

```
gtagaaaagg aaggtggcac ctacaaatgc catcattgcg ataaaggaaa ggctatcgtt    2880
caagatgcct ctgccgacag tggtcccaaa gatggacccc cacccacgag gagcatcgtg    2940
gaaaaagaag acgttccaac cacgtcttca aagcaagtgg attgatgtga tgatcctatg    3000
cgtatggtat gacgtgtgtt caagatgatg acttcaaacc tacctatgac gtatggtatg    3060
acgtgtgtcg actgatgact tagatccact cgactagaga taatgagcat tgcatgtcta    3120
agttataaaa aattaccaca tattttttt gtcacacttg tttgaagtgc agtttatcta    3180
tctttataca tatatttaaa ctttactcta cgaataatat aatctatagt actacaataa    3240
tatcagtgtt ttagagaatc atataaatga acagttagac atggtctaaa ggacaattga    3300
gtattttgac aacaggactc tacagtttta tcttttagt gtgcatgtgt tctccttttt    3360
ttttgcaaat agcttcacct atataatact tcatccattt tattagtaca tccatttagg    3420
gtttagggtt aatggttttt atagactaat ttttttagta catctatttt attctatttt    3480
agcctctaaa ttaagaaaac taaaactcta ttttagtttt tttatttaat aatttagata    3540
taaaatagaa taaaataaag tgactaaaaa ttaaacaaat acccttttaag aaattaaaaa    3600 aactaaggaa acattttct tgtttcgagt agataatgcc agcctgttaa acgccgtcga    3660
cgagtctaac ggacaccaac cagcgaacca gcagcgtcgc gtcgggccaa gcgaagcaga    3720
cggcacggca tctctgtcgc tgcctctgga cccctctcga gagttccgct ccaccgttgg    3780
acttgctccg ctgtcggcat ccagaaattg cgtggcggag cggcagacgt gagccggcac    3840
ggcaggcggc ctcctcctcc tctcacggca ccggcagcta cggggattc ctttcccacc    3900 gctcctacta gaactagtgg atcctatgcg tatggtatga cgtgtgttca agatgatgac    3960
ttcaaaccta cctatgacgt atggtatgac gtgtgtcgac tgatgactta gatccactcg    4020
agcggctata aatacgtacc tacgcaccct gcgctaccat ccctagagct gcagcttatt    4080
tttacaacaa ttaccaacaa caacaaacaa caaacaacat tacaattact atttacaatt    4140
acagtcgacc cagcttggaa tctagaacca tgtggaggct aacaataggt gagggcggcg    4200
gtccgtggct gaagtcgaac aatggcttcc ttggccgcca agtgtgggag tacgacgccg    4260
atgccggcac gccggaagag cgtgccgagg ttgagagggt gcgtgcggaa ttcacaaaga    4320
acaggttcca gaggaaggag tcacaggacc ttcttctacg cttgcagtac gcaaaagaca    4380
accctcttcc ggcgaatatt ccgacagaag ccaagcttga aaagagtaca gaggtcactc    4440
acgagactat ctacgaatca ttgatgcgag ctttacatca atattcctct ctacaagcag    4500
acgatgggca ttggcctggt gattacagtg ggattctctt cattatgcct atcattatat    4560
tctctttata tgttactaga tcacttgaca cctttttatc tccggaacat cgtcatgaga    4620
tatgtcgcta catttacaat caacagaatg aagatggtgg ttggggaaaa atggttcttg    4680
gcccaagtac catgtttgga tcgtgtatga attatgcaac cttaatgatt cttggcgaga    4740
agcgaaatgg tgatcataag gatgcattgg aaaaagggcg ttcttggatt ttatctcatg    4800
gaactgcaac tgcaatacca cagtggggaa aaatatggtt gtcgataatt ggcgtttacg    4860
aatggtcagg aaacaatcct attatacctg aattgtggtt ggttccacat tttcttccga    4920
ttcacccagg tcgttttttgg tgttttaccc ggttgatata catgtcaatg gcatatctct    4980
atggtaagaa atttgttggg cctattagtc ctacaatatt agctctgcga caagacctct    5040
atagtatacc ttactgcaac attaattggg acaaggcgcg tgattattgt gcaaaggagg    5100
accttcatta cccacgctca cgggcacaag atcttatatc tggttgccta acgaaaattg    5160
```

-continued

```
tggagccaat tttgaattgg tggccagcaa acaagctaag agatagagct ttaactaacc      5220
tcatggagca tatccattat gacgacgaat caaccaaata tgtgggcatt tgccctatta      5280
acaaggcatt gaacatgatt tgttgttggg tagaaaaccc aaattcgcct gaattccaac      5340
aacatcttcc acgattccat gactatttgt ggatggcgga ggatggaatg aaggcacagg      5400
tatatgatgg atgtcatagc tgggaactag cgttcataat tcatgcctat tgttccacgg      5460
atcttactag cgagtttatc ccgactctaa aaaaggcgca cgagttcatg aagaactcac      5520
aggttctttt caaccaccca aatcatgaaa gctattatcg ccacagatca aaaggctcat      5580
ggacccttc  aagtgtagat aatggttggt ctgtatctga ttgtactgcg gaagctgtta      5640
aggcattgct actattatca aagatatccg ctgaccttgt tggcgatcca ataaaacaag      5700
acaggttgta tgatgccatt gattgcatcc tatctttcat gaatacagat ggaacatttt      5760
ctacctacga atgcaaacgg acattcgctt ggttagaggt tctcaaccct tctgagagtt      5820
ttcggaacat tgtcgtggac tatccatctg ttgaatgcac atcatctgtg gttgatgctc      5880
tcatattatt taaagagacg aatccacgat atcgaagagc agagatagat aaatgcattg      5940
aagaagctgt tgtatttatt gagaacagtc aaaataagga tggttcatgg tatggctcat      6000
ggggtatatg tttcgcatat ggatgcatgt ttgcagtaag ggcgttggtt gctacaggaa      6060
aaacctacga caattgtgct tctatcagga aatcatgcaa atttgtctta tcaaagcaac      6120
aaacaacagg tggatggggt gaagactatc tttctagtga caatgggaa  tatattgata      6180
gcggtaggcc taatgctgtg accacctcat gggcaatgtt ggctttaatt tatgctggac      6240
aggttgaacg tgacccagta ccactgtata atgctgcaag acagctaatg aatatgcagc      6300
tagaaacagg tgacttcccc caacaggaac acatgggttg cttcaactcc tccttgaact      6360
tcaactacgc caactaccgc aatctatacc cgattatggc tcttggggaa cttcgccgtc      6420
gacttcttgc gattaagagc tgacccgggt taacctagac ttgtccatct tctggattgg      6480
ccaacttaat taatgtatga aataaaagga tgcacacata gtgacatgct aatcactata      6540
atgtgggcat caaagttgtg tgttatgtgt aattactagt tatctgaata aaagagaaag      6600
agatcatcca tatttcttat cctaaatgaa tgtcacgtgt ctttataatt ctttgatgaa      6660
ccagatgcat ttcattaacc aaatccatat acatataaat attaatcata tataattaat      6720
atcaattggg ttagcaaaac aaatctagtc taggtgtgtt ttgcgaatgg actggccgtc      6780
tgctagccgg ttgttaacgt tagccggcta cgtatactcc ggaatattaa taggcctagg      6840
atgcatatgg cggccgcctg cagctggcgc catcgatacg cgtacgtcg                  6889
```